United States Patent
Petersheim et al.

(12)

(10) Patent No.: US 12,303,398 B2
(45) Date of Patent: *May 20, 2025

(54) LOW PROFILE PLATE

(71) Applicant: GLOBUS MEDICAL, INC., Audubon, PA (US)

(72) Inventors: Samuel Petersheim, Elverson, PA (US); Jason Cianfrani, Conshohocken, PA (US)

(73) Assignee: Globus Medical Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/342,826

(22) Filed: Jun. 28, 2023

(65) Prior Publication Data

US 2023/0338160 A1     Oct. 26, 2023

Related U.S. Application Data

(63) Continuation of application No. 17/140,358, filed on Jan. 4, 2021, now Pat. No. 11,717,417, which is a
(Continued)

(51) Int. Cl.
| | |
|---|---|
| *A61F 2/44* | (2006.01) |
| *A61F 2/30* | (2006.01) |
| *A61F 2/46* | (2006.01) |

(52) U.S. Cl.
CPC ........ *A61F 2/4465* (2013.01); *A61F 2/30749* (2013.01); *A61F 2/30771* (2013.01);
(Continued)

(58) Field of Classification Search
CPC ............................................ A61F 2/4455–447
(Continued)

(56) References Cited

U.S. PATENT DOCUMENTS

| | | |
|---|---|---|
| 1,673,630 A | 6/1928 | Madge |
| 2,363,405 A | 11/1944 | Eichelberger |

(Continued)

FOREIGN PATENT DOCUMENTS

| | | |
|---|---|---|
| FR | 2727003 A1 | 5/1996 |
| JP | 2006513752 A | 4/2006 |

(Continued)

OTHER PUBLICATIONS

U.S. Appl. No. 60/777,663, filed Feb. 27, 2006, Messerli.
(Continued)

*Primary Examiner* — Eduardo C Robert
*Assistant Examiner* — Christina Negrellirodriguez

(57) ABSTRACT

The present application generally relates to orthopedic systems, and in particular, to systems including independent plates and spacers. A plating system can include a spacer and a plate that is independent from the spacer. A number of locking mechanisms can be provided to secure the plate to the spacer. In some cases, the spacer includes a pair of notches that extend on an outer surface of the spacer. The plate can include a pair of lateral extensions that can engage the notches to secure the plate to the spacer. In other cases, the spacer includes an opening including a pair of inlets. The plate can include an enclosed posterior extension that can be received in the pair of inlets to secure the plate to the spacer.

19 Claims, 58 Drawing Sheets

Related U.S. Application Data continuation of application No. 16/033,277, filed on Jul. 12, 2018, now Pat. No. 10,881,526, which is a continuation-in-part of application No. 15/278,481, filed on Sep. 28, 2016, now Pat. No. 10,098,760, which is a continuation-in-part of application No. 14/727,035, filed on Jun. 1, 2015, now Pat. No. 9,681,959, and a continuation-in-part of application No. 14/476,439, filed on Sep. 3, 2014, now Pat. No. 9,980,824, said application No. 14/727,035 is a continuation-in-part of application No. 14/341,035, filed on Jul. 25, 2014, now Pat. No. 10,245,155, which is a continuation-in-part of application No. 14/320,200, filed on Jun. 30, 2014, now Pat. No. 9,848,994, which is a continuation-in-part of application No. 14/190,948, filed on Feb. 26, 2014, now Pat. No. 9,237,957, which is a continuation-in-part of application No. 14/085,318, filed on Nov. 20, 2013, now Pat. No. 9,398,960, which is a continuation-in-part of application No. 13/785,856, filed on Mar. 5, 2013, now Pat. No. 9,204,975, said application No. 14/190,948 is a continuation-in-part of application No. 13/785,434, filed on Mar. 5, 2013, now Pat. No. 9,149,365, said application No. 13/785,856 is a continuation-in-part of application No. 13/559,917, filed on Jul. 27, 2012, now Pat. No. 8,961,606, which is a continuation-in-part of application No. 13/267,119, filed on Oct. 6, 2011, now Pat. No. 9,770,340.

(60) Provisional application No. 61/535,726, filed on Sep. 16, 2011.

(52) U.S. Cl.
CPC ............ *A61F 2/4455* (2013.01); *A61F 2/447* (2013.01); *A61F 2/4611* (2013.01); *A61F 2002/3008* (2013.01); *A61F 2002/30131* (2013.01); *A61F 2002/30179* (2013.01); *A61F 2002/30308* (2013.01); *A61F 2002/30383* (2013.01); *A61F 2002/30405* (2013.01); *A61F 2002/30428* (2013.01); *A61F 2002/30433* (2013.01); *A61F 2002/30471* (2013.01); *A61F 2002/305* (2013.01); *A61F 2002/30578* (2013.01); *A61F 2002/30593* (2013.01); *A61F 2002/30604* (2013.01); *A61F 2002/30677* (2013.01); *A61F 2002/30787* (2013.01); *A61F 2002/30797* (2013.01); *A61F 2002/30836* (2013.01); *A61F 2002/30841* (2013.01); *A61F 2002/30845* (2013.01); *A61F 2002/30884* (2013.01); *A61F 2002/30904* (2013.01); *A61F 2002/4615* (2013.01); *A61F 2002/4627* (2013.01); *A61F 2002/4629* (2013.01); *A61F 2310/00023* (2013.01); *A61F 2310/00359* (2013.01); *A61F 2310/00407* (2013.01); *A61F 2310/00796* (2013.01)

(58) Field of Classification Search
USPC ............................................. 623/17.11–17.16
See application file for complete search history.

(56) References Cited

U.S. PATENT DOCUMENTS

| | | |
|---|---|---|
| 2,596,957 A | 5/1952 | Olson |
| 4,599,086 A | 7/1986 | Doty |
| 4,743,256 A | 5/1988 | Brantigan |
| 4,955,908 A | 9/1990 | Frey |
| 5,002,576 A | 3/1991 | Fuhrmann |
| 5,163,949 A | 11/1992 | Bonutti |
| 5,163,960 A | 11/1992 | Bonutti |
| 5,197,971 A | 3/1993 | Bonutti |
| 5,269,785 A | 12/1993 | Bonutti |
| 5,295,994 A | 3/1994 | Bonutti |
| 5,329,846 A | 7/1994 | Bonutti |
| 5,331,975 A | 7/1994 | Bonutti |
| 5,345,927 A | 9/1994 | Bonutti |
| 5,364,399 A | 11/1994 | Lowery |
| 5,397,364 A | 3/1995 | Kozak et al. |
| 5,403,317 A | 4/1995 | Bonutti |
| 5,403,348 A | 4/1995 | Bonutti |
| 5,441,538 A | 8/1995 | Bonutti |
| 5,454,365 A | 10/1995 | Bonutti |
| 5,458,641 A | 10/1995 | Jiminez |
| 5,464,426 A | 11/1995 | Bonutti |
| 5,496,348 A | 3/1996 | Bonutti |
| 5,514,153 A | 5/1996 | Bonutti |
| 5,514,180 A | 5/1996 | Heggeness |
| 5,522,846 A | 6/1996 | Bonutti |
| 5,527,343 A | 6/1996 | Bonutti |
| 5,534,012 A | 7/1996 | Bonutti |
| 5,545,222 A | 8/1996 | Bonutti |
| 5,549,612 A | 8/1996 | Yapp et al. |
| 5,549,630 A | 8/1996 | Bonutti |
| 5,549,631 A | 8/1996 | Bonutti |
| 5,569,305 A | 10/1996 | Bonutti |
| 5,577,517 A | 11/1996 | Bonutti |
| 5,584,862 A | 12/1996 | Bonutti |
| 5,593,425 A | 1/1997 | Bonutti |
| 5,609,635 A | 3/1997 | Michelson |
| 5,624,462 A | 4/1997 | Bonutti |
| 5,662,710 A | 9/1997 | Bonutti |
| 5,667,520 A | 9/1997 | Bonutti |
| 5,685,826 A | 11/1997 | Bonutti |
| 5,694,951 A | 12/1997 | Bonutti |
| 5,707,390 A | 1/1998 | Bonutti |
| 5,716,325 A | 2/1998 | Bonutti |
| 5,728,159 A | 3/1998 | Stroever |
| 5,733,306 A | 3/1998 | Bonutti |
| 5,735,875 A | 4/1998 | Bonutti |
| 5,741,253 A | 4/1998 | Michelson |
| 5,814,084 A | 9/1998 | Grivas |
| 5,827,318 A | 10/1998 | Bonutti |
| 5,845,645 A | 12/1998 | Bonutti |
| 5,860,997 A | 1/1999 | Bonutti |
| 5,861,041 A | 1/1999 | Tienboon |
| 5,888,196 A | 3/1999 | Bonutti |
| 5,888,219 A | 3/1999 | Bonutti |
| 5,888,223 A | 3/1999 | Bray, Jr. |
| 5,888,227 A | 3/1999 | Cottle |
| 5,899,939 A | 5/1999 | Boyce |
| 5,928,267 A | 7/1999 | Bonutti |
| 5,935,131 A | 8/1999 | Bonutti |
| 5,941,900 A | 8/1999 | Bonutti |
| 5,954,739 A | 9/1999 | Bonutti |
| 5,972,368 A | 10/1999 | Mckay |
| 5,989,289 A | 11/1999 | Coates |
| 6,010,525 A | 1/2000 | Bonutti |
| 6,017,305 A | 1/2000 | Bonutti |
| 6,025,538 A | 2/2000 | Yaccarino, III |
| 6,033,438 A | 3/2000 | Bianchi |
| 6,042,596 A | 3/2000 | Bonutti |
| 6,045,579 A | 4/2000 | Hochshuler |
| 6,059,817 A | 5/2000 | Bonutti |
| 6,066,175 A | 5/2000 | Henderson et al. |
| 6,077,292 A | 6/2000 | Bonutti |
| 6,086,593 A | 7/2000 | Bonutti |
| 6,096,081 A | 8/2000 | Grivas |
| 6,099,531 A | 8/2000 | Bonutti |
| 6,102,928 A | 8/2000 | Bonutti |
| 6,132,472 A | 10/2000 | Bonutti |
| RE36,974 E | 11/2000 | Bonutti |
| 6,143,033 A | 11/2000 | Paul |
| 6,146,421 A | 11/2000 | Gordon |
| 6,156,037 A | 12/2000 | LeHuec et al. |
| 6,159,234 A | 12/2000 | Bonutti |
| 6,171,236 B1 | 1/2001 | Bonutti |

(56) References Cited

U.S. PATENT DOCUMENTS

| | | |
|---|---|---|
| 6,171,299 B1 | 1/2001 | Bonutti |
| 6,174,311 B1 | 1/2001 | Branch |
| 6,174,313 B1 | 1/2001 | Bonutti |
| 6,187,023 B1 | 2/2001 | Bonutti |
| 6,200,347 B1 | 3/2001 | Anderson et al. |
| 6,203,565 B1 | 3/2001 | Bonutti |
| 6,206,922 B1 | 3/2001 | Zdeblick et al. |
| 6,206,923 B1 | 3/2001 | Boyd |
| 6,217,617 B1 | 4/2001 | Bonutti |
| 6,231,592 B1 | 5/2001 | Bonutti |
| 6,231,610 B1 | 5/2001 | Geisler |
| 6,235,059 B1 | 5/2001 | Benezech |
| 6,245,108 B1 | 6/2001 | Biscup |
| 6,258,089 B1 | 7/2001 | Campbell et al. |
| 6,258,125 B1 | 7/2001 | Paul |
| 6,261,586 B1 | 7/2001 | Mckay |
| 6,270,528 B1 | 8/2001 | Mckay |
| 6,277,136 B1 | 8/2001 | Bonutti |
| 6,287,325 B1 | 9/2001 | Bonutti |
| 6,294,187 B1 | 9/2001 | Boyce |
| 6,342,074 B1 | 1/2002 | Simpson |
| 6,350,283 B1 | 2/2002 | Michelson |
| 6,358,266 B1 | 3/2002 | Bonutti |
| 6,361,565 B1 | 3/2002 | Bonutti |
| 6,364,880 B1 | 4/2002 | Michelson |
| 6,368,343 B1 | 4/2002 | Bonutti |
| 6,371,988 B1 | 4/2002 | Pafford |
| 6,379,385 B1 | 4/2002 | Kalas |
| 6,383,186 B1 | 5/2002 | Michelson |
| 6,398,811 B1 | 6/2002 | Mckay |
| 6,409,765 B1 | 6/2002 | Bianchi |
| 6,432,106 B1 | 8/2002 | Fraser |
| 6,432,436 B1 | 8/2002 | Gertzman |
| 6,447,516 B1 | 9/2002 | Bonutti |
| 6,451,042 B1 | 9/2002 | Bonutti |
| 6,458,158 B1 | 10/2002 | Anderson |
| 6,464,713 B2 | 10/2002 | Bonutti |
| 6,468,289 B1 | 10/2002 | Bonutti |
| 6,468,293 B2 | 10/2002 | Bonutti |
| 6,468,311 B2 | 10/2002 | Boyd |
| 6,471,724 B2 | 10/2002 | Zdeblick |
| 6,475,230 B1 | 11/2002 | Bonutti |
| 6,482,233 B1 | 11/2002 | Aebi |
| 6,500,195 B2 | 12/2002 | Bonutti |
| 6,503,267 B2 | 1/2003 | Bonutti |
| 6,503,277 B2 | 1/2003 | Bonutti |
| 6,511,509 B1 | 1/2003 | Ford |
| 6,520,993 B2 | 2/2003 | James |
| 6,540,785 B1 | 4/2003 | Gill et al. |
| 6,543,455 B2 | 4/2003 | Bonutti |
| 6,548,080 B1 | 4/2003 | Gertzman |
| 6,554,863 B2 | 4/2003 | Paul |
| 6,558,387 B2 | 5/2003 | Errico |
| 6,558,423 B1 | 5/2003 | Michelson |
| 6,558,424 B2 | 5/2003 | Thalgott |
| 6,562,073 B2 | 5/2003 | Foley |
| 6,569,187 B1 | 5/2003 | Bonutti |
| 6,575,982 B1 | 6/2003 | Bonutti |
| 6,579,318 B2 | 6/2003 | Varga |
| 6,585,750 B2 | 7/2003 | Bonutti |
| 6,592,531 B2 | 7/2003 | Bonutti |
| 6,592,609 B1 | 7/2003 | Bonutti |
| 6,607,534 B2 | 8/2003 | Bonutti |
| 6,610,065 B1 | 8/2003 | Branch |
| 6,620,181 B1 | 9/2003 | Bonutti |
| 6,629,998 B1 | 10/2003 | Lin |
| 6,630,000 B1 | 10/2003 | Bonutti |
| 6,632,247 B2 | 10/2003 | Boyer, II |
| 6,635,073 B2 | 10/2003 | Bonutti |
| 6,638,309 B2 | 10/2003 | Bonutti |
| 6,638,310 B2 | 10/2003 | Lin |
| 6,652,532 B2 | 11/2003 | Bonutti |
| 6,652,593 B2 | 11/2003 | Boyer, II |
| 6,660,038 B2 | 12/2003 | Boyer, II |
| 6,666,889 B1 | 12/2003 | Commarmond |
| 6,666,890 B2 | 12/2003 | Michelson |
| 6,676,703 B2 | 1/2004 | Biscup |
| 6,682,563 B2 | 1/2004 | Scharf |
| 6,695,882 B2 | 2/2004 | Bianchi |
| 6,702,821 B2 | 3/2004 | Bonutti |
| 6,702,856 B2 | 3/2004 | Bonutti |
| 6,706,067 B2 | 3/2004 | Shimp |
| 6,709,458 B2 | 3/2004 | Michelson |
| 6,719,794 B2 | 4/2004 | Gerber |
| 6,719,803 B2 | 4/2004 | Bonutti |
| 6,730,127 B2 | 5/2004 | Michelson |
| 6,736,853 B2 | 5/2004 | Bonutti |
| 6,740,118 B2 | 5/2004 | Eisermann et al. |
| 6,761,738 B1 | 7/2004 | Boyd |
| 6,761,739 B2 | 7/2004 | Shepard |
| 6,764,491 B2 | 7/2004 | Frey |
| 6,767,369 B2 | 7/2004 | Boyer, II |
| 6,770,078 B2 | 8/2004 | Bonutti |
| 6,776,800 B2 | 8/2004 | Boyer, II |
| 6,776,938 B2 | 8/2004 | Bonutti |
| 6,793,658 B2 | 9/2004 | LeHuec |
| RE38,614 E | 10/2004 | Paul |
| 6,805,714 B2 | 10/2004 | Sutcliffe |
| 6,808,585 B2 | 10/2004 | Boyce |
| 6,827,740 B1 | 12/2004 | Michelson |
| 6,830,570 B1 | 12/2004 | Frey |
| 6,835,198 B2 | 12/2004 | Bonutti |
| 6,835,206 B2 | 12/2004 | Jackson |
| 6,849,093 B2 | 2/2005 | Michelson |
| 6,852,126 B2 | 2/2005 | Ahlgren |
| 6,855,167 B2 | 2/2005 | Shimp |
| 6,855,169 B2 | 2/2005 | Boyer, II |
| 6,860,885 B2 | 3/2005 | Bonutti |
| 6,860,904 B2 | 3/2005 | Bonutti |
| 6,887,272 B2 | 4/2005 | Shinomiya |
| 6,899,735 B2 | 5/2005 | Coates et al. |
| 6,902,578 B1 | 6/2005 | Anderson |
| 6,905,517 B2 | 6/2005 | Bonutti |
| 6,908,466 B1 | 6/2005 | Bonutti |
| 6,929,662 B1 | 8/2005 | Messerli |
| 6,932,835 B2 | 8/2005 | Bonutti |
| 6,972,019 B2 | 12/2005 | Michelson |
| 6,974,480 B2 | 12/2005 | Messerli |
| 6,986,788 B2 | 1/2006 | Paul |
| 6,989,029 B2 | 1/2006 | Bonutti |
| 6,990,982 B1 | 1/2006 | Bonutti |
| 7,001,432 B2 | 2/2006 | Keller et al. |
| 7,014,659 B2 | 3/2006 | Boyer, II |
| 7,018,412 B2 | 3/2006 | Ferreira |
| 7,018,413 B2 | 3/2006 | Krüger |
| 7,022,137 B2 | 4/2006 | Michelson |
| 7,025,787 B2 | 4/2006 | Bryan et al. |
| 7,044,968 B1 | 5/2006 | Yaccarino, III |
| 7,044,972 B2 | 5/2006 | Mathys |
| 7,048,755 B2 | 5/2006 | Bonutti |
| 7,048,762 B1 | 5/2006 | Sander |
| 7,048,765 B1 | 5/2006 | Grooms |
| 7,060,073 B2 | 6/2006 | Frey |
| 7,060,096 B1 | 6/2006 | Schopf |
| 7,070,557 B2 | 7/2006 | Bonutti |
| 7,087,073 B2 | 8/2006 | Bonutti |
| 7,087,082 B2 | 8/2006 | Paul |
| 7,087,087 B2 | 8/2006 | Boyer, II |
| 7,094,251 B2 | 8/2006 | Bonutti |
| 7,104,996 B2 | 9/2006 | Bonutti |
| 7,112,222 B2 | 9/2006 | Fraser |
| 7,114,500 B2 | 10/2006 | Bonutti |
| 7,115,146 B2 | 10/2006 | Boyer, II |
| 7,128,753 B1 | 10/2006 | Bonutti |
| 7,134,437 B2 | 11/2006 | Bonutti |
| 7,137,997 B2 | 11/2006 | Paul |
| 7,147,652 B2 | 12/2006 | Bonutti |
| 7,147,665 B1 | 12/2006 | Bryan et al. |
| 7,153,325 B2 | 12/2006 | Kim et al. |
| 7,163,561 B2 | 1/2007 | Michelson |
| 7,172,627 B2 | 2/2007 | Fiere et al. |
| 7,192,447 B2 | 3/2007 | Rhoda |
| 7,208,013 B1 | 4/2007 | Bonutti |
| 7,217,273 B2 | 5/2007 | Bonutti |

(56) References Cited

U.S. PATENT DOCUMENTS

| | | |
|---|---|---|
| 7,217,290 B2 | 5/2007 | Bonutti |
| 7,223,292 B2 | 5/2007 | Messerli |
| 7,226,482 B2 | 6/2007 | Messerli |
| 7,226,483 B2 | 6/2007 | Gerber |
| 7,229,477 B2 | 6/2007 | Biscup |
| 7,232,464 B2 | 6/2007 | Mathieu et al. |
| 7,238,203 B2 | 7/2007 | Bagga |
| 7,276,082 B2 | 10/2007 | Zdeblick et al. |
| 7,300,465 B2 | 11/2007 | Paul |
| 7,309,357 B2 | 12/2007 | Kim |
| 7,309,359 B2 | 12/2007 | Trieu |
| 7,311,719 B2 | 12/2007 | Bonutti |
| 7,320,708 B1 | 1/2008 | Bernstein |
| 7,323,011 B2 | 1/2008 | Shepard |
| 7,329,263 B2 | 2/2008 | Bonutti |
| 7,347,873 B2 | 3/2008 | Paul |
| 7,429,266 B2 | 9/2008 | Bonutti |
| 7,435,262 B2 | 10/2008 | Michelson |
| 7,462,200 B2 | 12/2008 | Bonutti |
| 7,473,277 B2 | 1/2009 | Boyer, II |
| 7,479,160 B2 | 1/2009 | Branch |
| 7,481,812 B2 | 1/2009 | Frey |
| 7,481,831 B2 | 1/2009 | Bonutti |
| 7,491,237 B2 | 2/2009 | Randall |
| 7,510,557 B1 | 3/2009 | Bonutti |
| 7,594,931 B2 | 9/2009 | Louis |
| 7,601,173 B2 | 10/2009 | Messerli |
| 7,615,054 B1 | 11/2009 | Bonutti |
| 7,618,456 B2 | 11/2009 | Mathieu et al. |
| 7,618,460 B2 | 11/2009 | Boyd |
| 7,635,390 B1 | 12/2009 | Bonutti |
| 7,637,953 B2 | 12/2009 | Branch |
| 7,662,184 B2 | 2/2010 | Edwards |
| 7,662,185 B2 | 2/2010 | Alfaro |
| 7,708,740 B1 | 5/2010 | Bonutti |
| 7,708,741 B1 | 5/2010 | Bonutti |
| 7,726,002 B2 | 6/2010 | Shimp |
| 7,727,283 B2 | 6/2010 | Bonutti |
| 7,749,229 B1 | 7/2010 | Bonutti |
| 7,753,963 B2 | 7/2010 | Boyer, II |
| 7,771,475 B2 | 8/2010 | Michelson |
| 7,780,670 B2 | 8/2010 | Bonutti |
| 7,794,502 B2 | 9/2010 | Michelson |
| 7,806,896 B1 | 10/2010 | Bonutti |
| 7,806,897 B1 | 10/2010 | Bonutti |
| 7,815,682 B1 | 10/2010 | Peterson |
| 7,828,852 B2 | 11/2010 | Bonutti |
| 7,833,271 B2 | 11/2010 | Mitchell |
| 7,837,736 B2 | 11/2010 | Bonutti |
| 7,846,207 B2 | 12/2010 | Lechmann et al. |
| 7,850,731 B2 | 12/2010 | Brittan |
| 7,854,750 B2 | 12/2010 | Bonutti |
| 7,862,616 B2 | 1/2011 | Lechmann et al. |
| 7,875,076 B2 | 1/2011 | Mathieu et al. |
| 7,879,103 B2 | 1/2011 | Gertzman |
| 7,879,072 B2 | 2/2011 | Bonutti |
| 7,892,236 B1 | 2/2011 | Bonutti |
| 7,892,261 B2 | 2/2011 | Bonutti |
| 7,896,880 B2 | 3/2011 | Bonutti |
| 7,918,888 B2 | 4/2011 | Hamada |
| 7,931,690 B1 | 4/2011 | Bonutti |
| 7,931,692 B2 | 4/2011 | Sybert |
| 7,938,857 B2 | 5/2011 | Garcia-bengochea |
| 7,959,635 B1 | 6/2011 | Bonutti |
| 7,967,867 B2 | 6/2011 | Barreiro |
| 7,972,381 B2 | 7/2011 | Michelson |
| 8,002,833 B2 | 8/2011 | Fabris Monterumici |
| 8,100,976 B2 | 1/2012 | Bray et al. |
| 8,105,383 B2 | 1/2012 | Michelson |
| 8,114,162 B1 | 2/2012 | Bradley |
| 8,128,669 B2 | 3/2012 | Bonutti |
| 8,133,229 B1 | 3/2012 | Bonutti |
| 8,162,977 B2 | 4/2012 | Bonutti |
| 8,273,127 B2 | 9/2012 | Jones |
| 8,323,343 B2 | 12/2012 | Michelson |
| 8,328,872 B2 | 12/2012 | Duffield |
| 8,343,222 B2 | 1/2013 | Cope |
| 8,366,776 B2 | 2/2013 | Heinz |
| 8,425,522 B2 | 4/2013 | Bonutti |
| 8,435,300 B2 | 5/2013 | Messerli |
| 8,486,066 B2 | 7/2013 | Bonutti |
| 8,623,030 B2 | 1/2014 | Bonutti |
| 8,632,552 B2 | 1/2014 | Bonutti |
| 8,641,726 B2 | 2/2014 | Bonutti |
| 8,690,944 B2 | 4/2014 | Bonutti |
| 8,709,085 B2 | 4/2014 | Lechmann |
| 8,739,797 B2 | 6/2014 | Bonutti |
| 8,747,439 B2 | 6/2014 | Bonutti |
| 8,784,495 B2 | 7/2014 | Bonutti |
| 8,795,363 B2 | 8/2014 | Bonutti |
| 8,814,902 B2 | 8/2014 | Bonutti |
| 8,834,490 B2 | 9/2014 | Bonutti |
| 8,840,629 B2 | 9/2014 | Bonutti |
| 8,845,699 B2 | 9/2014 | Bonutti |
| 8,858,557 B2 | 10/2014 | Bonutti |
| 8,932,358 B1 * | 1/2015 | Nehls ............... A61F 2/4455 623/17.16 |
| 8,956,417 B2 | 2/2015 | Bonutti |
| 9,044,322 B2 | 6/2015 | Bonutti |
| 9,044,341 B2 | 6/2015 | Bonutti |
| 9,050,152 B2 | 6/2015 | Bonutti |
| 10,245,155 B2 * | 4/2019 | Petersheim ............ A61F 2/447 |
| 2001/0010021 A1 | 7/2001 | Boyd |
| 2001/0023371 A1 | 9/2001 | Bonutti |
| 2002/0010511 A1 | 1/2002 | Michelson |
| 2002/0016595 A1 | 2/2002 | Michelson |
| 2002/0029055 A1 | 3/2002 | Bonutti |
| 2002/0040246 A1 | 4/2002 | Bonutti |
| 2002/0095160 A1 | 7/2002 | Bonutti |
| 2002/0106393 A1 | 8/2002 | Bianchi |
| 2002/0138143 A1 | 9/2002 | Grooms |
| 2003/0009147 A1 | 1/2003 | Bonutti |
| 2003/0023260 A1 | 1/2003 | Bonutti |
| 2003/0045939 A1 | 3/2003 | Casutt |
| 2003/0105528 A1 | 6/2003 | Shimp et al. |
| 2003/0125739 A1 | 7/2003 | Bagga et al. |
| 2003/0167091 A1 | 9/2003 | Scharf |
| 2004/0010287 A1 | 1/2004 | Bonutti |
| 2004/0078078 A1 | 4/2004 | Shepard |
| 2004/0097794 A1 | 5/2004 | Bonutti |
| 2004/0098016 A1 | 5/2004 | Bonutti |
| 2004/0138689 A1 | 7/2004 | Bonutti |
| 2004/0138690 A1 | 7/2004 | Bonutti |
| 2004/0143270 A1 | 7/2004 | Zucherman et al. |
| 2004/0143285 A1 | 7/2004 | Bonutti |
| 2004/0143332 A1 | 7/2004 | Krueger et al. |
| 2004/0172033 A1 | 9/2004 | Bonutti |
| 2004/0172133 A1 | 9/2004 | Gerber |
| 2004/0176853 A1 | 9/2004 | Sennett et al. |
| 2004/0193181 A1 | 9/2004 | Bonutti |
| 2004/0230223 A1 | 11/2004 | Bonutti |
| 2005/0055098 A1 | 3/2005 | Zdeblick et al. |
| 2005/0065607 A1 | 3/2005 | Gross |
| 2005/0149192 A1 | 7/2005 | Zucherman et al. |
| 2005/0149193 A1 | 7/2005 | Zucherman et al. |
| 2005/0159819 A1 | 7/2005 | McCormack et al. |
| 2005/0171607 A1 | 8/2005 | Michelson |
| 2005/0177236 A1 | 8/2005 | Mathieu et al. |
| 2005/0187625 A1 | 8/2005 | Wolek et al. |
| 2005/0216059 A1 | 9/2005 | Bonutti |
| 2005/0240267 A1 | 10/2005 | Randall et al. |
| 2005/0240271 A1 | 10/2005 | Zubok et al. |
| 2005/0256574 A1 | 11/2005 | Paul et al. |
| 2005/0267534 A1 | 12/2005 | Bonutti |
| 2006/0085071 A1 | 4/2006 | Lechmann et al. |
| 2006/0129240 A1 | 6/2006 | Lessar et al. |
| 2006/0142828 A1 | 6/2006 | Schorr |
| 2006/0167495 A1 | 7/2006 | Bonutti |
| 2006/0217809 A1 | 9/2006 | Albert et al. |
| 2006/0235470 A1 | 10/2006 | Bonutti |
| 2006/0241760 A1 | 10/2006 | Randall |
| 2006/0265009 A1 | 11/2006 | Bonutti |
| 2007/0088441 A1 | 4/2007 | Duggal et al. |
| 2007/0123987 A1 | 5/2007 | Bernstein |

(56) References Cited

U.S. PATENT DOCUMENTS

| | | |
|---|---|---|
| 2007/0135923 A1 | 6/2007 | Peterman et al. |
| 2007/0162130 A1 | 7/2007 | Rashbaum et al. |
| 2007/0168032 A1 | 7/2007 | Muhanna et al. |
| 2007/0208378 A1 | 9/2007 | Bonutti |
| 2007/0225806 A1 | 9/2007 | Squires et al. |
| 2007/0225812 A1 | 9/2007 | Gill |
| 2007/0233253 A1 | 10/2007 | Bray et al. |
| 2007/0250167 A1 | 10/2007 | Bray et al. |
| 2007/0255414 A1 | 11/2007 | Melkent |
| 2007/0270961 A1 | 11/2007 | Ferguson |
| 2008/0039873 A1 | 2/2008 | Bonutti |
| 2008/0046090 A1 | 2/2008 | Paul |
| 2008/0047567 A1 | 2/2008 | Bonutti |
| 2008/0051890 A1 | 2/2008 | Waugh et al. |
| 2008/0051907 A1 | 2/2008 | Marik |
| 2008/0058822 A1 | 3/2008 | Bonutti |
| 2008/0065140 A1 | 3/2008 | Bonutti |
| 2008/0103519 A1 | 5/2008 | Bonutti |
| 2008/0108916 A1 | 5/2008 | Bonutti |
| 2008/0114399 A1 | 5/2008 | Bonutti |
| 2008/0125865 A1 | 5/2008 | Abdelgany |
| 2008/0133013 A1 | 6/2008 | Duggal et al. |
| 2008/0140011 A1 | 6/2008 | Bonutti |
| 2008/0140117 A1 | 6/2008 | Bonutti |
| 2008/0154379 A1 | 6/2008 | Steiner |
| 2008/0188940 A1 | 8/2008 | Cohen |
| 2008/0249569 A1 | 10/2008 | Waugh |
| 2009/0076608 A1 | 3/2009 | Gordon et al. |
| 2009/0099661 A1 | 4/2009 | Bhattacharya |
| 2009/0101582 A1 | 4/2009 | Liu |
| 2009/0210062 A1 | 8/2009 | Thalgott et al. |
| 2010/0057206 A1 | 3/2010 | Duffield et al. |
| 2010/0145459 A1 | 6/2010 | McDonough |
| 2010/0145460 A1 | 6/2010 | McDonough |
| 2010/0305704 A1 | 12/2010 | Messerli |
| 2011/0087327 A1 | 4/2011 | Lechmann |
| 2011/0160864 A1 | 6/2011 | Messerli |
| 2011/0202136 A1 | 8/2011 | Brittan et al. |
| 2011/0251689 A1* | 10/2011 | Seifert .................. A61F 2/4465 623/17.16 |
| 2012/0010623 A1 | 1/2012 | Bonutti |
| 2012/0078373 A1 | 3/2012 | Gamache |
| 2012/0130495 A1 | 5/2012 | Duffield |
| 2012/0130496 A1 | 5/2012 | Duffield |
| 2012/0197401 A1 | 8/2012 | Duncan et al. |
| 2012/0215226 A1 | 8/2012 | Bonutti |
| 2012/0215233 A1 | 8/2012 | Bonutti |
| 2012/0221017 A1 | 8/2012 | Bonutti |
| 2012/0277872 A1 | 11/2012 | Kana et al. |
| 2012/0277873 A1 | 11/2012 | Kana et al. |
| 2012/0323330 A1 | 12/2012 | Kueenzi |
| 2013/0073047 A1 | 3/2013 | Laskowitz |
| 2013/0211523 A1 | 8/2013 | Southard |
| 2013/0226185 A1 | 8/2013 | Bonutti |
| 2013/0237989 A1 | 9/2013 | Bonutti |
| 2013/0274810 A1 | 10/2013 | Fraser et al. |
| 2013/0289729 A1 | 10/2013 | Bonutti |
| 2014/0012380 A1 | 1/2014 | Laurence et al. |
| 2014/0018854 A1 | 1/2014 | Bonutti |
| 2014/0025110 A1 | 1/2014 | Bonutti |
| 2014/0025111 A1 | 1/2014 | Bonutti |
| 2014/0025112 A1 | 1/2014 | Bonutti |
| 2014/0039623 A1 | 2/2014 | Tott et al. |
| 2014/0180422 A1 | 6/2014 | Klimek et al. |
| 2014/0228963 A1 | 8/2014 | Bonutti |
| 2014/0257380 A1 | 9/2014 | Bonutti |
| 2014/0309560 A1 | 10/2014 | Bonutti |
| 2014/0343573 A1 | 11/2014 | Bonutti |

FOREIGN PATENT DOCUMENTS

| | | |
|---|---|---|
| JP | 2012501744 A | 1/2012 |
| JP | 2012508043 A | 4/2012 |
| WO | 1997023175 A1 | 7/1997 |
| WO | 1999063914 A1 | 12/1999 |
| WO | 03032812 A2 | 4/2003 |
| WO | 2005007040 A1 | 1/2005 |
| WO | 2007098288 A2 | 8/2007 |
| WO | 2008014258 A2 | 1/2008 |

OTHER PUBLICATIONS

U.S. Appl. No. 60/777,732, filed Feb. 27, 2006, Messerli et al.

U.S. Appl. No. 60/838,229, filed Aug. 16, 2006, Hunziker et al.

Guidance Document: Intervertebral Body Fusion Device, U.S. Dept. of Health and Human Services, Food and Drug Administration (Jun. 12, 2007).

M. Spruit et al., The in vitro stabilizing effect of polyetheretherketone cages versus a titanium cage of similar design for anterior lumbar interbody fusion, 14(8) Eur. Spine J. 752, 752-758 (2005).

P. Schleicher et al., Biomechanical comparison of two different concepts for stand alone anterior lumbar interbody fusion, 17(12) Eur. Spine J. 1757, 1757-1765 (2008).

P.W. Pavlov et al., Anterior lumbar interbody fusion with threaded fusion cages and autologous bone grafts, 9 Eur. Spine J. 224, 224-229 (2000).

Synthes' SynFix Technique Guide device ("SynFix Technique Guide").

* cited by examiner

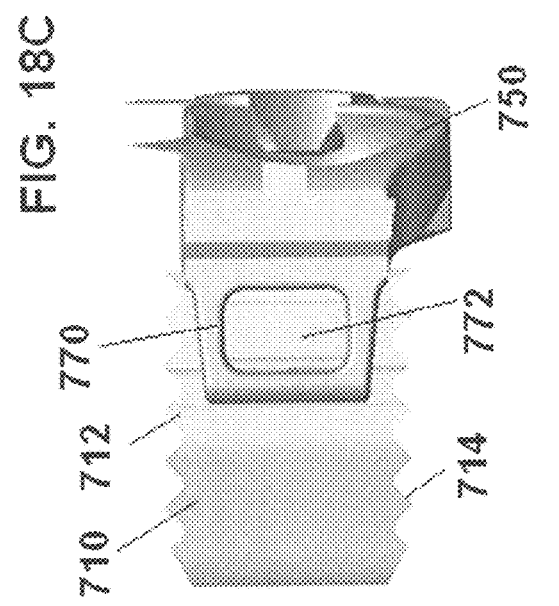

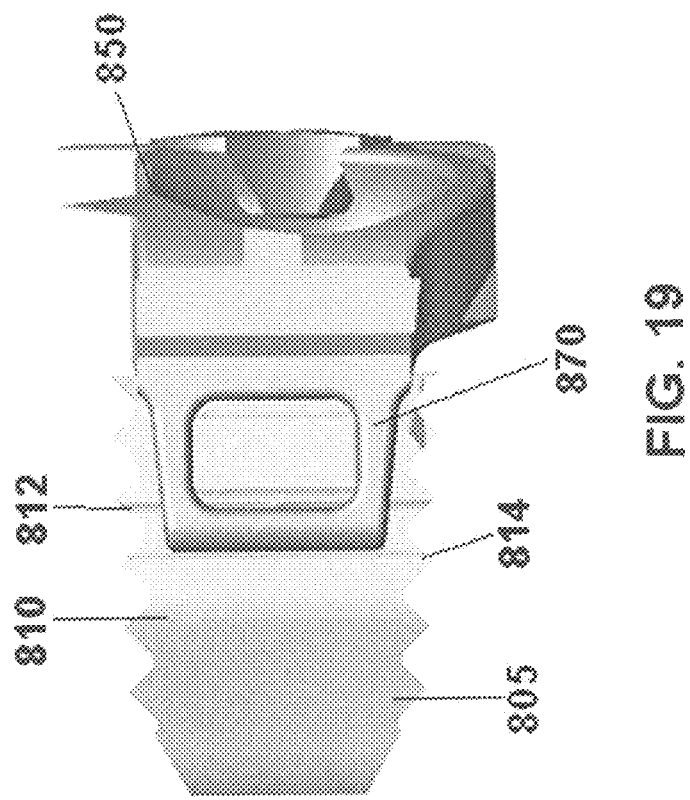

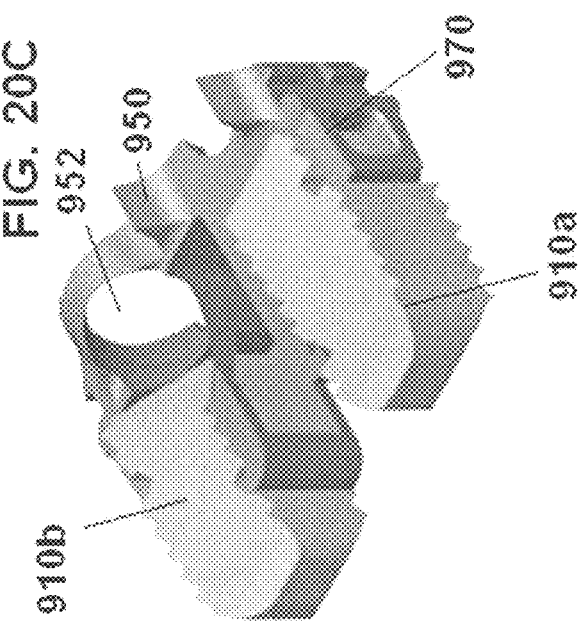
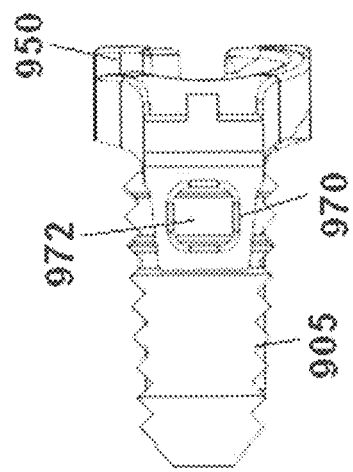
FIG. 20C
FIG. 20D
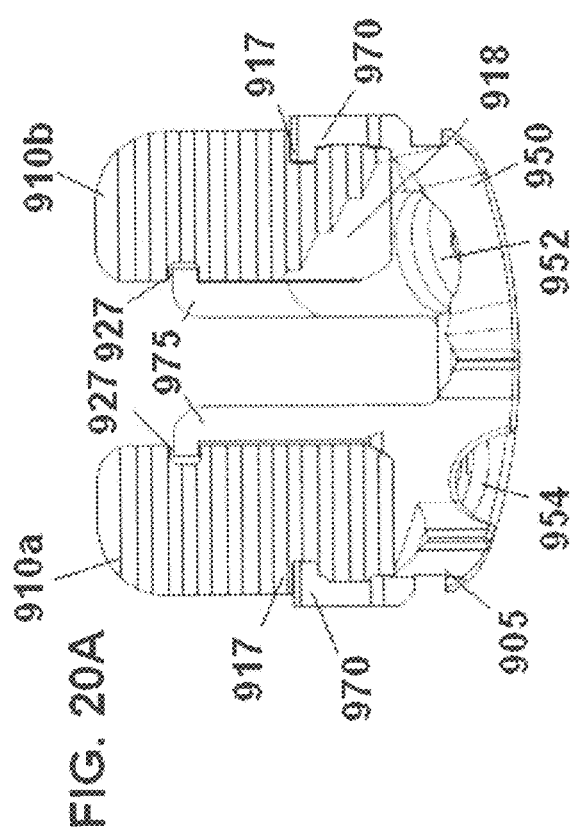
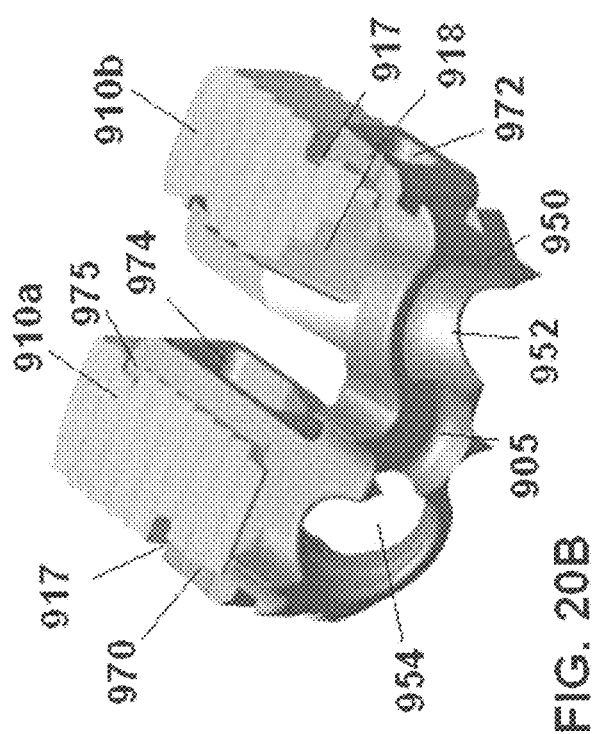
FIG. 20A
FIG. 20B

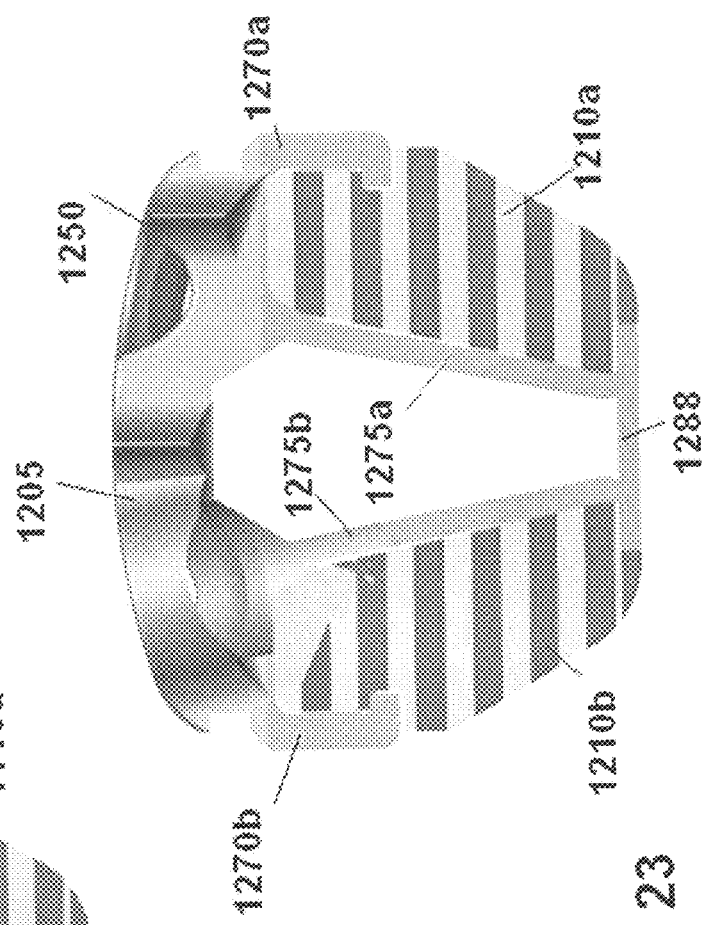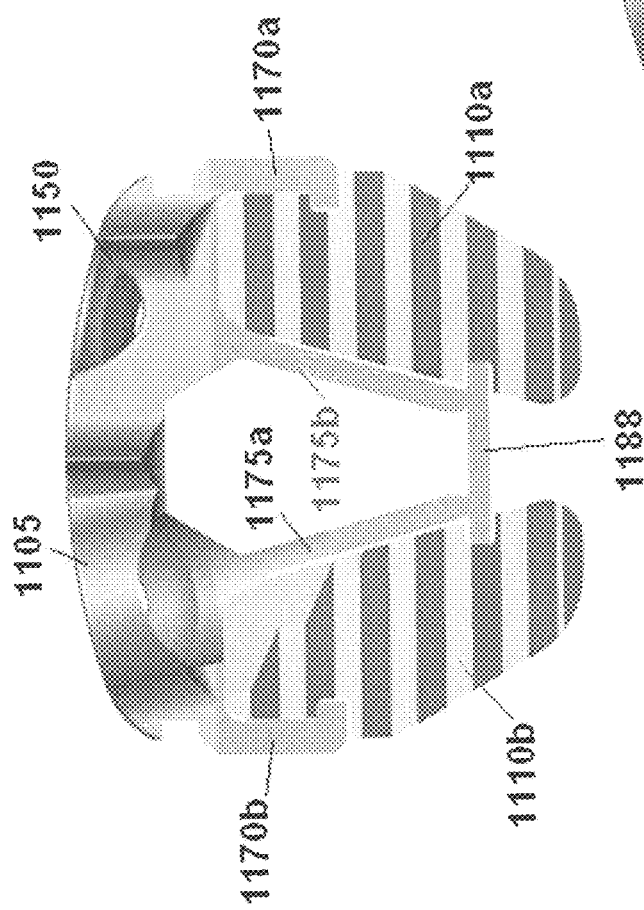

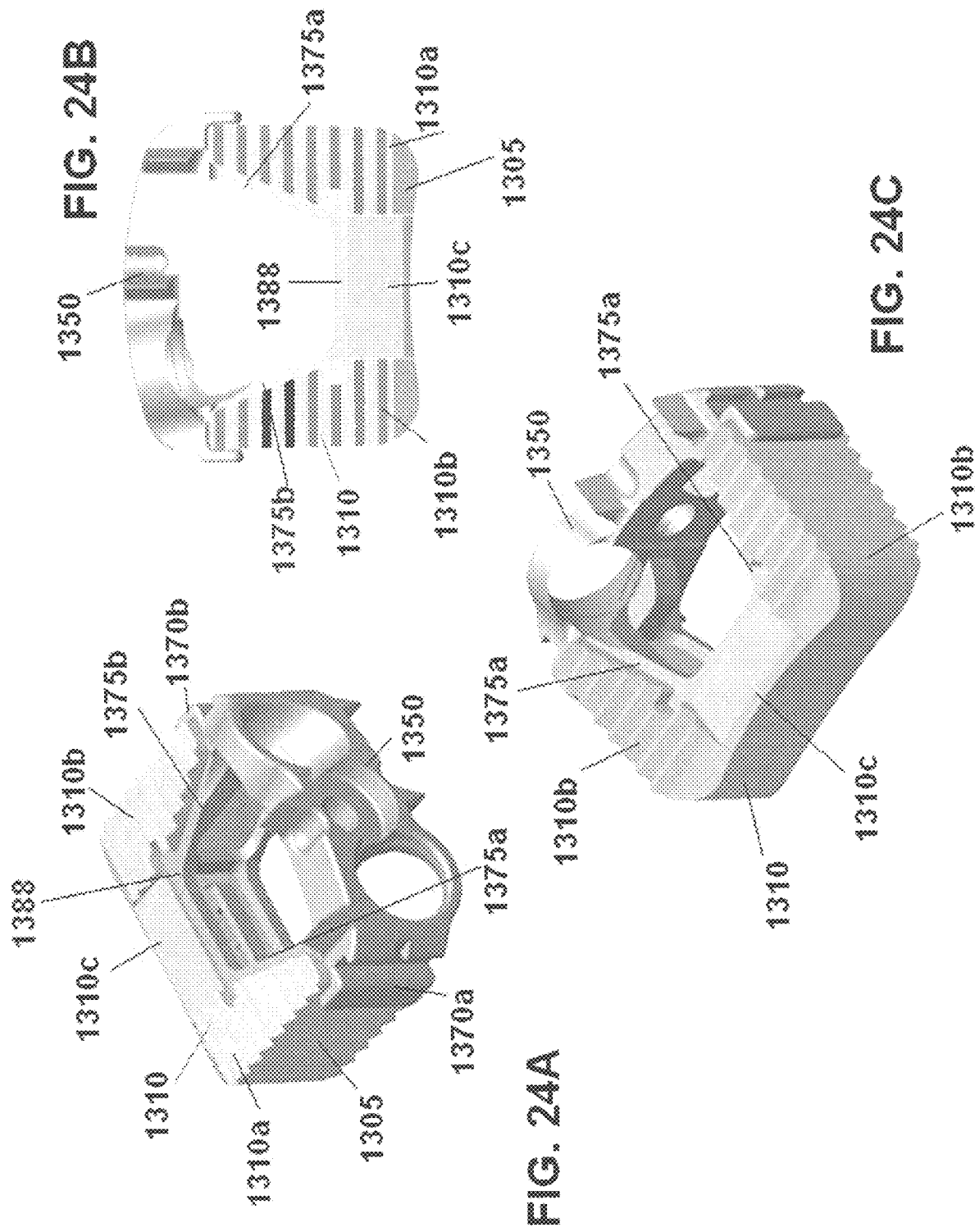

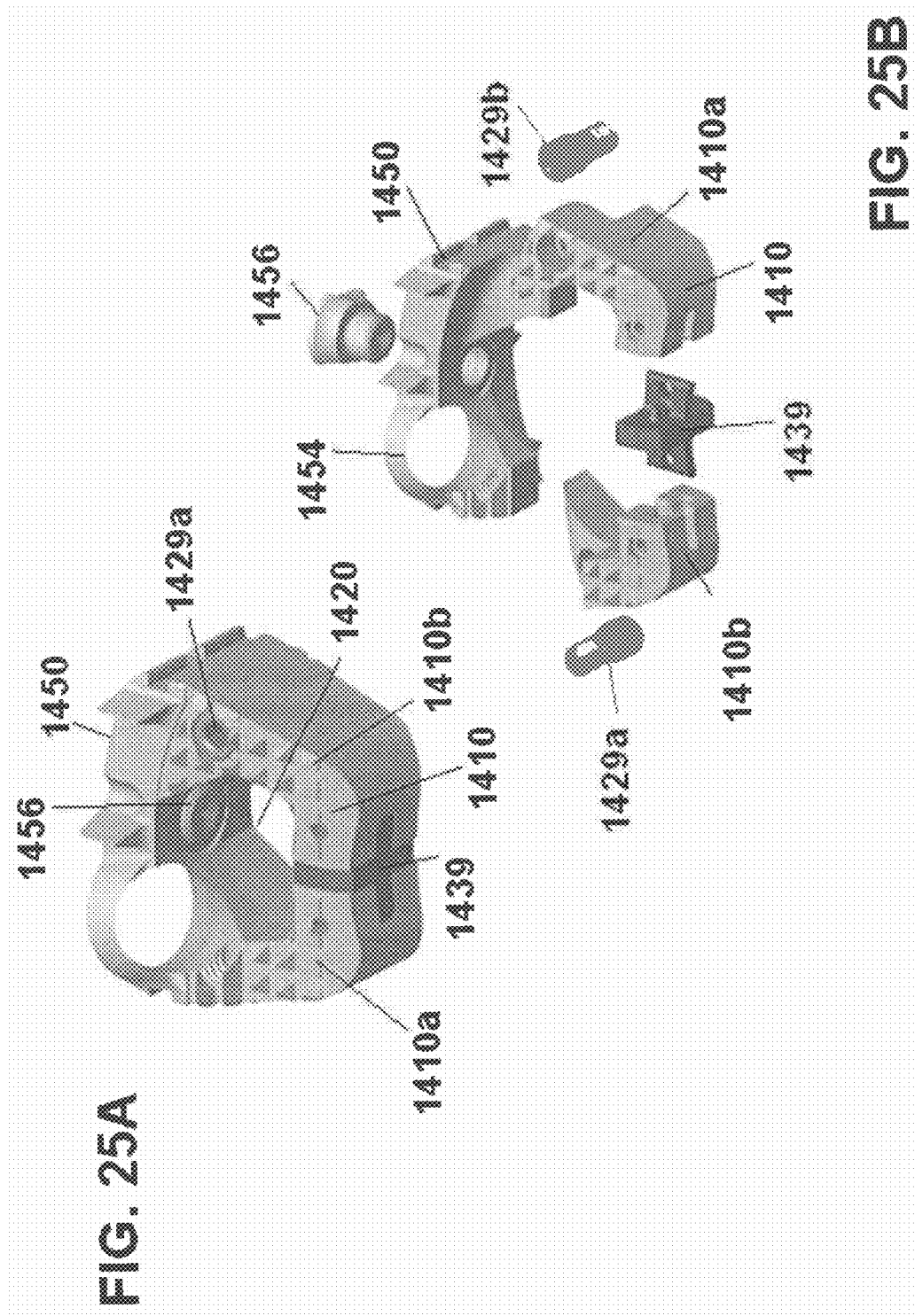

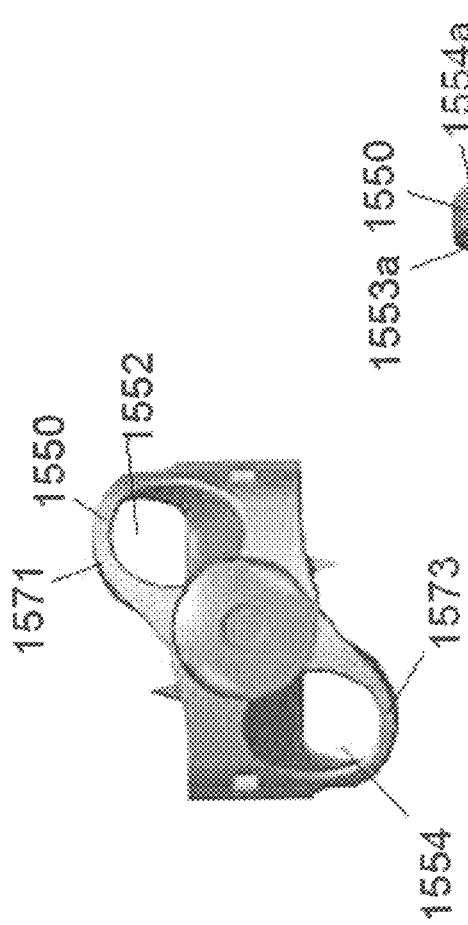
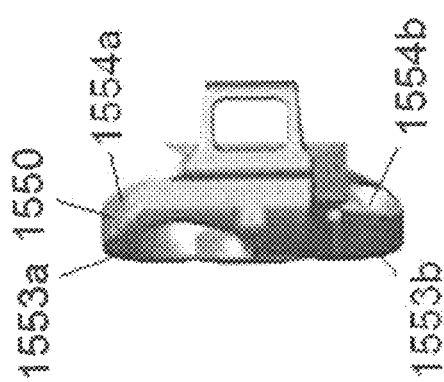
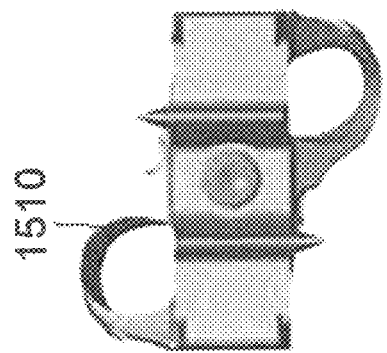

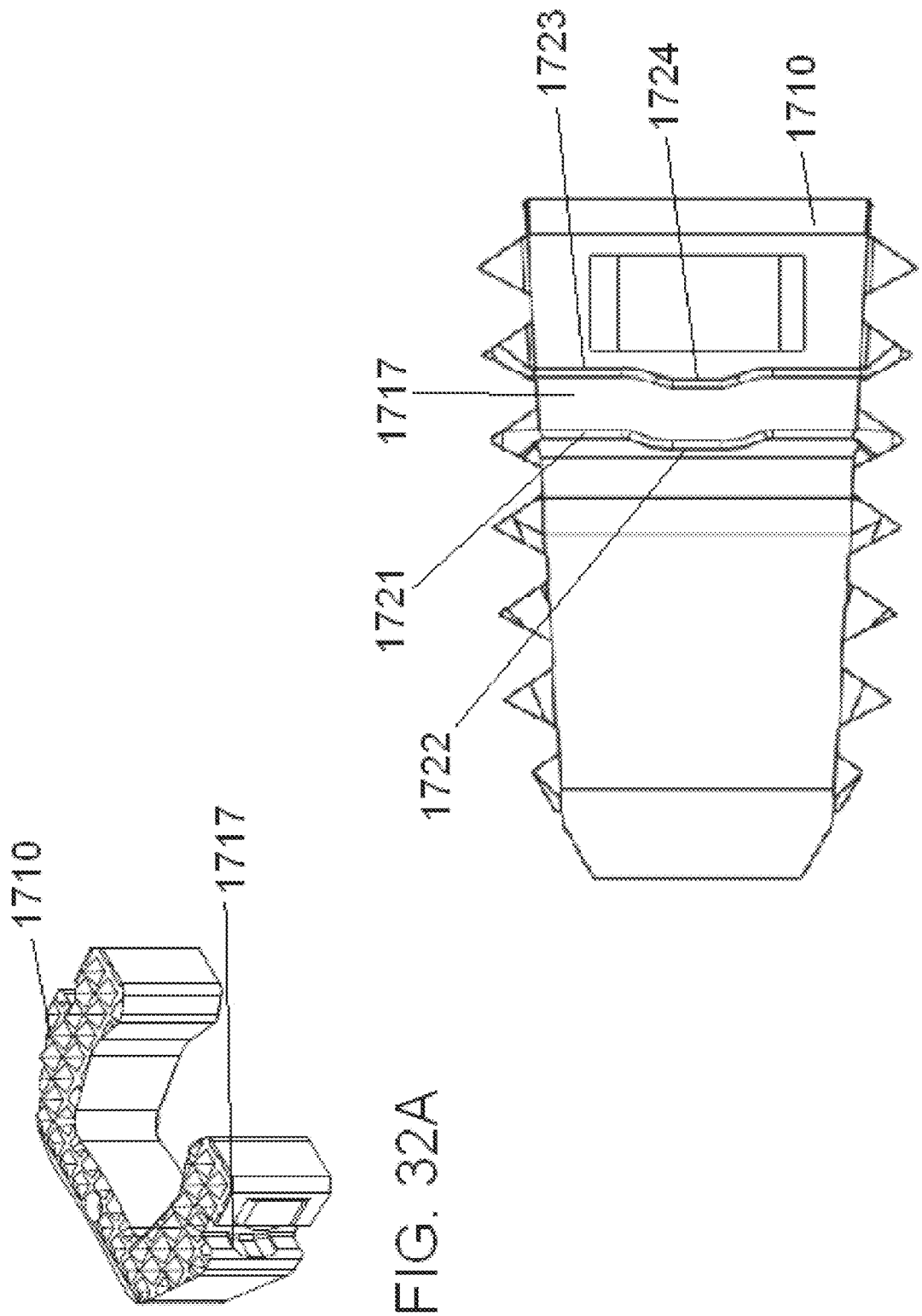

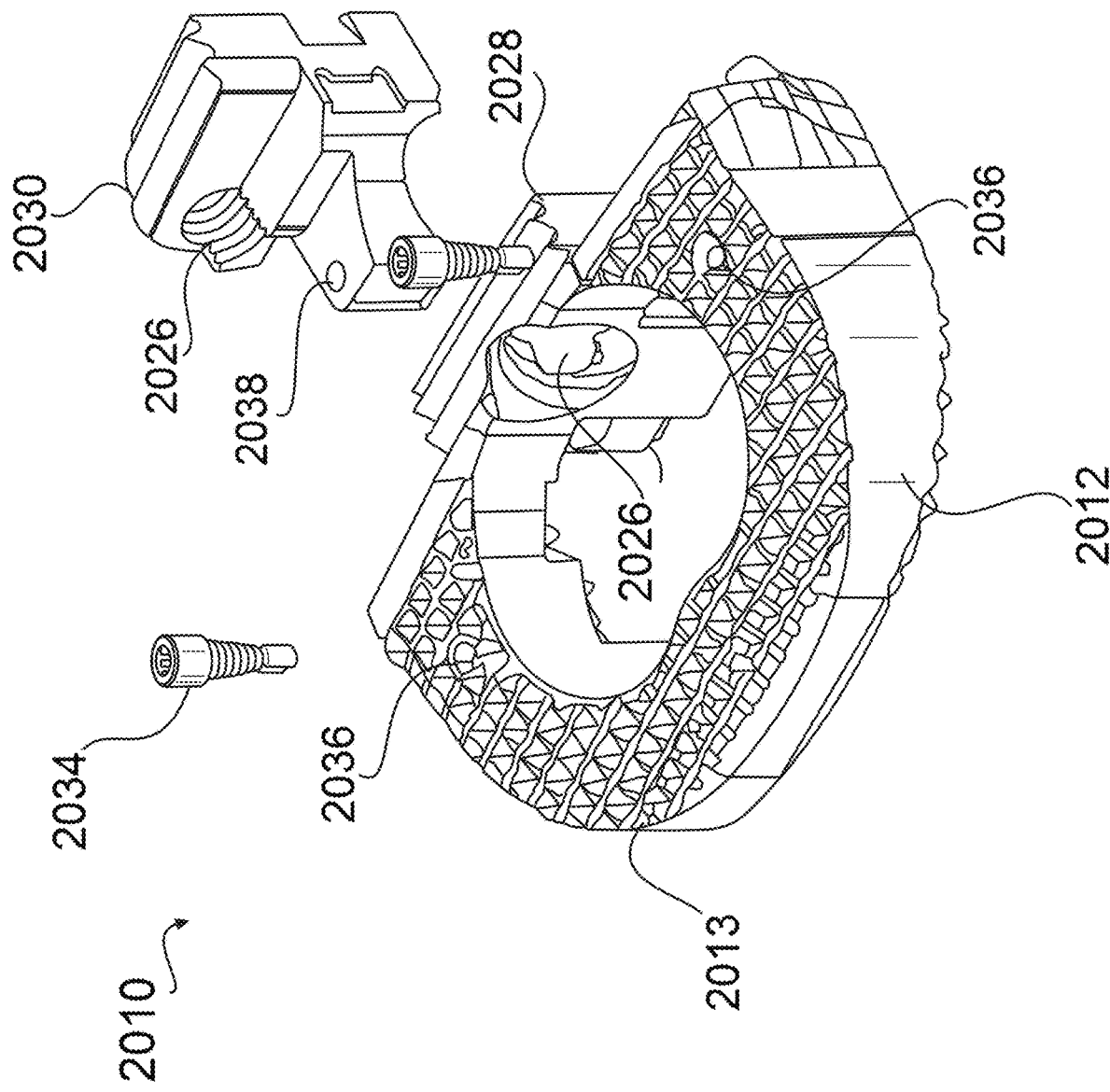
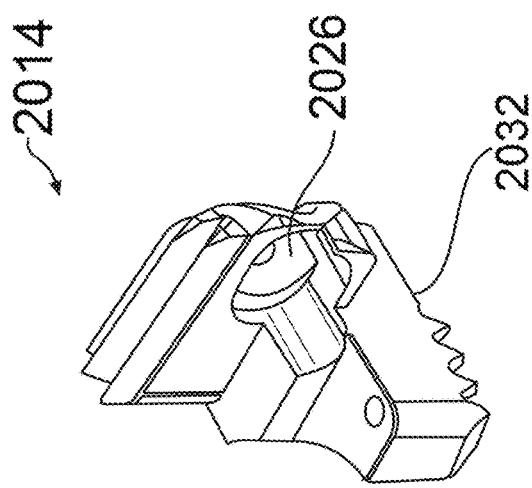
FIG. 34

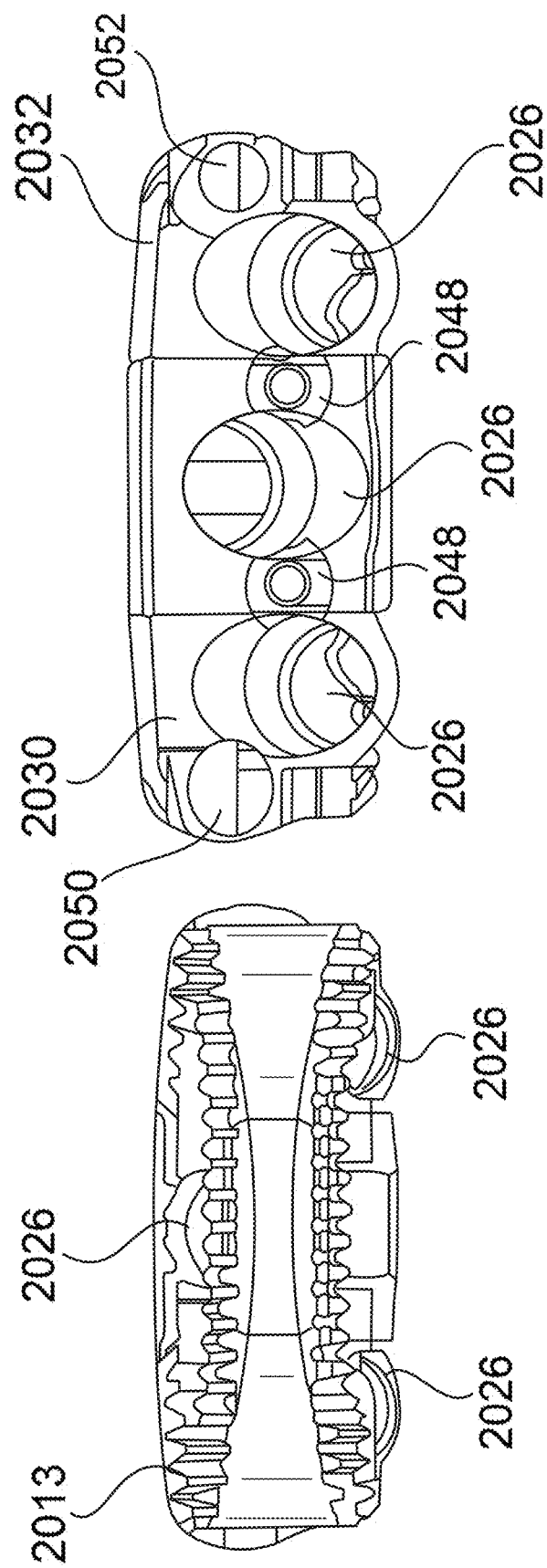

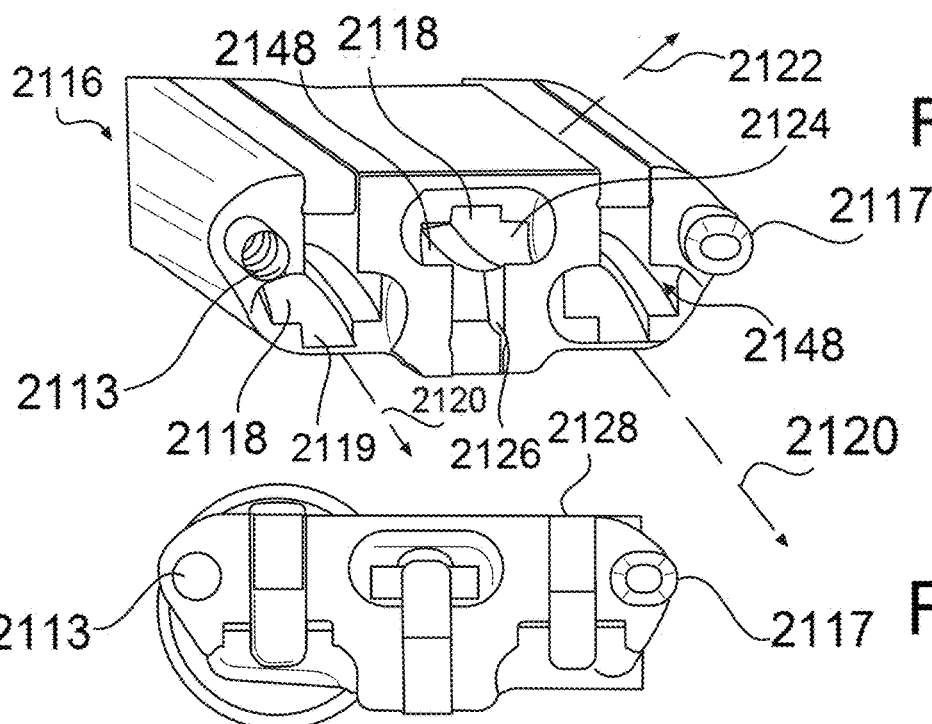
FIG. 43
FIG. 44
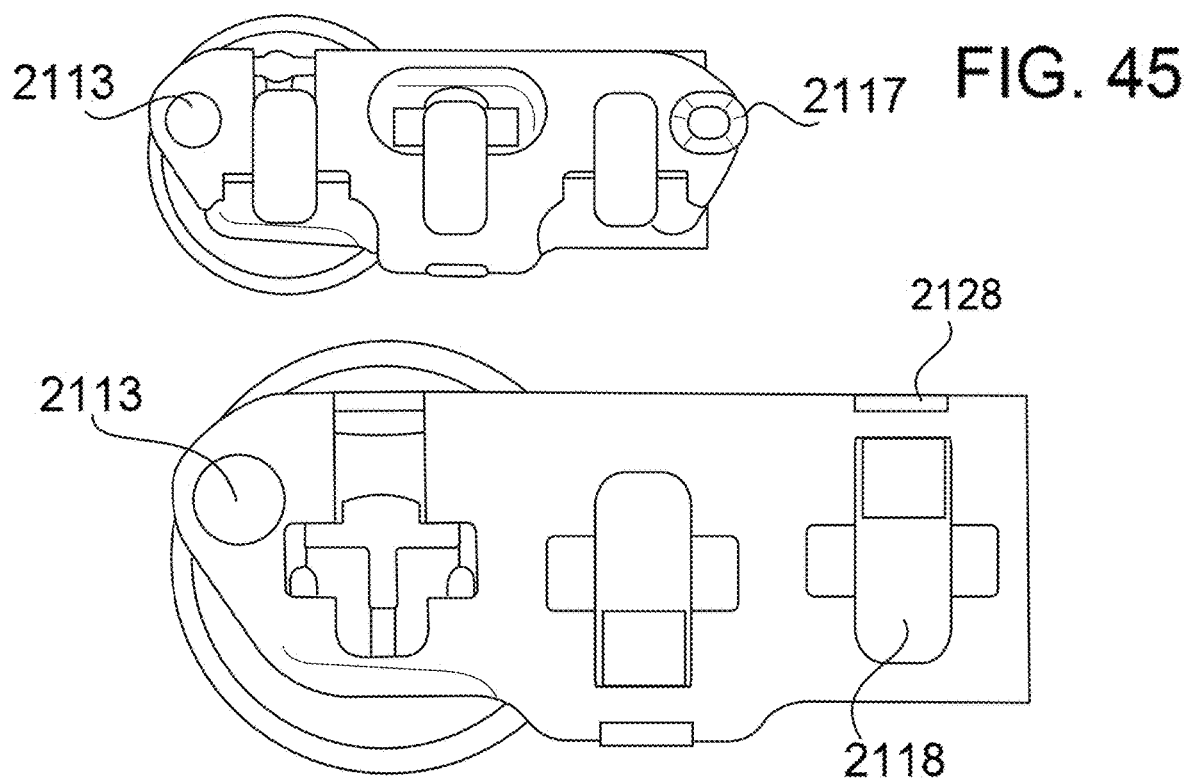
FIG. 45
FIG. 46

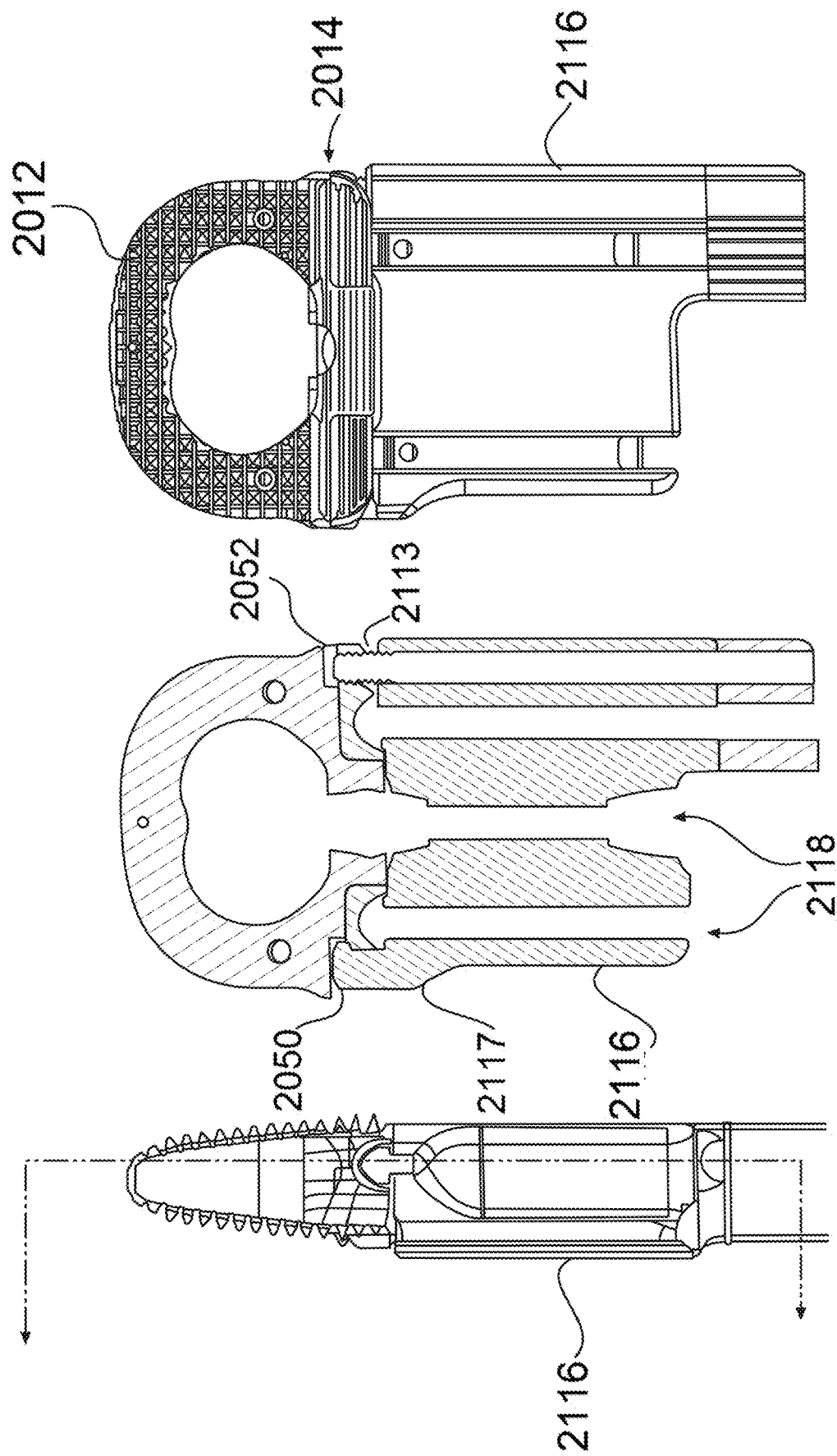

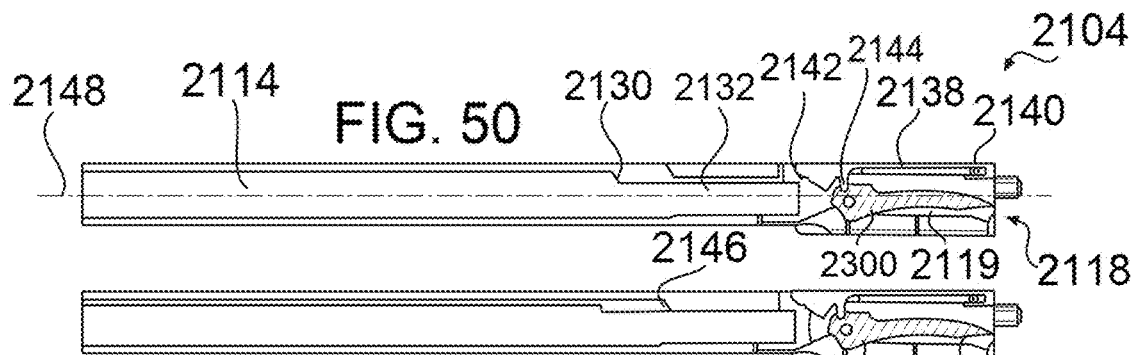
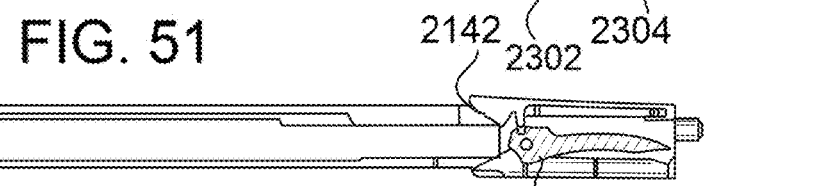
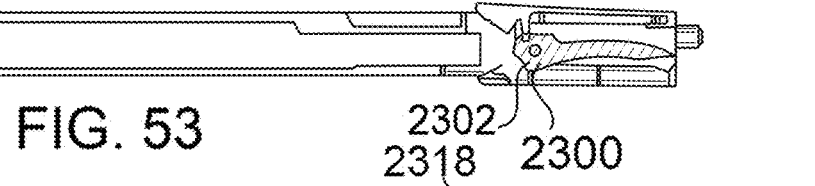
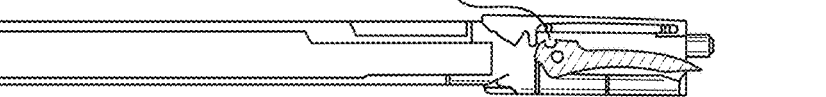
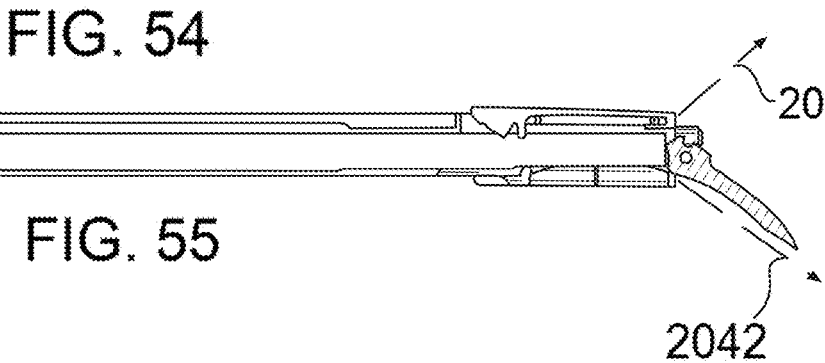

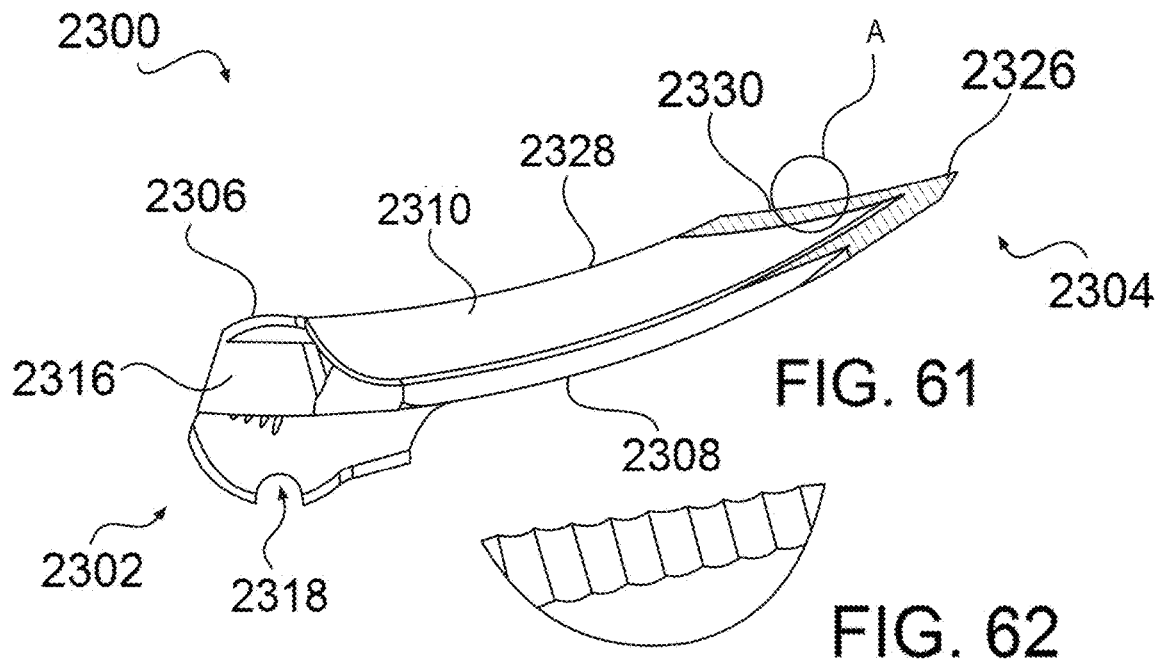
FIG. 61
FIG. 62
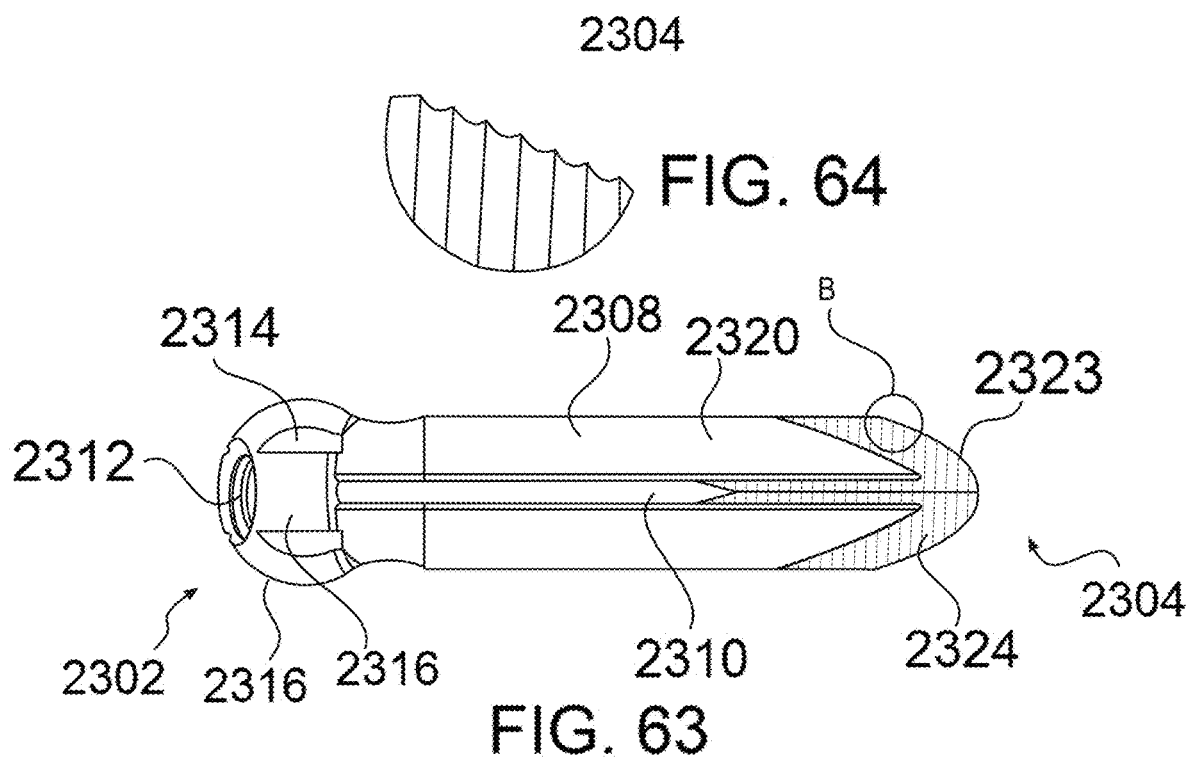
FIG. 64
FIG. 63

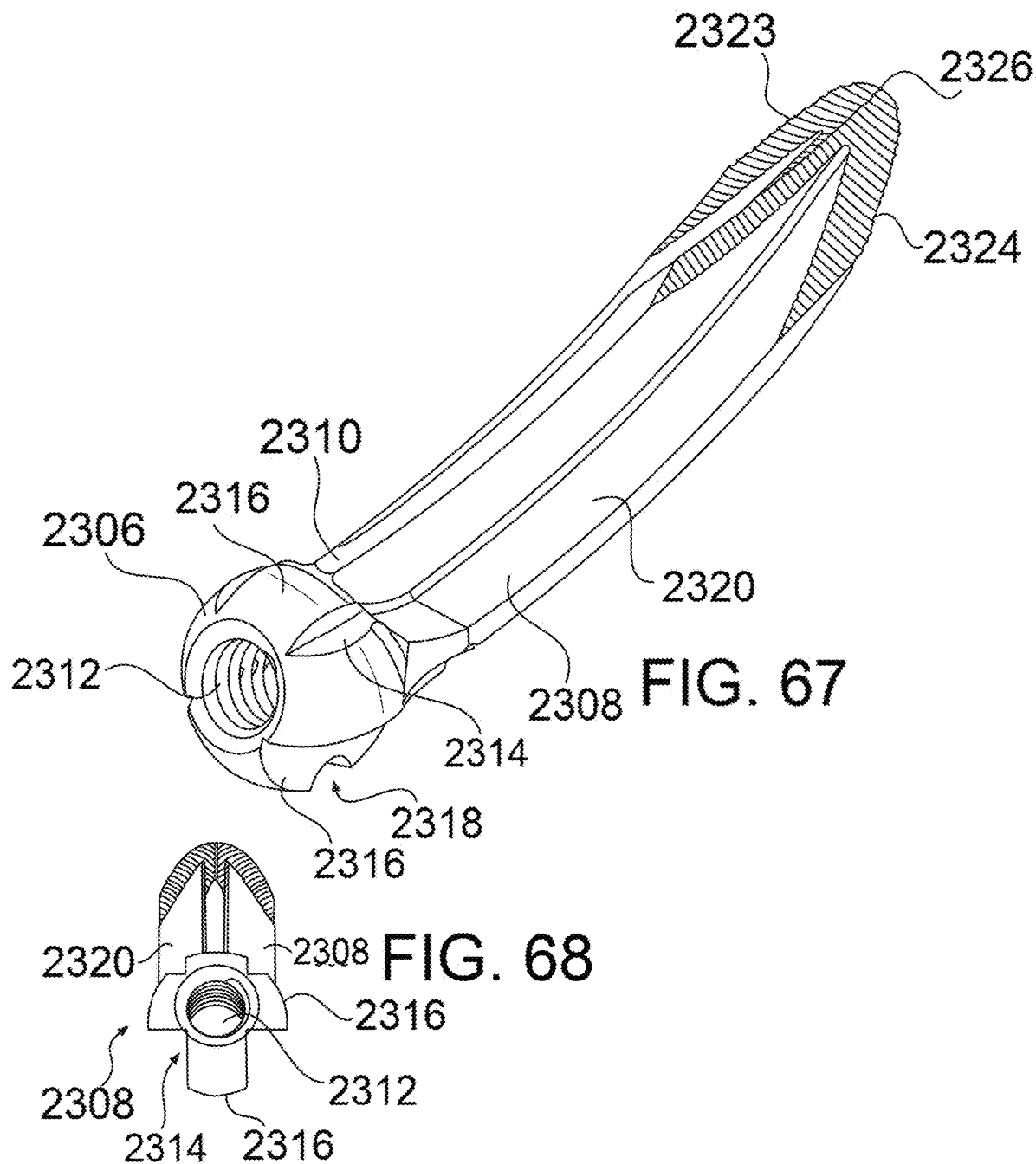

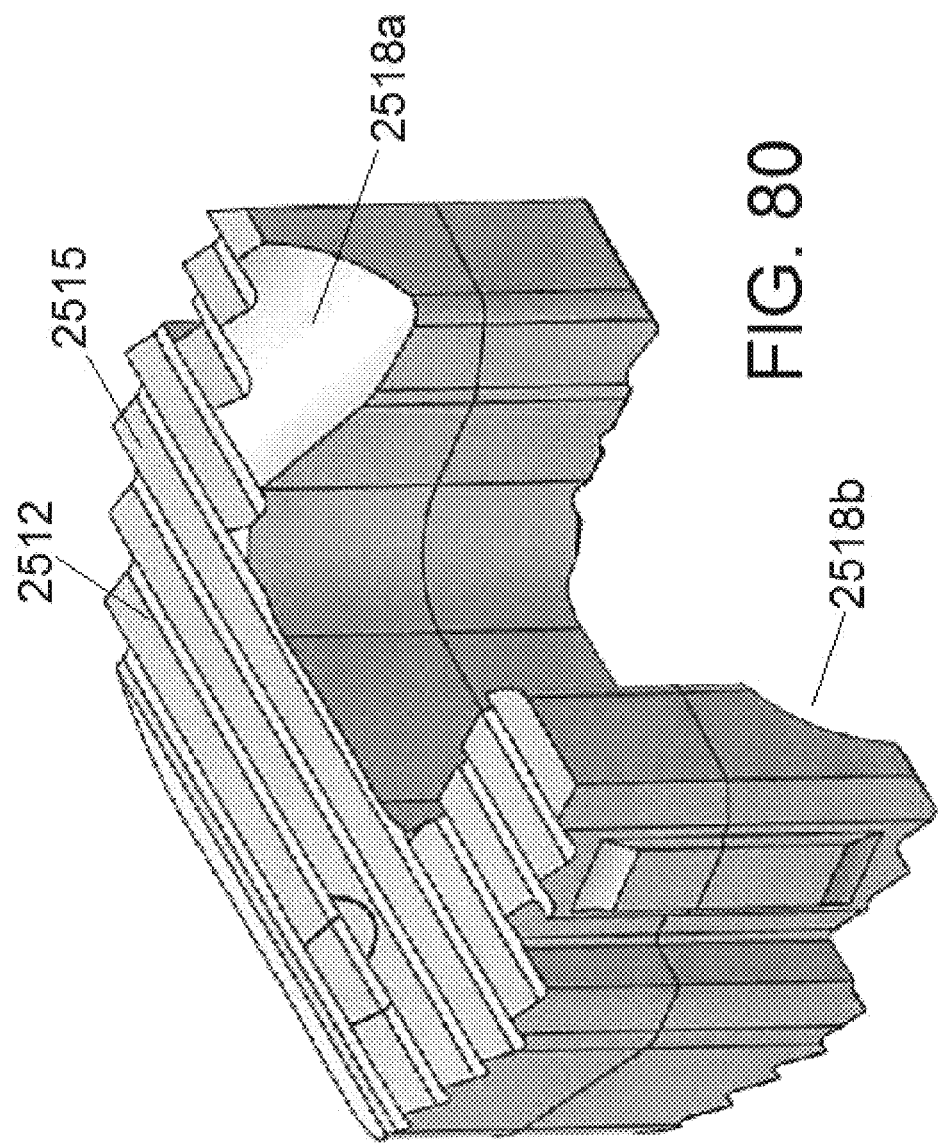

LOW PROFILE PLATE

CROSS-REFERENCE TO RELATED APPLICATIONS

The present application is a continuation of U.S. application Ser. No. 17/140,358 which is a continuation of U.S. application Ser. No. 16/033,277 filed Jul. 12, 2018, which is a continuation-in-part of U.S. Ser. No. 15/278,481 filed Sep. 28, 2016, which is (i) a continuation-in-part application of U.S. Ser. No. 14/476,439, filed Sep. 3, 2014 and (ii) a continuation-in-part application of U.S. Ser. No. 14/727,035, filed Jun. 1, 2015, which is a continuation-in-part application of U.S. application Ser. No. 14/341,035, filed Jul. 25, 2014, which is a continuation-in-part application of U.S. Ser. No. 14/320,200, filed Jun. 30, 2014, which is a continuation-in-part application of U.S. Ser. No. 14/190,948, filed Feb. 26, 2014, now issued as U.S. Pat. No. 9,237,957, which is a continuation-in-part application of (i) U.S. Ser. No. 13/785,434, filed Mar. 5, 2013, now issued as U.S. Pat. No. 9,149,365, and of (ii) U.S. Ser. No. 14/085,318, filed Nov. 20, 2013, now issued as U.S. Pat. No. 9,398,960, which is a continuation-in-part application of U.S. patent application Ser. No. 13/785,856, filed Mar. 5, 2013, now issued as U.S. Pat. No. 9,204,975, which is a continuation-in-part of U.S. patent application Ser. No. 13/559,917, filed Jul. 27, 2012, now issued as U.S. Pat. No. 8,961,606, which is a continuation-in-part of Ser. No. 13/267,119, filed Oct. 6, 2011, which claims priority to U.S. Provisional Application 61/535,726, filed on Sep. 16, 2011, the entire of contents of each of the references are incorporated by reference herein in their entirety.

FIELD OF THE INVENTION

The present application is generally directed to orthopedic systems, and in particular, to systems including plates and spacers.

BACKGROUND

Spinal discs and/or vertebral bodies of a spine can be displaced or damaged due to trauma, disease, degenerative defects, or wear over an extended period of time. One result of this displacement or damage may be chronic back pain. In some cases, to alleviate back pain, the disc can be removed and replaced with an implant, such as a spacer, that promotes fusion. In addition to providing one or more spacers, a plating system can be used to further stabilize the spine during the fusion process. Such a plating system can include one or more plates and screws for aligning and holding vertebrae in a fixed position with respect to one another.

Accordingly, there is a need for improved systems involving plating systems and spacers for spinal fusion and stabilization.

SUMMARY OF THE INVENTION

Various systems, devices and methods related to plating systems are provided. In some embodiments, a spinal system comprises a spacer for inserting into an intervertebral space and a plate configured to abut the spacer. The spacer can include an upper surface, a lower surface and an opening that extends between the upper surface to the lower surface, wherein the spacer further includes a tapered leading end. The plate for abutting the spacer can include a plate body, a first opening formed in the plate body for receiving a first bone screw, a second opening formed in the plate body for receiving a second bone screw, a set screw, and a pair of extensions that extend from the plate body that are configured to engage the spacer. The first opening can angled in an upward direction, while the second opening can be angled in a downward direction. The set screw can be configured to prevent back-out of both the first and the second bone screws, wherein the set screw has a first position whereby the first and second bone screws can be inserted past the set screw and into the first and second openings and a second position following rotation of the set screw whereby the first and second bone screws are prevented from backing out by the set screw. A first bone screw is provided for inserting into the first opening in the plate body, wherein the first bone screw is configured to be inserted into a first vertebral body. A second bone screw is provided for inserting into the second opening in the plate body, wherein the second bone screw is configured to be inserted into a second vertebral body different from the vertebral body.

In other embodiments, a spinal system comprises a spacer for inserting into an intervertebral space and a plate configured to abut the spacer. The spacer can include an upper surface, a lower surface and an opening that extends between the upper surface to the lower surface, wherein the spacer further includes a concave leading end. The plate for abutting the spacer can include a plate body, a first opening formed in the plate body for receiving a first bone screw, a second opening formed in the plate body for receiving a second bone screw, a set screw, and a pair of extensions that extend from the plate body that are configured to engage the spacer. The first opening can angled in an upward direction, while the second opening can be angled in a downward direction. The set screw can be configured to prevent back-out of at least one of the first and the second bone screws, wherein the set screw has a first position whereby at least one of the first and second bone screws can be inserted past the set screw and into at least one of the first and second openings and a second position following rotation of the set screw whereby at least one of the first and second bone screws are prevented from backing out by the set screw. Each of the pair of extensions can include a window that extends along a length of the extension. A first bone screw is provided for inserting into the first opening in the plate body, wherein the first bone screw is configured to be inserted into a first vertebral body. A second bone screw is provided for inserting into the second opening in the plate body, wherein the second bone screw is configured to be inserted into a second vertebral body different from the vertebral body.

In some embodiments, a spinal system comprises a spacer for inserting into an intervertebral space and a plate configured to abut the spacer. The spacer can include an upper surface, a lower surface and an opening that extends between the upper surface to the lower surface. The plate for abutting the spacer can include a plate body, a first opening formed in the plate body for receiving a first bone screw, a second opening formed in the plate body for receiving a second bone screw, a set screw, and a pair of extensions that extend from the plate body that are configured to engage the spacer. The first opening can angled in an upward direction, while the second opening can be angled in a downward direction. The set screw can be configured to prevent back-out of at least one of the first and the second bone screws, wherein the set screw has a first position whereby at least one of the first and second bone screws can be inserted past the set screw and into at least one of the first and second openings and a second position following rotation of the set screw whereby at least one of the first and second bone screws are prevented from backing out by the set screw. Each of the pair of extensions can include a window that extends along a length of the extension. A first bone screw is provided for inserting into the first opening in the plate body, wherein the first bone screw is configured to be inserted into a first vertebral body. A second bone screw is provided for inserting into the second opening in the plate body, wherein the second bone screw is configured to be inserted into a second vertebral body different from the vertebral body. The spacer and the plate are independent from one another such that the spacer can be inserted into a desired spinal location prior to abutting the spacer with the plate.

BRIEF DESCRIPTION OF THE DRAWINGS

FIGS. 18A-18D illustrate different views of another alternative low profile plate attached to a spacer according to some embodiments.

FIG. 19 illustrates a lordotic version of the low profile plate and spacer shown in FIGS. 18A-18D.

FIGS. 20A-20D illustrate different views of another alternative low profile plate attached to multiple spacers according to some embodiments.

FIG. 22 illustrates another alternative low profile plate attached to multiple spacers according to some embodiments.

FIG. 23 illustrates another alternative low profile plate attached to multiple spacers according to some embodiments.

FIGS. 24A-24C illustrate another alternative low profile plate attached to a multi-piece spacer having three pieces according to some embodiments.

FIGS. 25A and 25B illustrate another alternative low profile plate attached to a multi-piece spacer having a metal insert according to some embodiments.

FIGS. 29A-29C illustrate the plate in FIGS. 26A-26D.

FIGS. 32A and 32B illustrate different views of a spacer having a notch having a curved channel in accordance with some embodiments.

FIGS. 33-40 illustrate various views of a vertebral spacer in accordance with a first exemplary embodiment of the present disclosure.

FIGS. 43-46 depict various end or cross-sectional views of the insertion device of FIG. 42.

FIGS. 47-49 depict the insertion device of FIG. 42 coupled with an intervertebral anchor in accordance with an example of the present disclosure.

FIGS. 50-55 depict an exemplary tool and method of installing a vertebral anchor in accordance with an example of the present disclosure.

FIG. 61 is a side view of a vertebral anchor in accordance with an example of the present disclosure.

FIG. 62 is an enlarged view of detail A in FIG. 61, illustrating a distal portion of the vertebral anchor of FIG. 29.

FIG. 63 is a top view of the vertebral anchor of FIG. 61.

FIG. 64 is an enlarged view of detail B in FIG. 63, illustrating a distal portion of the vertebral anchor of FIG. 31.

FIG. 67 is another perspective view of the vertebral anchor of FIG. 61.

FIG. 68 is an end view of the vertebral anchor of FIG. 61.

FIG. 80 is a top perspective view of an alternative allograft spacer in accordance with some embodiments.

DETAILED DESCRIPTION OF THE ILLUSTRATED EMBODIMENTS

The present application is generally directed to orthopedic systems, and in particular, to systems including plates and spacers.

The present application discloses orthopedic plating systems that can be used in spinal surgeries, such as spinal fusions. The plating systems disclosed herein include a plate and a spacer that are independent from one another. In some cases, the plate and the spacer can be pre-attached to one another before positioning them in a desired location of the spine. In other cases, the spacer can first be inserted into a desired location of the spine, and then the plate can be inserted thereafter. Advantageously, the plating systems disclosed herein are of low-profile. For example, they can provide a very small, anterior footprint cervical plate solution for fusion procedures. One skilled in the art will appreciate that while the plating systems can be used with cervical procedures, the plating systems are not limited to such areas, and can be used with other regions of the spine.

FIGS. 1A-1D illustrate different views of a plating system comprising a low profile plate attached to a spacer according to some embodiments. The plating system 5 includes a spacer 10 attached to a low-profile plate 50. Advantageously, the plating system 5 can be inserted through an anterior approach into a spine, and can desirably provide a small anterior footprint.

Figure 1A:
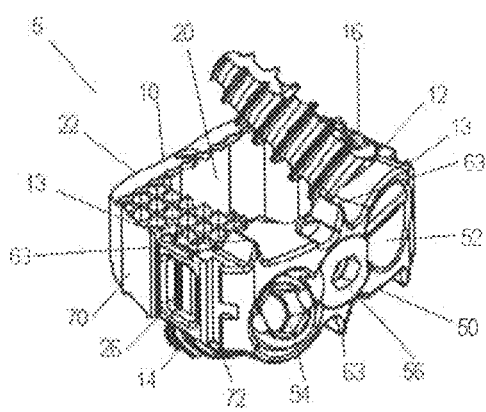
FIGS. 1A-1D illustrate different views of a low profile plate attached to a spacer according to some embodiments.

The spacer 10 is configured to have an upper surface 12, a lower surface 14, and a leading end 22. In some embodiments, the upper surface 12 and/or lower surface 14 includes texturing 16, such as teeth, ribs, ripples, etc. to assist in providing frictional contact with adjacent vertebral bodies. In some embodiments, the leading end 22 of the spacer 10 can be slightly tapered, as shown in FIG. 1A. With the taper, the leading end 22 can serve as a distraction surface that helps the spacer to be inserted into an intervertebral space.

Figure 1B:
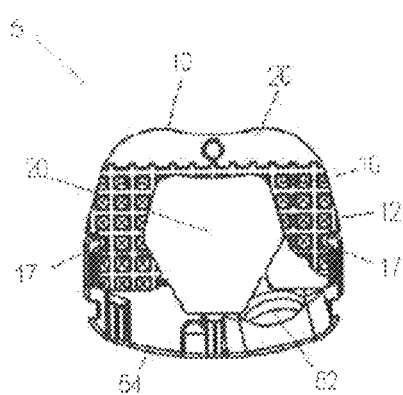

As shown in FIG. 1B, the leading end 22 can be concave, though in other embodiments, the leading end 22 can be straight or convex.

Figure 3A:
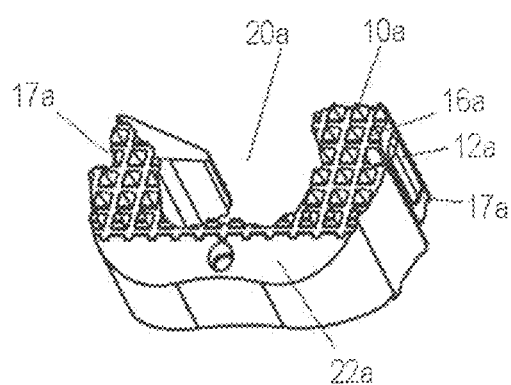
FIGS. 3A-3D illustrate different views of a PEEK spacer to be used with the low profile plate shown in FIGS. 2A-2D.
Figure 3B:
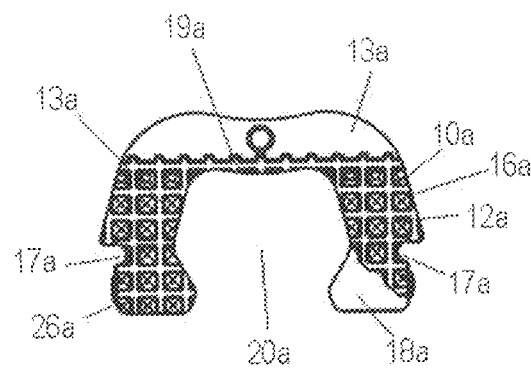

The spacer 10 can be substantially C-shaped (as shown in FIG. 3B), whereby it includes two side arms 13 that surround an inner opening 20. Adjacent the side arms 13 is a convex wall 19. In some embodiments, the convex wall 19 is substantially parallel to the concave surface of the leading end 22. The opening 20, which is configured to receive natural or synthetic graft material therein to assist in a fusion procedure, has an open side that is opposite convex wall 19, thereby giving the spacer 10 its C-shape.

The spacer 10 has a number of unique features that accommodate the attachment of a plate 50 thereto. Each of the side arms 13 of the spacer 10 includes a notch 17 (shown in FIG. 3B) for receiving a corresponding protrusion 71 of a lateral arm or extension 70 of the plate 50, thereby advantageously forming a first locking mechanism between the spacer 10 and the plate 50. In addition, in some embodiments, each of the side arms 13 of the spacer 10 can also include a hump region 26 (shown in FIG. 3B) that can extend in part into a window 72 of an attached plate 50 (shown in FIG. 2A), thereby advantageously providing a second locking mechanism between the spacer 10 and the plate 50. Advantageously, by providing secure first and second locking mechanisms between the spacer 10 and the plate 50, the plate and spacer will be kept securely together during any type of impaction of the plating system within the body. Furthermore, each of the side arms 13 of the spacer 10 can include a cut-away portion or chamfer 18, 19 (shown in FIG. 3C) to advantageously accommodate screws which pass through the plate. In embodiments that involve a pair of screws through the plate 50—one of which passes in an upward direction, and the other of which passes in a downward direction—one side arm 13 of the spacer 10 will include an upper chamfer 18 formed on an upper surface to accommodate the upwardly directed screw, while the second side arm 13 of the spacer will include a lower chamfer 19 formed on a lower surface to accommodate the downwardly directed screw.

Figure 4A:
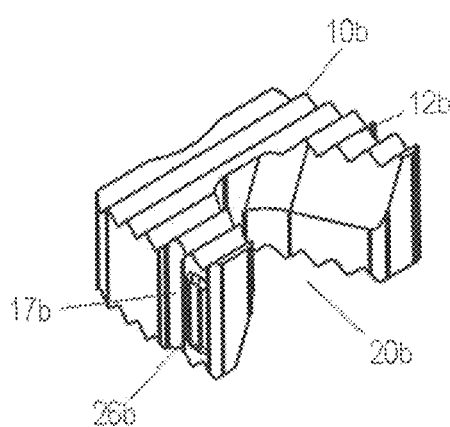
FIGS. 4A-4D illustrate different views of an allograft spacer to be used with the low profile plate shown in FIGS. 2A-2D.

The spacer 10 can be formed of any material. In some embodiments, the spacer 10 is formed of a polymer, such as PEEK, as shown in FIG. 3A. In some embodiments, the spacer 10 is formed of allograft bone, as shown in FIG. 4A. In some instances, to form an allograft implant, allograft bone may be cut or shaved from a desired bone member. The cut allograft bone will then be assembled together, using an adhesive or mechanical fastener (e.g., bone pins). Accordingly, in some embodiments, an allograft spacer 10 is formed of two, three, four or more layers that are assembled together, such as by one or more bone pins. One particular advantage of the invention is that the plate 50 can work with a variety of different spacers 10, as the plate 50 is independently removable from and attachable to the spacer 10. Regardless of whether a surgeon chooses to implant an allograft spacer or PEEK spacer 10 into an intervertebral space, the surgeon can simply attach the low-profile plate 50 to the spacer 10 following implantation into the intervertebral space.

The plate 50 is configured to have a plate body and a pair of lateral extensions 70 that extend from the plate body, each of which has a protrusion 71, for inserting into a corresponding notch 17 of the spacer 10. These lateral extensions 70 help form the first locking mechanism between the plate 50 and the spacer 10, as discussed above. In addition, the lateral extensions 70 of the plate 50 each include a window 72 (shown in FIG. 2A) for receiving a hump region 26 on the arms 13 of the spacer 10, thereby helping to form the second locking mechanism between the plate 50 and the spacer 10, as discussed above.

In addition to attaching to the spacer 10, the plate 50 is also configured to attach into one or more vertebral bodies via one or more bone screws. As shown in FIG. 1A, the plate 50 includes a first screw hole 52 and a second screw hole 54 for receiving bone screws therein. In some embodiments, screw hole 52 is angled upwardly such that an inserted bone screw passes upward into an upper vertebral body, while screw hole 54 is angled downwardly such that an inserted bone screw passes downward into a lower vertebral body. While the illustrated embodiment illustrates a pair of screw holes for receiving a pair of bone screws, it is possible to have one, three, four, five or more screw holes for receiving a different number of bone screws.

Figure 1C:
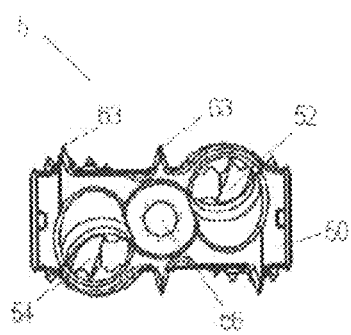
Figure 1D:
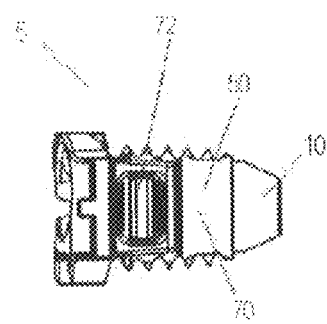

Over time, it is possible for bone screws to back-out. The plate 50 thus has a blocking or set screw 56 (shown in FIG. 1C) that assists in preventing back-out of inserted bone screws. As shown in FIG. 1C, the set screw 56 can be in an initial position that allows first and second bone screws to pass through holes 52, 54. Once the bone screws have been inserted through the holes 52, 54, the set screw 56 can be rotated (e.g., 90 degrees), to thereby block the bone screws and prevent back out of the bone screws. In some embodiments, the set screw 56 abuts a side of the head of the bone screws to prevent back-out of the bone screws, while in other embodiments, the set screw 56 rests over a top of the head of the bone screws to prevent back-out of the bone screws. In some embodiments, the set screw 56 comes pre-fixed with the plate 50. As shown in FIG. 1C, a single set screw 56 can be used to conveniently block a pair of bone screws. In other embodiments, each bone screw can be assigned its own set screw, which can operate independently of one another, to prevent back-out of the bone screw.

The plate 50 can also include one or more knife-like edges 63 that provide additional torsional stabilization when the plate 50 rests against a bone member. As shown in FIG. 1C, the knife-like edges 63 can be formed on both the upper and lower surfaces of the plate 50 body. While the illustrated embodiment shows a pair of knife-like edges 63 on an upper surface of the plate body and a pair of knife-like edges 63 on a lower surface of the plate body, one skilled in the art will appreciate that a different number of knife-like edges 63 can be provided.

FIGS. 2A-2D illustrate different views of the low profile plate shown in FIGS. 1A-1D. From these views, one can see the pair of lateral extensions 70 that extend from the body of the plate 50. At the distal end of each of the lateral extensions 70 is an inwardly-facing protrusion 71 that is configured to fit into a corresponding notch in the spacer 10. In addition, from these views, one can see the windows 72 that are formed in each of the lateral extensions 70. The windows 72 advantageously receive hump regions 26 of the spacer to provide a locking mechanism, and also help to improve desirable radiolucency. Advantageously, the windows 72 can have rounded edges to accommodate the spacer 10 therein. While the illustrated windows 72 are shown as rectangular with rounded edges, in other embodiments, the windows 72 can have a different shape, such as circular or oval. In some embodiments, the plate 50 is assembled axially to the spacer 10.

Figure 2A:
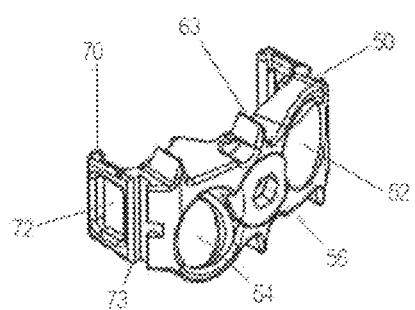
FIGS. 2A-2D illustrate different views of the low profile plate shown in FIGS. 1A-1D.
Figure 2B:
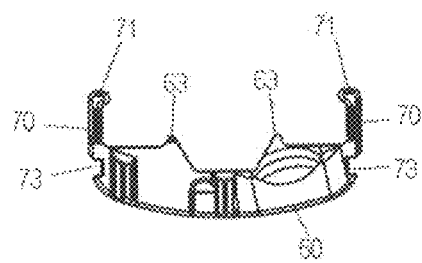
Figure 2C:
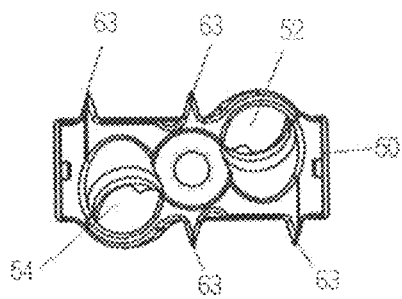
Figure 2D:
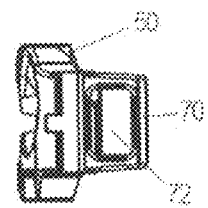
Figure 3C:
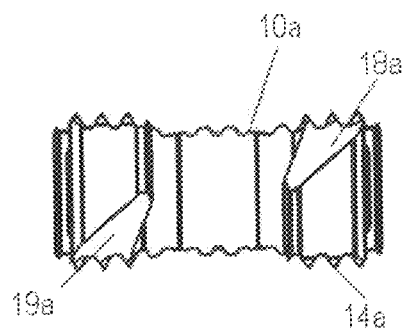
Figure 3D:
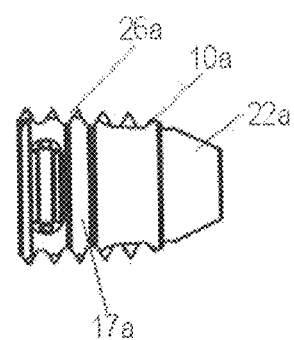

In some embodiments, the low profile plate 50 can also include indented gripping sections 73 (shown in FIGS. 2A and 2B). These indented gripping sections 73 advantageously provide a gripping surface for an insertion instrument, thereby facilitating easy delivery of the plate to a spacer body during surgery.

FIGS. 3A-3D illustrate different views of a PEEK spacer to be used with the low profile plate shown in FIGS. 2A-2D. From these views, one can see how the spacer 10a includes an upper surface 12a and a lower surface 14a with texturing 16a; a generally C-shaped body including a pair of arms 13a each having a notch 17a formed therein and an upper chamfer 18a or lower chamfer 19a; and a tapered leading edge 22a. In addition, one skilled in the art can appreciate the substantially symmetric shape of the inner opening 20a, which serves as a graft hole for receiving graft material therein.

Figure 4B:
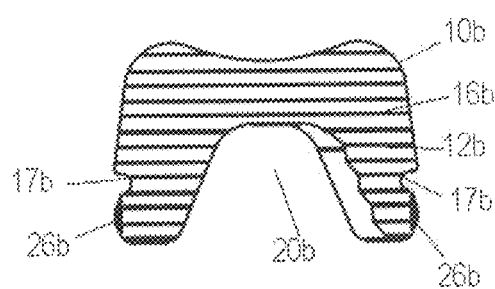
Figure 4C:
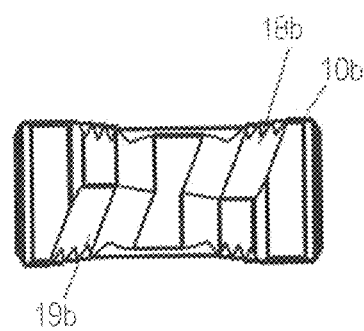
Figure 4D:
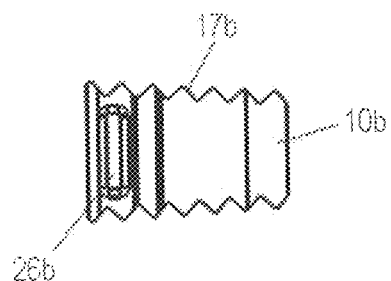

FIGS. 4A-4D illustrate different views of an allograft spacer to be used with the lower profile plate shown in FIGS. 2A-2D. While the allograft spacer 10b shares similar features to the PEEK spacer 10a shown in previous figures, such as the notches 17b, hump surfaces 26b, and chamfers 18b,19b, the allograft spacer 10b need not be the same. For example, the shape of the graft opening 20b can be more of an arch, as shown in FIG. 4B.

FIGS. 5A-5D illustrate different views of a second alternative embodiment of a low profile plate attached to a spacer according to some embodiments. Rather than having a plate 50 with lateral extensions 70 that extend around the outer surface of a spacer 10, the present embodiment of the plating system 105 includes a plate 150 with an enclosed posterior extension 155 that fits within the body of the spacer 110. The enclosed posterior extension 155 includes extending surfaces 166, 167 that are fitted into corresponding inlets 121, 123 formed in the body of the spacer 110, thereby forming a first locking mechanism between the plate 150 and the spacer 110. In addition, the enclosed posterior extension 155 of the plate 50 includes one or more deformable locking tabs 160 (shown in FIG. 6B) that securely lock into tab holes 181a in the spacer body 110, thereby forming a second locking mechanism between the plate 150 and the spacer 110. While in some embodiments, the plate 150 can be attached to the spacer 110 after inserting the spacer 110 into a desired location in the body, in other embodiments, the plate 150 can be pre-assembled with the spacer 110 prior to inserting the plating system 105 into the desired location.

Figure 7A:
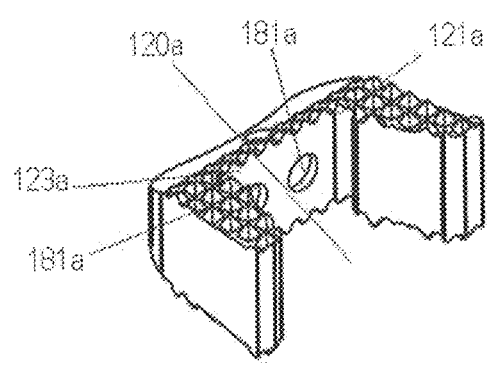
FIGS. 7A-7D illustrate different views of a PEEK spacer to be used with the low profile plate in FIGS. 6A-6D.

Like the spacer 10 in FIG. 1A, the spacer 110 is configured to have an upper surface 112, a lower surface 114, and a leading end 122. In some embodiments, the upper surface 112 and/or lower surface 114 includes texturing 116, such as teeth, ribs, ripples, etc. to assist in providing frictional contact with adjacent vertebral bodies. In some embodiments, the leading end 122 of the spacer 110 can be slightly tapered, as shown in FIG. 7D. With the taper, the leading end 122 can serve as a distraction surface that helps the spacer 110 to be inserted into an intervertebral space. As shown in FIG. 1B, the leading end 122 can be concave, though in other embodiments, the leading end 122 can be straight or convex.

Figure 7B:
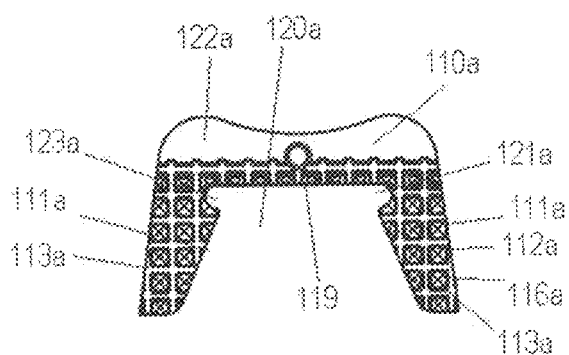
Figure 7C:
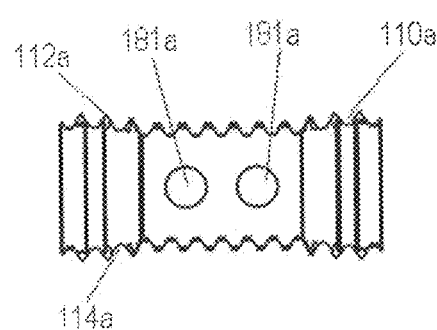
Figure 7D:
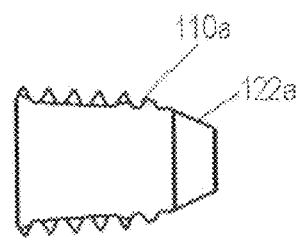

The spacer 110 can be substantially C-shaped (as shown in FIG. 7B), whereby it includes two side arms 113 that surround an inner opening 120. Adjacent the side arms 113 is a straight wall 119 that forms the border of the graft opening 120. The straight wall 119 can include one or more tab holes 181 (shown in FIG. 7A) for receiving deformable tab locks 160 therein. The graft opening 20, which is configured to receive natural or synthetic graft material therein to assist in a fusion procedure, has an open side that is opposite the straight wall 119, thereby giving the spacer 110 its C-shape.

In some embodiments, the graft opening 120 (shown in FIG. 7B) has a different shape from the opening 20 of the spacer 10 of the prior embodiment, as the graft opening 120 is configured to not only receive graft material, but also the enclosed posterior extension 155 of the plate 150. For example, the graft opening 120 includes two inlets—a first inlet 121 formed at the junction between the first arm 113 and wall 119 and a second inlet 123 formed at the junction between the second arm 113 and wall 119 (shown in FIG. 7B)—for receiving outwardly extending surfaces 166, 167 of the plate 150 (shown in FIG. 6B). In addition, the graft opening 120 includes two outwardly tapering walls 111 that provide enough space to accommodate any bone screws inserted in the plate 150. As such, additional chamfers 18, 19 (as shown in FIG. 3B) are optional.

Figure 8A:
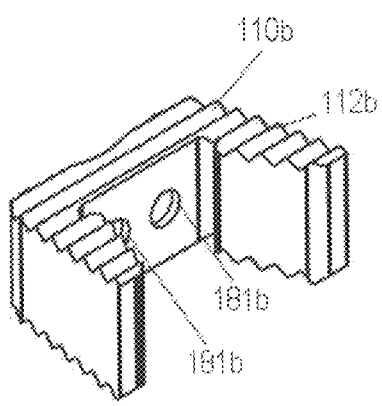
FIGS. 8A-8D illustrate different views of an allograft spacer to be used with the low profile plate in FIGS. 6A-6D.
Figure 8B:
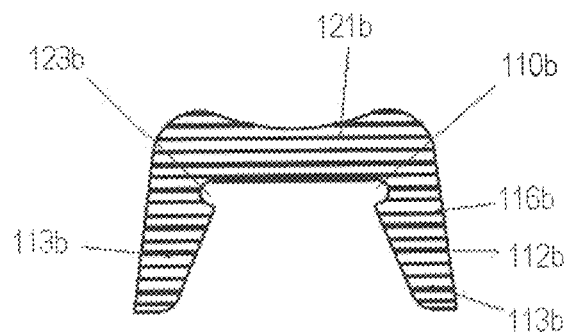
Figure 8C:
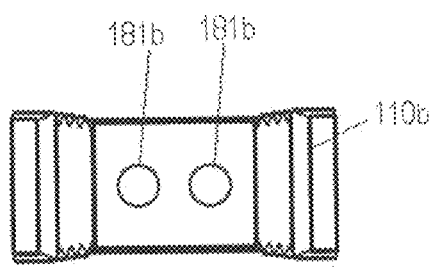
Figure 8D:
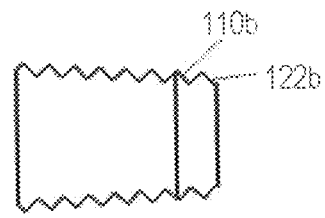

Like spacer 10, the spacer 110 can be formed of a variety of materials. In some embodiments, the spacer 110 comprises PEEK, as shown in FIG. 7A, while in other embodiments, the spacer 110 comprises allograft bone, as shown in FIG. 8A.

The plate 150 is configured to have a plate body, and an enclosed posterior extension 155 that extends from the plate body, which is received within and retains the spacer 110. The enclosed posterior extension 155 includes first and second outwardly extending surfaces 166, 167 that fit into inlets 121, 123 formed within the spacer 110 body to form a first locking mechanism. In addition, one or more deformable tab locks 160 extend from an exterior surface of the enclosed posterior extension 155 and are received in corresponding tab holes 181 in the spacer 110 to form a second locking mechanism. In some embodiments, the side walls of the enclosed posterior extension 155 can include one or more windows 172 (shown in FIG. 6A) for improving radiolucency of the plating system. In some embodiments, the plate 150 is assembled axially to the spacer 110.

Figure 5A:
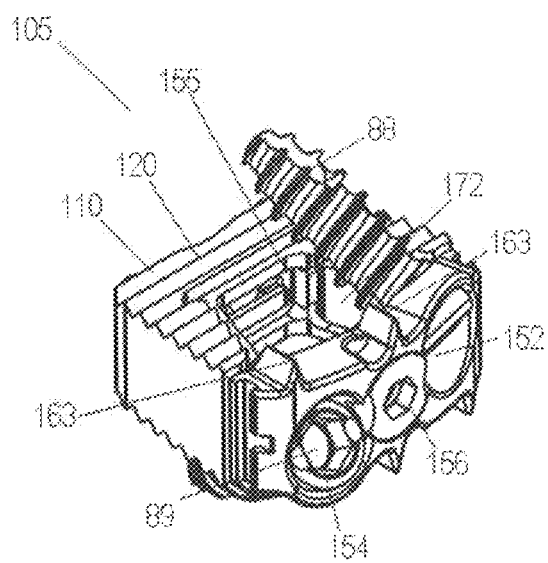
FIGS. 5A-5D illustrate different views of a second alternative embodiment of a low profile plate attached to a spacer according to some embodiments.
Figure 5B:
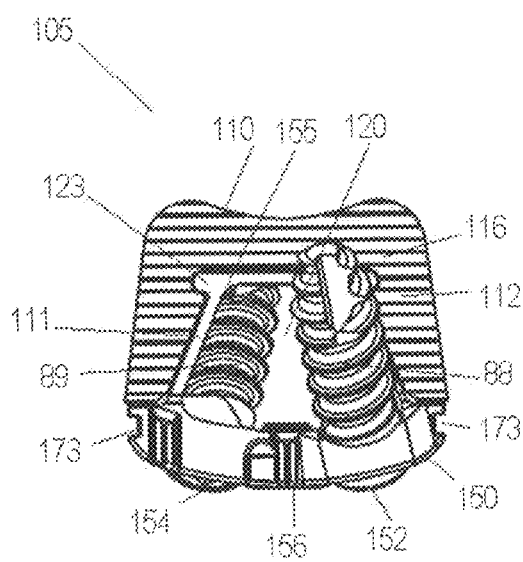

In addition to attaching to the spacer 110, the plate 150 is also configured to attach into one or more vertebral bodies via one or more bone screws 88, 89. As shown in FIG. 5A, the plate 150 includes a first screw hole 152 and a second screw hole 154 for receiving bone screws 88, 89 therein. In some embodiments, screw hole 152 is angled upwardly such that an inserted bone screw 88 passes upward into an upper vertebral body, while screw hole 154 is angled downwardly such that an inserted bone screw 89 passes downward into a lower vertebral body. While the illustrated embodiment illustrates a pair of screw holes for receiving a pair of bone screws, it is possible to have one, three, four, five or more screw holes for receiving a different number of bone screws.

Figure 5C:
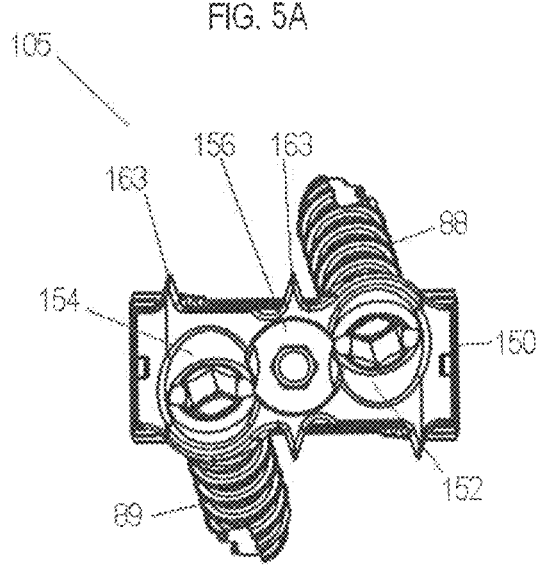
Figure 5D:
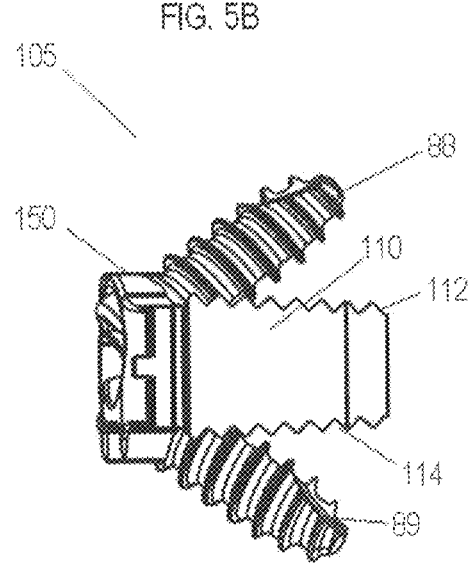

Over time, it is possible for bone screws to back-out. The plate 150 thus has a blocking or set screw 156 (shown in FIG. 5C) that assists in preventing back-out of inserted bone screws. As shown in FIG. 5C, the set screw 156 can be in an initial position that allows first and second bone screws to pass through holes 152, 154. Once the bone screws have been inserted through the holes 152, 154, the set screw 156 can be rotated (e.g., 90 degrees), to thereby block the bone screws and prevent back out of the bone screws. In some embodiments, the set screw 156 abuts a side of the head of the bone screws to prevent back-out of the bone screws, while in other embodiments, the set screw 156 rests over a top of the head of the bone screws to prevent back-out of the bone screws. In some embodiments, the set screw 156 comes pre-fixed with the plate 150. As shown in FIG. 5C, a single set screw 156 can be used to conveniently block a pair of bone screws. In other embodiments, each bone screw can be assigned its own set screw, which can operate independently of one another, to prevent back-out of the bone screw.

The plate 150 can also include one or more torsional stabilizers 163. In some embodiments, the torsional stabilizers 163 can comprise knife-like edges 163 that provide additional torsional stabilization when the plate 150 rests against a bone member. As shown in FIG. 5C, the knife-like edges 163 can be formed on both the upper and lower surfaces of the plate 150 body. While the illustrated embodiment shows a pair of knife-like edges 163 on an upper surface of the plate body and a pair of knife-like edges 163 on a lower surface of the plate body, one skilled in the art will appreciate that a different number of knife-like edges 163 can be provided. In some embodiments, the torsional stabilizers 163 are flush with the body of the plate 150.

FIGS. 6A-6D illustrate different views of the low profile plate shown in FIGS. 5A-5D. From these views, one can see the enclosed posterior extension 155 that extends from the body of the plate 150. At the distal end of the enclosed posterior extension 155 are a pair of outwardly extending surfaces 166, 167 that are configured to fit within inlets 121, 123 formed in the spacer. From these views, one can also see the deformable tab lock 160 (FIG. 6B) that can help secure the plate 150 to the spacer 110. In addition, from these views, one can see the windows 172 that are formed in each of the arms of the enclosed posterior extension 155. The windows 172 advantageously help to improve desirable radiolucency, and are of large size to provide a large viewing surface area. While the illustrated windows 172 are shown as triangular with rounded edges, in other embodiments, the windows 172 can have a different shape, such as circular or oval. In some embodiments, the plate 150 is assembled axially to the spacer 110.

Figure 6A:
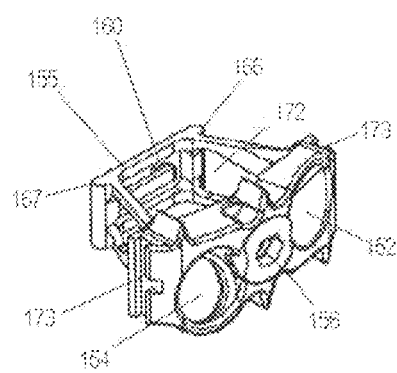
FIGS. 6A-6D illustrate different views of the low profile plate shown in FIGS. 5A-5D.
Figure 6B:
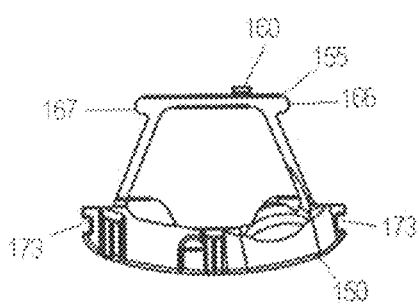
Figure 6C:
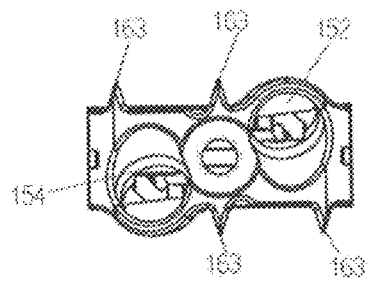
Figure 6D:
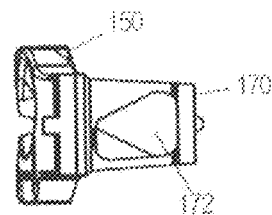

In some embodiments, the low profile plate 150 can also include indented gripping sections 173 (shown in FIGS. 6A and 6B). These indented gripping sections 173 advantageously provide a gripping surface for an insertion instrument, thereby facilitating easy delivery of the plate to a spacer body during surgery.

FIGS. 7A-7D illustrate different views of a PEEK spacer to be used with the low profile plate shown in FIGS. 5A-5D. From these views, one can see how the spacer 110a includes an upper surface 112a and a lower surface 114a with texturing 116a; a generally C-shaped body including a pair of arms 113a each having an inner inlet 121, 123a formed therein; and a tapered leading edge 122a. In addition, one skilled in the art can appreciate the substantially symmetric shape of the inner opening 120a, which serves as a graft hole for receiving graft material therein.

FIGS. 8A-8D illustrate different views of an allograft spacer to be used with the lower profile plate shown in FIGS. 5A-5D. While the allograft spacer 110b shares similar features to the PEEK spacer 110a shown in previous figures, such as the C-shaped body including a pair of arms 113b each having an inlet 121b, 123b formed therein, the allograft spacer 110b need not be the same.

FIGS. 9A-9D illustrate different views of a third alternative embodiment of a low profile plate attached to a spacer according to some embodiments. In the present embodiment, the plating system 205 includes a plate 250 having lateral arms or extensions 270 that extend around an exterior surface of a spacer 210. The lateral extensions 270 extend wider than the lateral extensions 70 in the first embodiment, and do not necessarily have to interlock with the spacer 210. While in some embodiments, the plate 250 can be attached to the spacer 210 after inserting the spacer 210 into a desired location in the body, in other embodiments, the plate 250 can be pre-assembled with the spacer 210 prior to inserting the plating system 205 into the desired location.

Figure 9A:
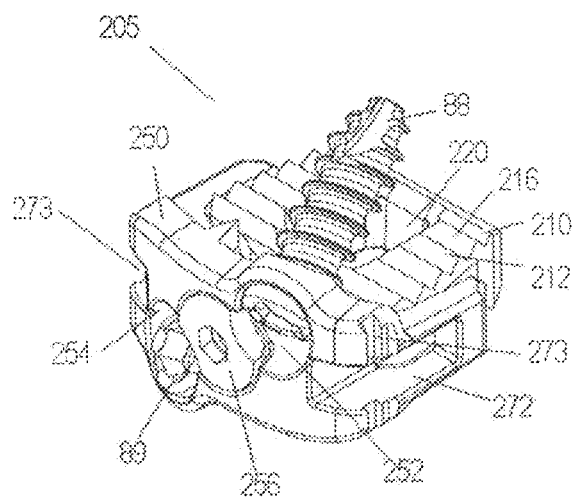
FIGS. 9A-9D illustrate different views of a third alternative embodiment of a low profile plate attached to a spacer according to some embodiments.
Figure 9B:
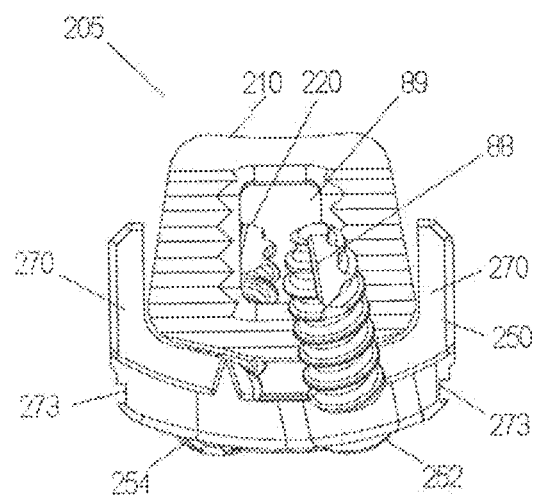
Figure 9C:
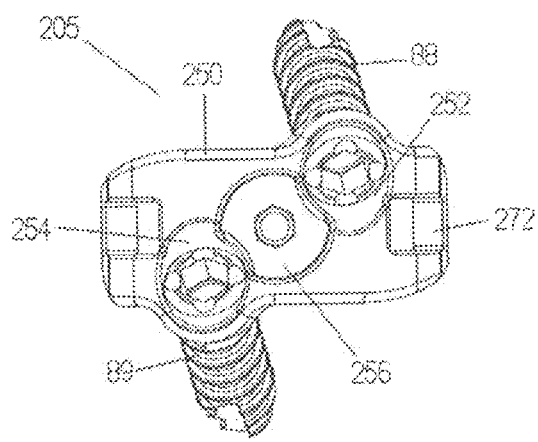
Figure 9D:
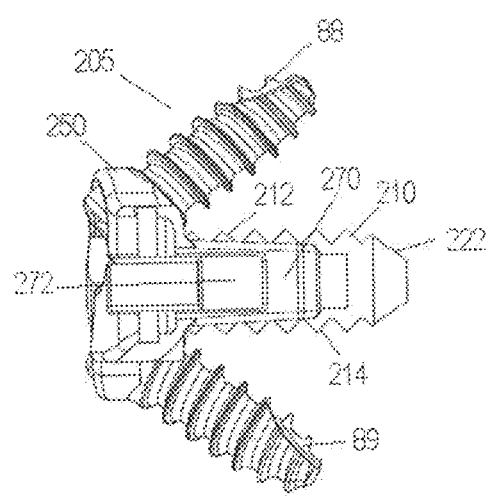

Like the spacer 10 in FIG. 1A, the spacer 210 is configured to have an upper surface 212, a lower surface 214, and a leading end 222. In some embodiments, the upper surface 212 and/or lower surface 214 includes texturing 216, such as teeth, ribs, ripples, etc. to assist in providing frictional contact with adjacent vertebral bodies. In some embodiments, the leading end 222 of the spacer 210 can be slightly tapered, as shown in FIG. 9D. With the taper, the leading end 222 can serve as a distraction surface that helps the spacer 210 to be inserted into an intervertebral space. As shown in FIG. 9B, the leading end 222 can be slightly concave, though in other embodiments, the leading end 122 can be straight or convex. Unlike previously illustrated spacers, the spacer 210 can have a graft hole 220 that is completely enclosed. As shown in FIG. 9B, the graft hole 220 can surrounded by four walls. In addition, the spacer 210 can include four outer walls: two straight walls, a convex wall and a concave wall.

In some embodiments, the graft opening 220 (shown in FIG. 9B) has a different shape from the openings of prior embodiments, as the graft opening 220 is enclosed. While the graft opening 220 is rectangular with rounded edges, in other embodiments, the graft opening 220 can have a different shape. For example, in some embodiments, the graft opening 220 can have curved walls, instead of straight walls, or can have tapered walls, instead of straight walls.

Like spacer 10, the spacer 210 can be formed of a variety of materials. In some embodiments, the spacer 210 comprises allograft bone, while in other embodiments, the spacer 210 comprises PEEK.

The plate 250 is configured to have a pair of lateral extensions 270 that receive the spacer 210. As shown in FIG. 9A, in some embodiments, the lateral extensions 270 include one or more windows 272 for improving radiolucency of the plating system. In some embodiments, the plate 250 is assembled axially to the spacer 210.

In addition to capturing the spacer 210, the plate 250 is also configured to attach into one or more vertebral bodies via one or more bone screws 88, 89. As shown in FIG. 9A, the plate 250 includes a first screw hole 252 and a second screw hole 254 for receiving bone screws 88, 89 therein. In some embodiments, screw hole 252 is angled upwardly such that an inserted bone screw 88 passes upward into an upper vertebral body, while screw hole 254 is angled downwardly such that an inserted bone screw 89 passes downward into a lower vertebral body. While the illustrated embodiment illustrates a pair of screw holes for receiving a pair of bone screws, it is possible to have one, three, four, five or more screw holes for receiving a different number of bone screws.

Over time, it is possible for bone screws to back-out. The plate 250 thus has a blocking or set screw 256 (shown in FIG. 9C) that assists in preventing back-out of inserted bone screws. As shown in FIG. 9C, the set screw 256 can be in an initial position that allows first and second bone screws to pass through holes 252, 254. Once the bone screws have been inserted through the holes 252, 254, the set screw 256 can be rotated (e.g., 90 degrees), to thereby block the bone screws and prevent back out of the bone screws. In some embodiments, the set screw 256 abuts a side of the head of the bone screws to prevent back-out of the bone screws, while in other embodiments, the set screw 256 rests over a top of the head of the bone screws to prevent back-out of the bone screws. In some embodiments, the set screw 256 comes pre-fixed with the plate 250. As shown in FIG. 9C, a single set screw 256 can be used to conveniently block a pair of bone screws. In other embodiments, each bone screw can be assigned its own set screw, which can operate independently of one another, to prevent back-out of the bone screw.

FIGS. 10A-10D illustrate different views of the low profile plate shown in FIGS. 9A-9D. From these views, one can see the lateral extensions 270 that extend from the body of the plate 250. From these views, one can also see the windows 272 (FIG. 10A) that extend along a substantial length of the lateral extensions 270. In some embodiments, each window 272 has a length greater than half the length of each lateral extension 270, thereby advantageously increasing the radiolucency of the plating system. In some embodiments, the plate 250 is assembled axially to the spacer 210.

Figure 10A:
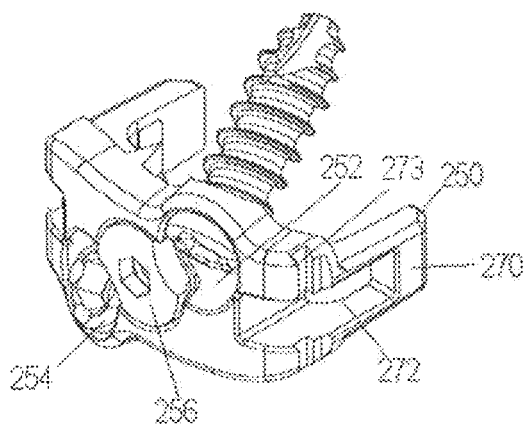
FIGS. 10A-10D illustrate different views of the low profile plate shown in FIGS. 9A-9D.
Figure 10B:
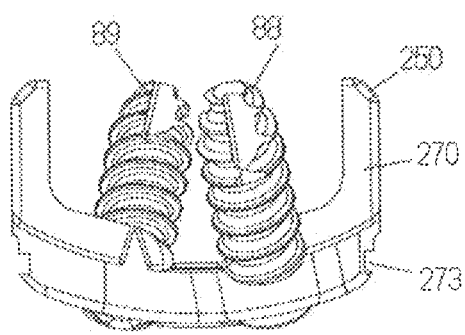
Figure 10C:
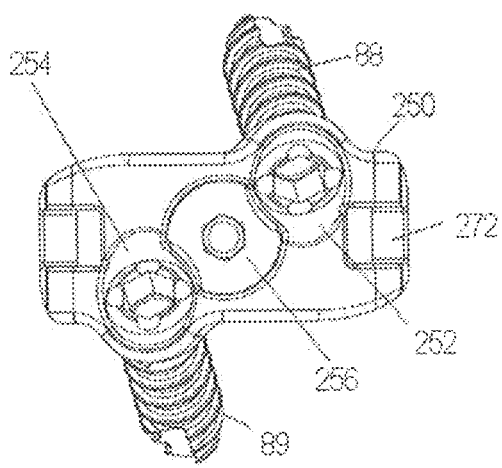
Figure 10D:
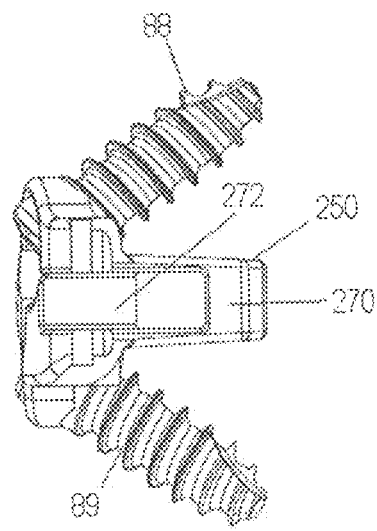

In some embodiments, the low profile plate 250 can also include indented gripping sections 273 (shown in FIGS. 10A and 10B). These indented gripping sections 273 advantageously provide a gripping surface for an insertion instrument, thereby facilitating easy delivery of the plate to a spacer body during surgery.

FIGS. 11A-11D illustrate different views of a fourth alternative embodiment of a low profile plate attached to a spacer according to some embodiments. Like the previous embodiment, the plating system 305 includes a plate 350 having lateral arms or extensions 370 that extend around an exterior surface of a spacer 310. The lateral extensions 370 extend wider than the lateral extensions 70 in the first embodiment, and do not necessarily have to interlock with the spacer 310. While in some embodiments, the plate 350 can be attached to the spacer 310 after inserting the spacer 310 into a desired location in the body, in other embodiments, the plate 350 can be pre-assembled with the spacer 310 prior to inserting the plating system 305 into the desired location.

Figure 11A:
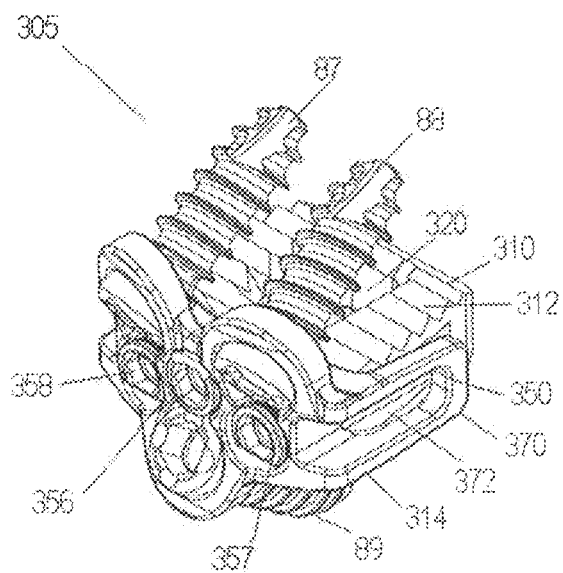
FIGS. 11A-11D illustrate different views of a fourth alternative embodiment of a low profile plate attached to a spacer according to some embodiments.
Figure 11B:
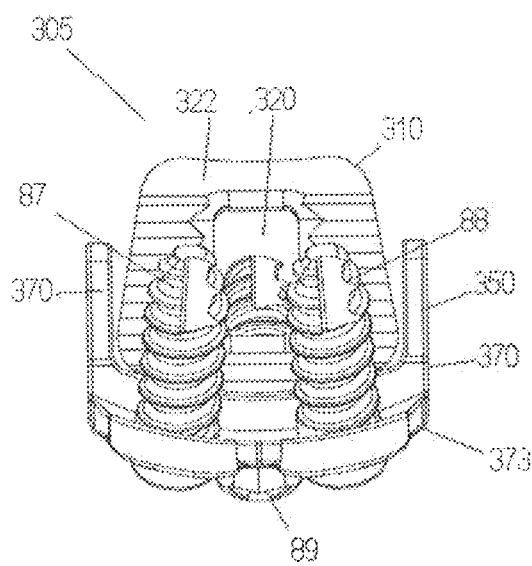
Figure 11C:
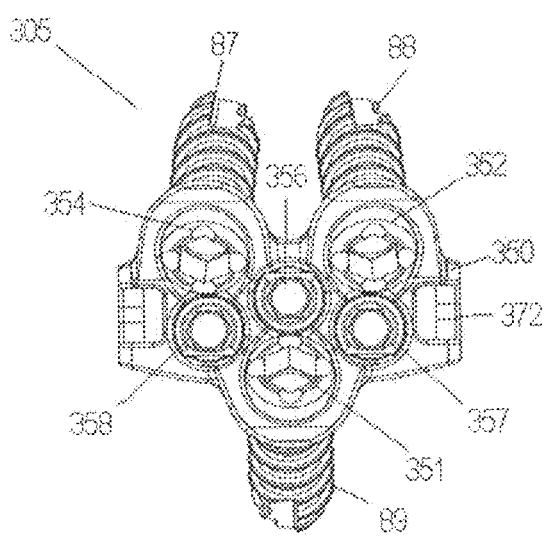
Figure 11D:
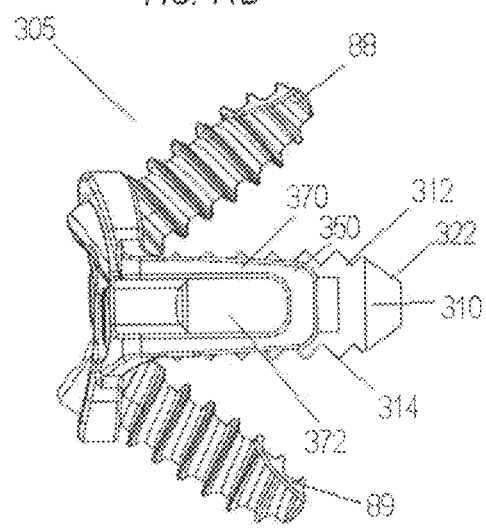

Like the spacer 10 in FIG. 1A, the spacer 310 is configured to have an upper surface 312, a lower surface 314, and a leading end 322. In some embodiments, the upper surface 312 and/or lower surface 314 includes texturing 316, such as teeth, ribs, ripples, etc. to assist in providing frictional contact with adjacent vertebral bodies. In some embodiments, the leading end 322 of the spacer 310 can be slightly tapered, as shown in FIG. 11D. With the taper, the leading end 322 can serve as a distraction surface that helps the spacer 310 to be inserted into an intervertebral space. As shown in FIG. 11B, the leading end 322 can be slightly concave, though in other embodiments, the leading end 322 can be straight or convex. In some embodiments, the spacer 310 can have a graft hole 320 that is completely enclosed. As shown in FIG. 11B, the graft hole 320 can surrounded by four walls. In addition, the spacer 310 can be comprised of four outer walls: two straight, one concave and one convex.

In some embodiments, the graft opening 320 (shown in FIG. 11B) of the spacer 310 is enclosed. While the graft opening 320 is rectangular with rounded edges, in other embodiments, the graft opening 320 can have a different shape. For example, in some embodiments, the graft opening 320 can have curved walls, instead of straight walls, or can have tapered walls, instead of straight walls.

Like spacer 10, the spacer 310 can be formed of a variety of materials. In some embodiments, the spacer 210 comprises allograft bone, while in other embodiments, the spacer 310 comprises PEEK.

The plate 350 is configured to have a pair of lateral extensions 370 that receive the spacer 310. As shown in FIG. 11A, in some embodiments, the lateral extensions 370 include one or more windows 372 for improving radiolucency of the plating system. In some embodiments, the plate 350 is assembled axially to the spacer 310.

In addition to capturing the spacer 310, the plate 350 is also configured to attach into one or more vertebral bodies via one or more bone screws 88, 89. As shown in FIG. 9A, the plate 350 includes a first screw hole 351, a second screw hole 352 and a third screw hole 354 for receiving bone screws 87, 88, 89 therein. In some embodiments, screw holes 352 and 354 are angled upwardly such that inserted bone screws 87, 88 pass upward into an upper vertebral body, while screw hole 351 is angled downwardly such that inserted bone screw 89 passes downward into a lower vertebral body. While the illustrated embodiment illustrates three screw holes for receiving three bone screws, it is possible to have one, two, four, five or more screw holes for receiving a different number of bone screws.

Figure 12A:
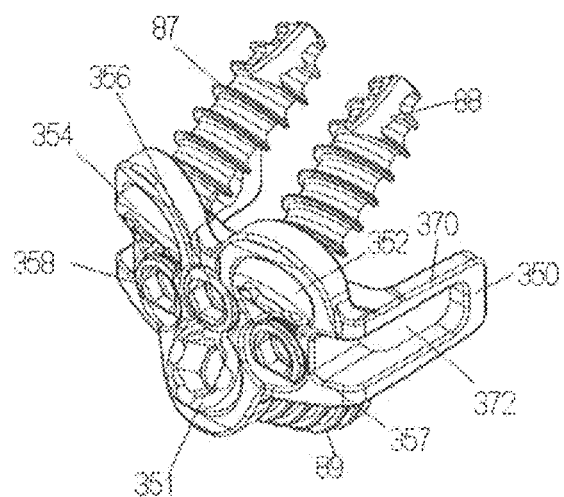
FIGS. 12A-12D illustrate different views of the low profile plate shown in FIGS. 11A-11D.
Figure 12B:
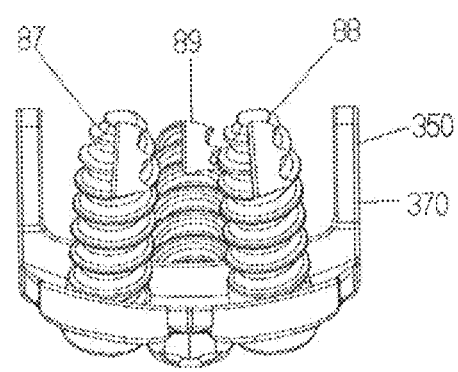
Figure 12C:
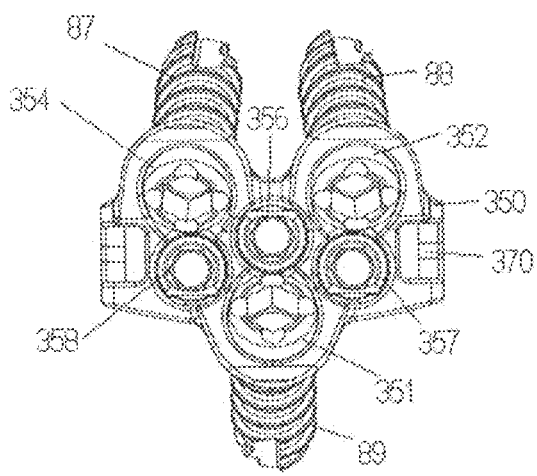
Figure 12D:
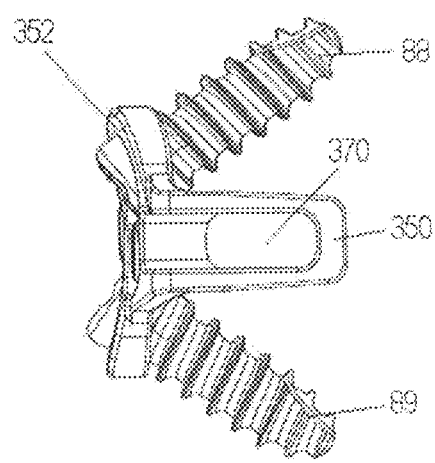

Over time, it is possible for bone screws to back-out. The plate 350 thus has blocking or set screws 356, 357, 358 (shown in FIG. 12C), each of which corresponds to one of screw holes 351, 352, 354. As shown in FIG. 12C, the set screws 356, 357, 358 can be in an initial position that allows first, second and third bone screws to pass through holes 351, 352, 354. Once the bone screws have been inserted through the holes 351, 352, 354, the set screws 356, 357, 358 can be rotated (e.g., 90 degrees), to thereby block the bone screws and prevent back out of the bone screws. In some embodiments, the set screws 356, 357, 358 abut a side of the head of the bone screws to prevent back-out of the bone screws, while in other embodiments, the set screws 356, 357, 358 rest over a top of the head of the bone screws to prevent back-out of the bone screws. In some embodiments, the set screws 356, 357, 358 come pre-fixed with the plate 350. As shown in FIG. 12C, a single set screw 356, 357, 358 can be used to conveniently block a single bone screws. In other embodiments, each set screw can be designed to block more than one set screw to prevent back-out of the bone screw.

FIGS. 12A-12D illustrate different views of the low profile plate shown in FIGS. 11A-11D. From these views, one can see the lateral extensions 370 that extend from the body of the plate 350. From these views, one can also see the windows 372 (FIG. 12A) that extend along a substantial length of the lateral extensions 370. In some embodiments, each window 372 has a length greater than half the length of each lateral extension 370, thereby advantageously increasing the radiolucency of the plating system. In some embodiments, the plate 350 is assembled axially to the spacer 310.

The plating systems describe include a plate that is independent from a spacer. The plate is low-profile and can be used with any type of spacer, such as allograft or PEEK.

FIGS. 13A-13D illustrate different views of a multi-piece allograft spacer to be used with the low profile plates discussed above according to some embodiments. The multi-piece allograft spacer 410 can be formed of an upper member 436 and a lower member 438 that are connected together via one or more pins 475. The upper member 436 and the lower member 438 each include cut-out portions that help form a graft opening 420 in the spacer 410.

The upper member 436 can include an upper surface having bone engagement surfaces (e.g., ridges, teeth, ribs) and a lower interfacing surface 446. The lower member 438 can include a lower surface having bone engagement surfaces (e.g., ridges, teeth, ribs) and an upper interfacing surface 448. In some embodiments, the upper member 436 can include one or more holes 462, while the lower member 438 can include one or more holes 464 which align with the one or more holes 462 of the upper member. The aligned holes are configured to receive one or more pins 475 to keep the upper and lower members of the allograft spacer together. In some embodiments, the pins 475 are also formed of bone material, such as allograft.

Figure 13A:
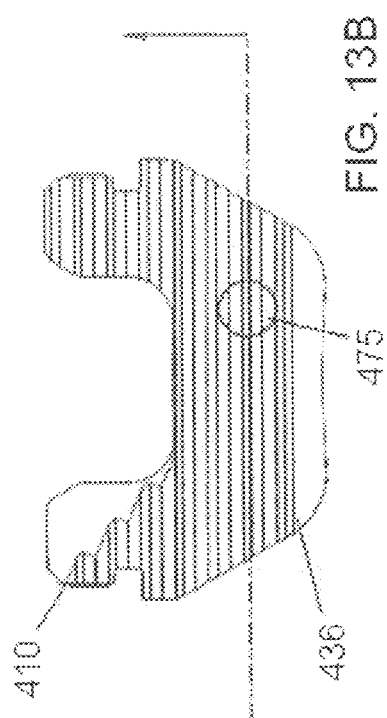
FIGS. 13A-13D illustrate different views of a multi-piece allograft spacer to be used with the low profile plates discussed above according to some embodiments.
Figure 13B:
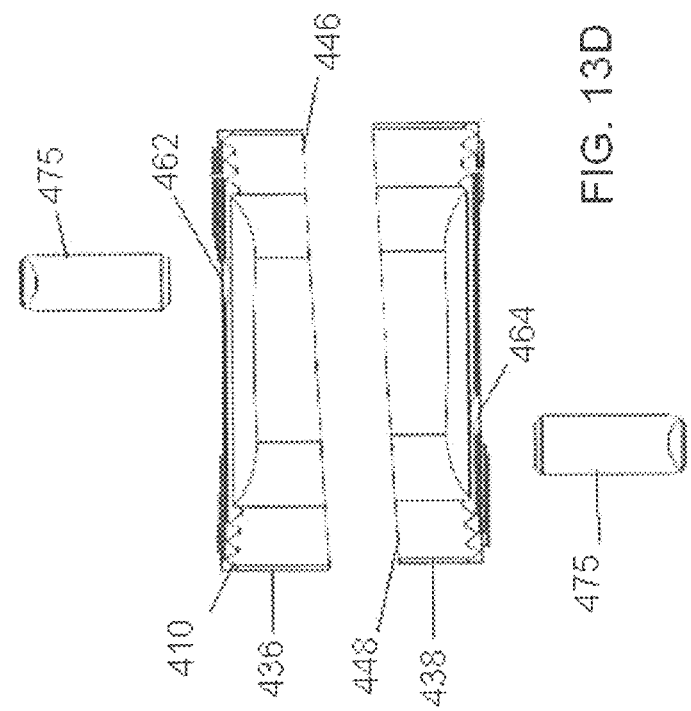
Figure 13C:
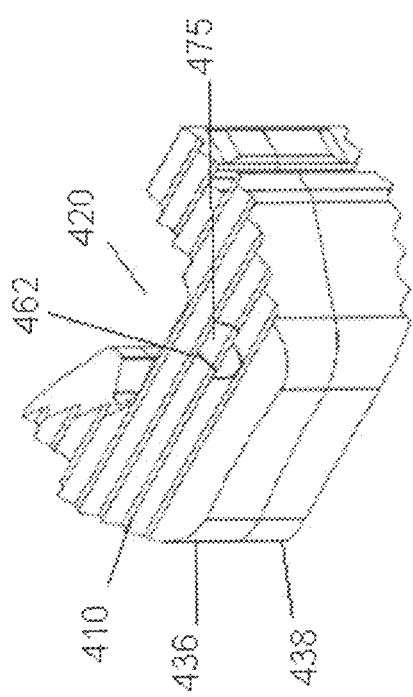
Figure 13D:
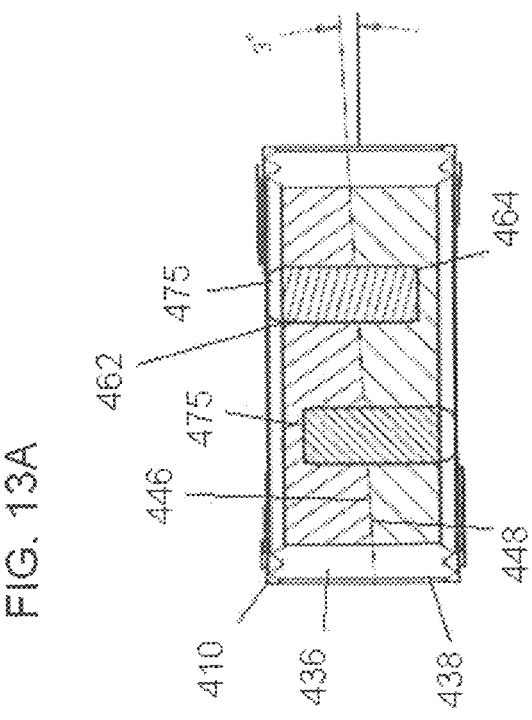

As shown best in FIG. 13C, the lower interfacing surface 446 of the upper member 436 is directly engaged with the upper interfacing surface 448 of the lower member 438. While the lower interfacing surface 446 and the upper interfacing surface 448 can be flat-on-flat, as both surfaces are planar, in some embodiments (as shown in FIG. 13C), the interface between the two surfaces is at an angle relative to the holes for receiving the pins 475. In other words, the pins 475 are received at an angle to the interface between the upper member 436 and the lower member 438. In addition, as shown in FIG. 13C, holes 462 and 464 need not go through the entirety of their respective members. For example, as shown in FIG. 13C, while hole 462 goes entirely through the upper and lower surface of the upper member 436, hole 464 goes only through the upper surface of the lower member 438, and does not go through to the lower surface. Accordingly, in some embodiments, aligned holes 462 and 464 create a "blind" pin-hole, whereby the hole does not go through the uppermost and lowermost surfaces of the spacer 410. Advantageously, in some embodiments, the use of such blind holes for receiving pins helps to maintain the pins within the spacer body.

FIGS. 14A-14D illustrate different views of an alternative multi-piece allograft spacer to be used with the lower profile plates discussed above according to some embodiments. The multi-piece allograft spacer 510 can be formed of a left member 536 and a right member 538 that are connected together in series or side-by-side (e.g., laterally) via one or more pins 575. The left member 536 and the right member 538 each include cut-out portions that help form a graft opening 520 in the spacer 510.

The left member 536 can include upper and lower surfaces having bone engagement surfaces (e.g., ridges, teeth, ribs). In addition, the left member 536 further includes a right interfacing surface 546. The right member 538 can also include upper and lower surfaces having bone engagement surfaces (e.g., ridges, teeth, ribs). In addition, the right member 538 further includes a left interfacing surface 548. In some embodiments, the left member 536 can include one or more holes 562, while the right member 538 can include one or more holes 564 which align with the one or more holes 562 of the left member. The aligned holes are configured to receive one or more pins 575 to keep the left and right members of the allograft spacer together.

Figure 14A:
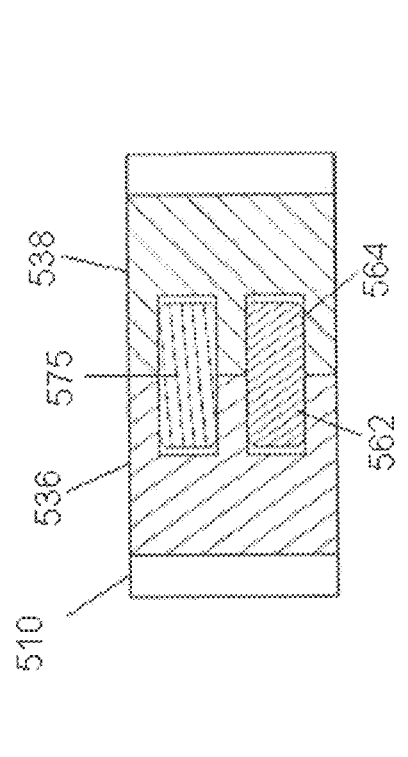
FIGS. 14A-14D illustrate different views of an alternative multi-piece allograft spacer to be used with the lower profile plates discussed above according to some embodiments.
Figure 14B:
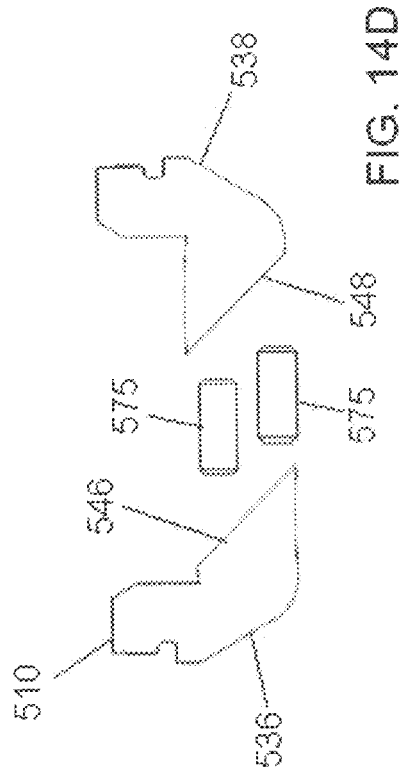
Figure 14C:
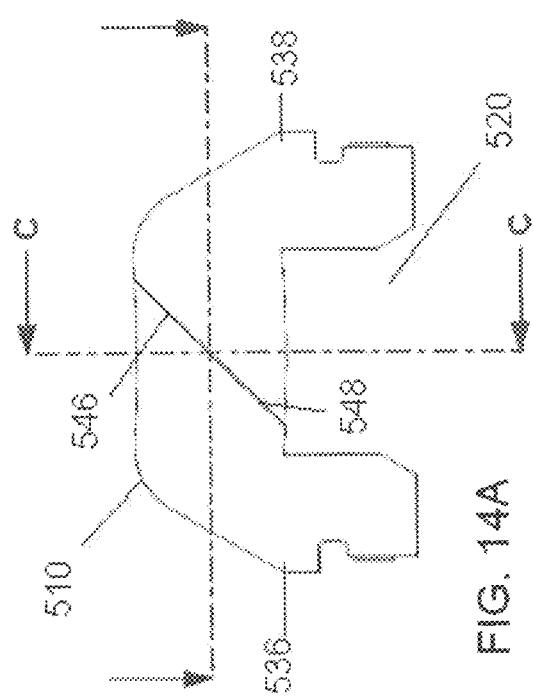
Figure 14D:
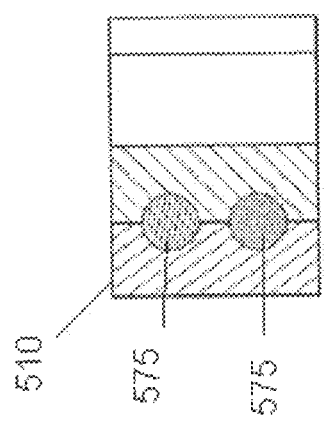

As shown best in FIG. 14A, the right interfacing surface 546 of the left member 536 is directly engaged with the left interfacing surface 548 of the right member 538. While the right interfacing surface 546 and the left interfacing surface 548 can be flat-on-flat, as both surfaces are planar, in some embodiments (as shown in FIG. 14A), the interface between the two surfaces is at an angle relative to the holes for receiving the pins 575. In other words, the pins 575 are received at an angle to the interface between the left member 536 and the right member 538. In addition, as shown in FIG. 14B, holes 562 and 564 need not go through the entirety of their respective members. In other words, one or more of the holes (e.g., holes 562, 564 or combined) can be blind holes, whereby the holes do not go through the left and right surfaces of the lateral implants.

By having multi-piece allograft spacers that are either stacked or aligned side-by-side, it is possible to have spacers of increased height and width. While the embodiments herein show two piece spacers, one skilled in the art will appreciate that three or more members can be combined to form multi-piece allograft spacers for use with any of the plate members described above.

FIGS. 15A-15D illustrate different views of an alternative low profile plate attached to a spacer according to some embodiments. The plating system 605 comprises a plate 650 attached or mounted to a spacer 610.

The system 605 includes a number of similar features to prior embodiments. The spacer 610 includes a body having an upper surface 612 and a lower surface 614 with texturing (e.g., ribs, grooves, teeth, protrusions) and sidewalls including one or more notches 617 for receiving plate extensions. The body of the spacer 610 can be U-shaped or C-shaped, such that a central portion includes a graft opening 620 for receiving graft material therein. The plate 650 includes a body having a first screw hole 652 for receiving a first screw member therethrough, a second screw hole 654 for receiving a second screw member therethrough, and a recess for receiving a blocking fastener or set screw 656. In addition, a pair of extension arms or members 670 extend from the plate body and are received in each of the notches 617 formed in the spacer 10. Each of the extension members 617 includes a window 672 for receiving a hump portion or region of the spacer to further secure the spacer 610 with the plate 650. In addition, the plate member 650 can include one or more stabilizers or knife-like edges 663 that can help secure the plate member 650 to a vertebral body. While the stabilizers 663 are shown as sharp and pointed, in other embodiments, the stabilizers 663 are more blunt and in some cases, even slightly rounded.

Figure 15A:
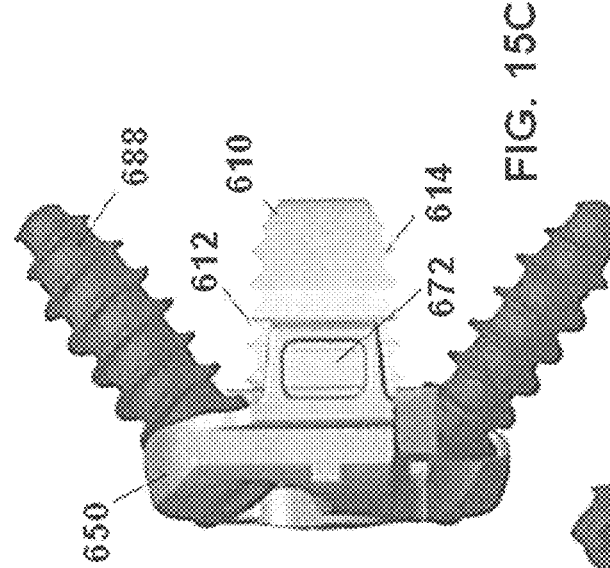
FIGS. 15A-15D illustrate different views of an alternative low profile plate attached to a spacer according to some embodiments.
Figure 15B:
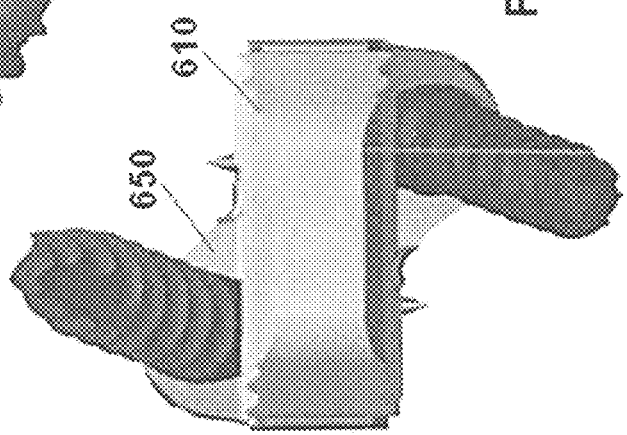
Figure 15C:
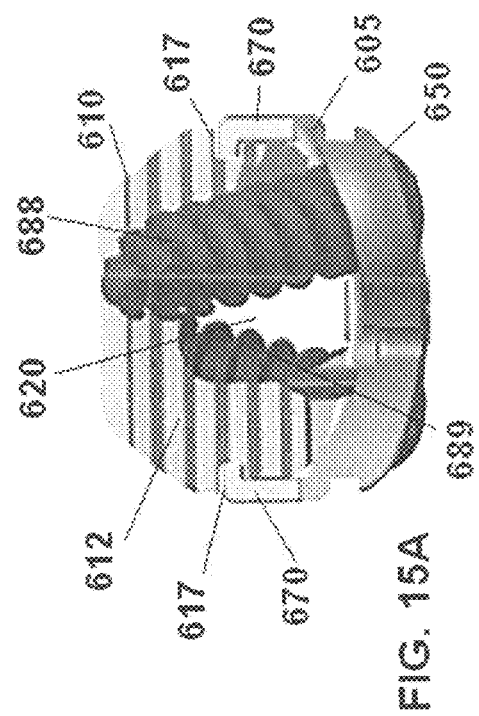
Figure 15D:
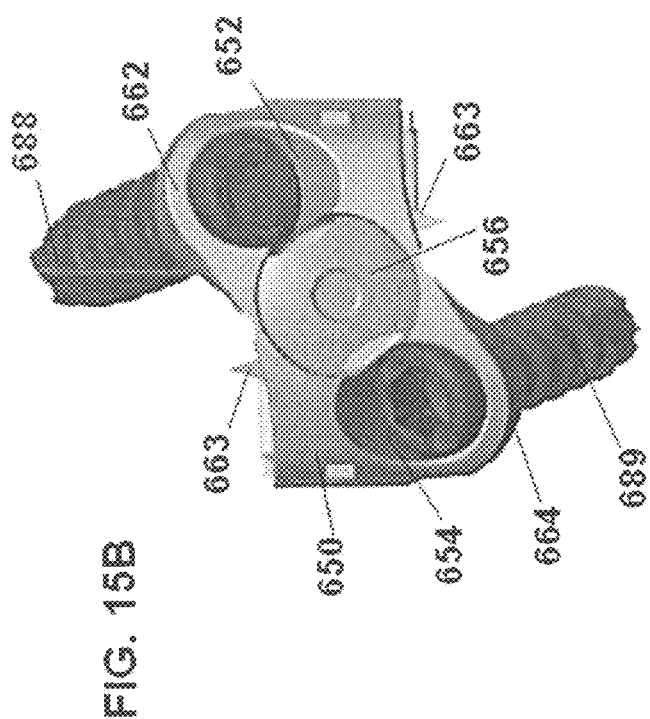

The plating system 605 in FIGS. 15A and 15D is unique in that the first upper screw hole 652 has been raised such that a central axis of the first upper screw hole 652 is positioned higher than the upper surface 612 of the spacer 610. In addition, the second lower screw hole 654 has been lowered such that a central axis of the second lower screw hole 654 is positioned below the lower surface 614 of the spacer 610. As shown in FIG. 15B, each of the holes 652, 654 has an adjacent brow member that extends from the plate body. First screw hole 652 is adjacent upper brow member 662, while second screw hole 654 is adjacent lower brow member 664. Upper brow member 662 has been raised to accommodate the raised upper screw hole 652, while lower brow member 664 has been lowered to accommodate the lowered lower screw hole 654.

Advantageously, by raising the upper screw hole 652 and lowering the lower screw hole 654, this reduces the likelihood of any viewing obstruction that may occur from the spacer 610. Moreover, even though the upper brow member 662 is raised and the lower brow member 664 is lowered, advantageously, the plating system 605 still maintains a low profile such that most if not all of the plate system remains in a disc space. In other embodiments, it may be desired for a part of the upper brow member 662, a part of the lower brow member 664 or both to contact a vertebral face (e.g., an anterior face), thereby providing stability to the plating system 605.

FIGS. 16A-16D illustrate different views of a plate member 650 used in the plating system 605. From these views, one can clearly see how the upper brow member 662 and first upper hole member 652 have been raised, while the lower brow member 664 and second lower hole member 654 have been lowered, relative to other designs. In some embodiments, the entire central axis of first upper hole member 652 (e.g., from a front of the plate member 650 to a back of the plate member 650) is continuously above the upper surface of the spacer, thereby advantageously providing a less unobstructed view of the first upper hole member 652. Likewise, in some embodiments, the entire central axis of the second lower hole member 654 (e.g., from a front of the plate member 650 to a back of the plate member 650) is continuously below the lower surface of the spacer, thereby advantageously providing a less unobstructed view of the second lower hole member 654.

Figure 17A:
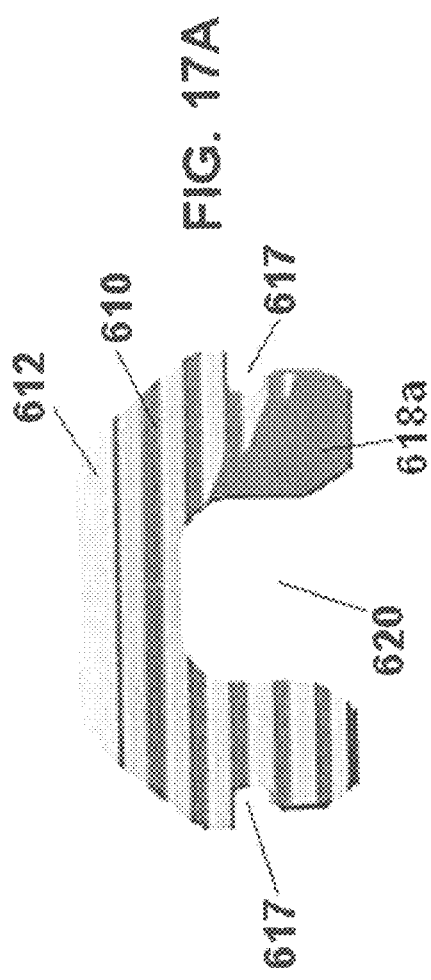
FIGS. 17A-17C illustrate different views of a spacer shown in FIGS. 15A-15D.
Figure 17C:
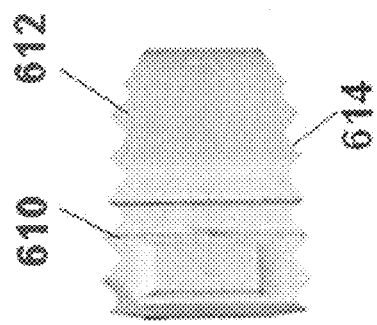
Figure 17B:
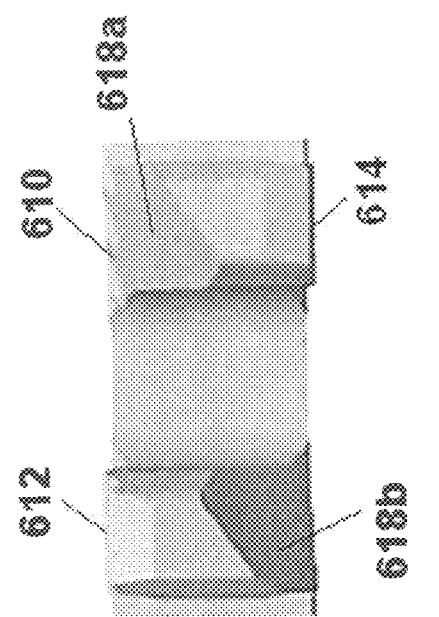

FIGS. 17A-17C illustrate different views of a spacer 610 used in the plating system 605. From these views, one can clearly see features of the spacer 610 includes its upper surface 612, lower surface 614, sidewalls with notches 617 and graft opening 620. In addition, with the plate member removed from the views, one can also see an upper chamfer 618a and a lower chamfer 618b that are cut into the spacer 610. These chamfers 618a, 618b advantageously provide clearance for bone screws that are inserted through the plating system 605. One skilled in the art will appreciate that the spacer can be made of many different materials. In some embodiments, the spacer will be made out of bone (e.g., allograft), while in other embodiments, the spacer will be made of PEEK. Advantageously, the plating system 605 is removably attached to the spacer 610 such that a surgeon can choose to include a spacer of a certain material as so desired during a surgical procedure.

FIGS. 18A-18D illustrate different views of yet another plate system involving a plate member and a spacer having a unique multi-piece composition in accordance with some embodiments. The plate system 705 includes similar elements as found in prior embodiments, including a plate member 750 having a first upwardly oriented screw hole 752 for receiving a first screw, a second downwardly oriented screw hole 754 for receiving a second screw, and a blocking member or screw 756, as well as a spacer 710 (e.g., allograft or PEEK) having an upper surface 712, a lower surface 714, a graft opening 720, and notches 717 for receiving arms or extensions 770 of the plate member 750. The plate member 750 also includes one or more windows 772 in its extensions 770 for receiving a raised or bump out portion of the spacer 705, thereby helping to retain the spacer 705 within the plate member 750. In addition, the plate member 750 includes stabilizers 763 in the form of knife-like edges that help to grip into a vertebral body.

In addition to these features, the spacer 710 has a unique multi-piece composition. As shown in FIGS. 18A and 18D, in some embodiments, the spacer 710 has a body formed of two adjacent members—a first member 711 and a second member 713. The first member 711 and the second member 713 can be held together via one or more pin members, although in other embodiments, the first member 711 and second member 713 can be held via adhesive, mateable connections, etc. As shown in FIG. 18D, second member 713 can include an upper overhang region 717 that hangs over a part of the first member 711. Similarly, first member 711 can include a lower overhang region 711 that hangs below a part of the second member 713. Advantageously, these overhang regions 711 serve as guides to identify the location of the interface 715 between the first member 711 and the second member 713. During manufacturing, the overhang regions 711 make it easy to inspect the interface to 715 to ensure that the two members 711, 713 are properly secured together. While the illustrated embodiment shows a spacer 710 having two separate overhanging regions, in other embodiments, the spacer 710 can have one single overhanging region. As before, the spacer 710 can be made of many different types of materials, including bone (e.g., allograft) and PEEK), and a surgeon can advantageously decide what type of spacer should accompany the plate before or during surgery.

FIG. 19 shows a plating system 805 having a plate member 850 having extensions 870 and a spacer 810 similar to that found in FIGS. 18A-18D; however, the spacer 810 is designed to accommodate lordosis. In other words, while the upper surface 712 and lower surface 714 of the spacer 710 can be substantially parallel (as shown in FIG. 18C), the upper surface 812 and lower surface 814 of the spacer 810 can have some degree of angulation or lordosis. In some embodiments, relative to a mid-line of the spacer 810, the upper surface 812 and/or lower surface 814 can have a degree of angulation of 2, 3, 5, 7, 12 degrees or more. Advantageously, the lordotic spacer 810 (which is accompanied with the plate member 850) helps to accommodate different anatomies.

FIGS. 20A-20D show yet another alternative plating system having a plate member attached to multiple spacers in accordance with embodiments of the present application. The unique plating system 905 comprises a plate member 950 having a pair of inner arms or extensions 975 and a pair of outer arms or extensions 970 for receiving one or more spacers 910 therein. In some embodiments, both the inner and outer extensions 975, 970 include protruding portions designed to be received in notches in the one or more spacers.

Figure 21A:
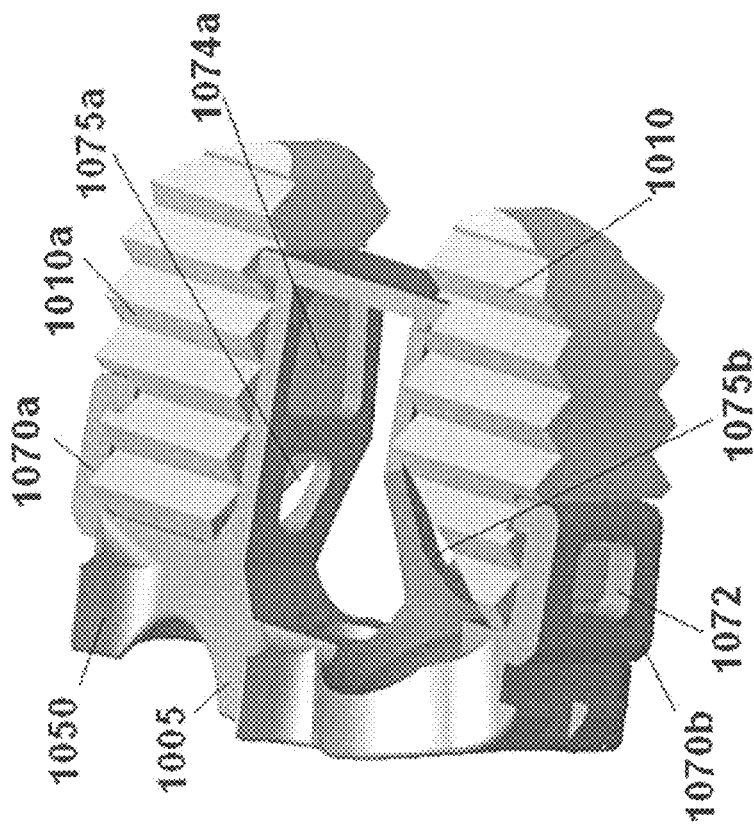
FIGS. 21A and 21B illustrate different views of another alternative low profile plate attached to multiple spacers according to some embodiments.
Figure 21B:
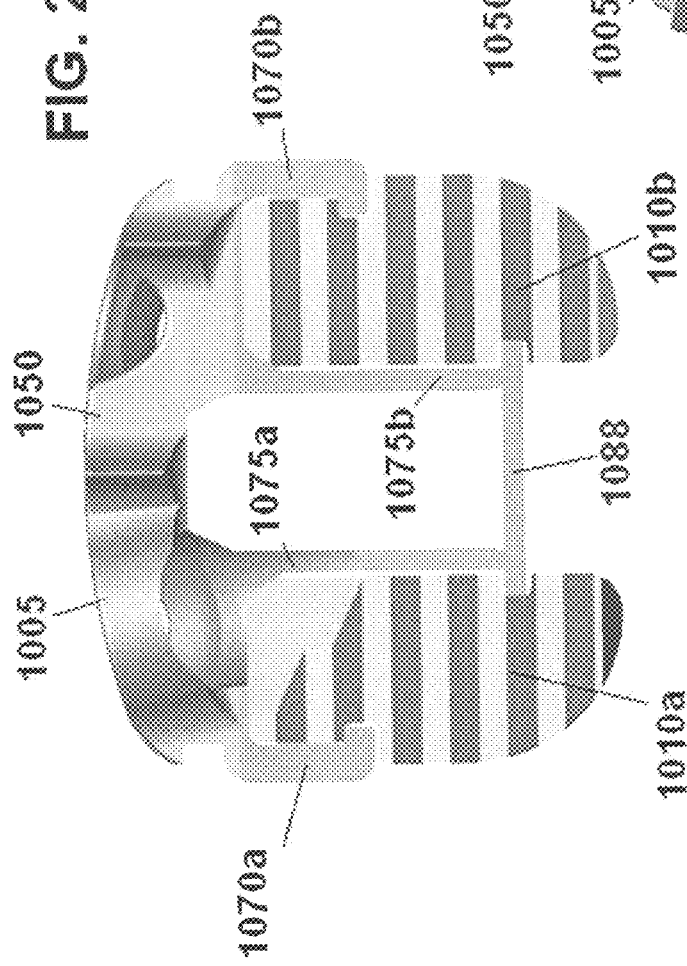
Figure 26B:
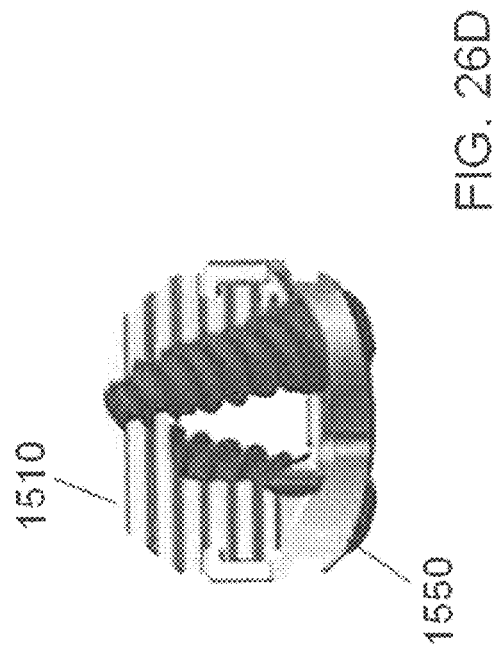
FIGS. 26A-26D illustrate another alternative plate having raised and lowered screw openings in attachment with a spacer according to some embodiments.
Figure 26A:
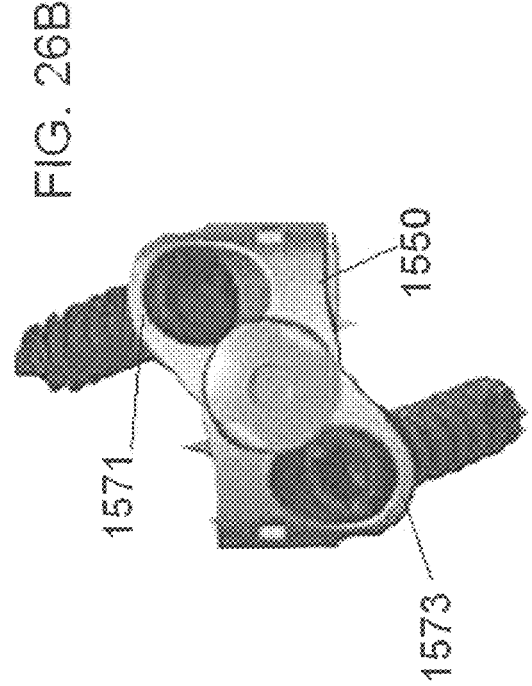
Figure 26D:
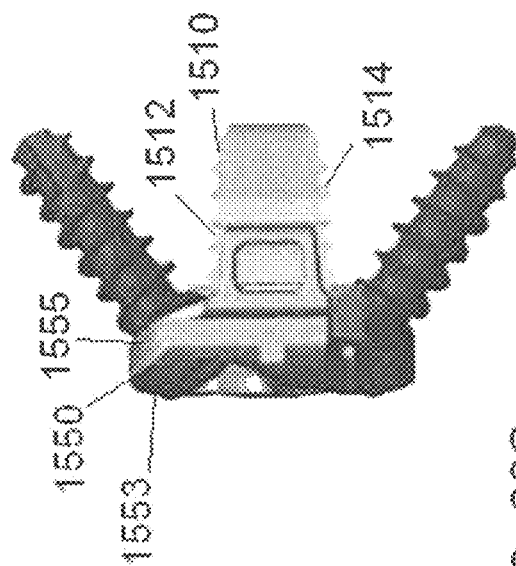
Figure 26C:
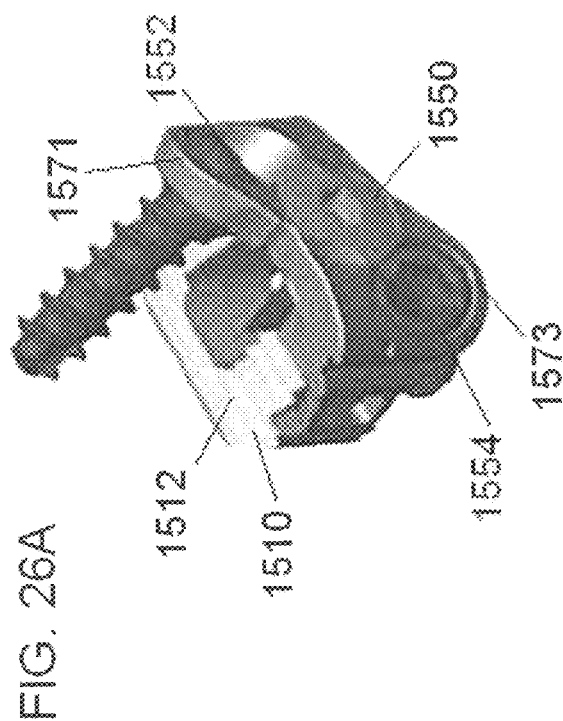
Figure 27B:
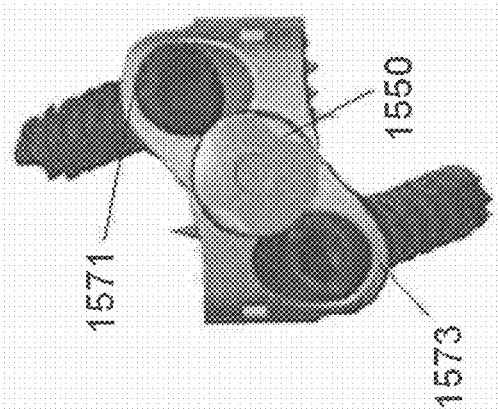
FIGS. 27A-27D illustrate another alternative plate having raised and lowered screw openings in attachment with a spacer according to some embodiments.
Figure 27A:
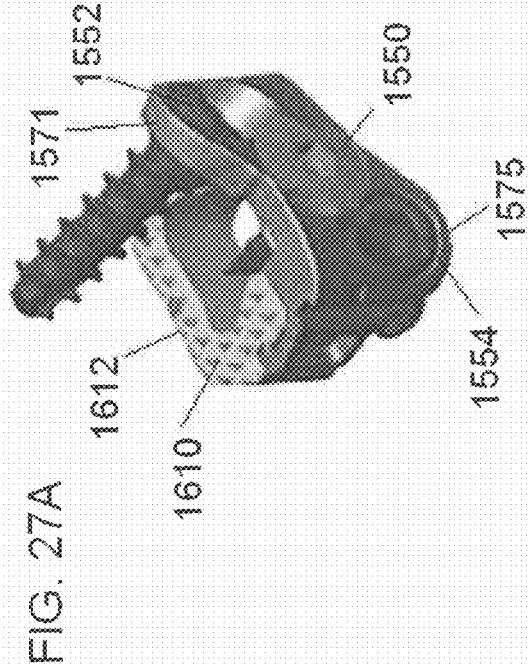
Figure 27D:
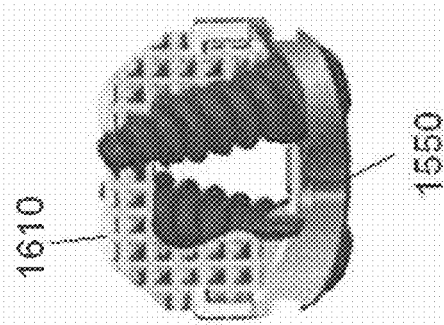
Figure 27C:
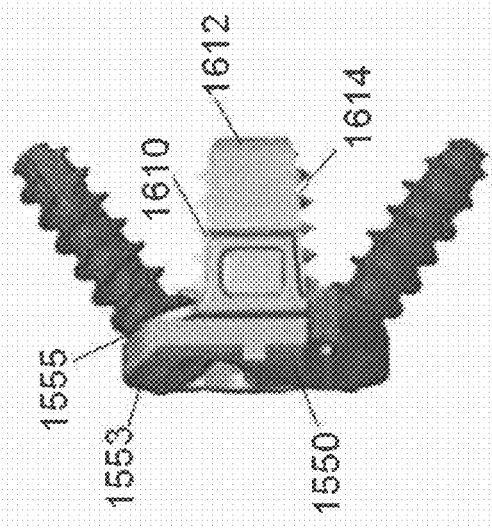

As shown in FIG. 20A, the plating system 905 includes a first spacer 910a that is retained between a shorter outer extension 970 and a longer inner extension 975 of the plate member 950. The shorter outer extension 970 of the plate is configured to be received in notch 917 of the spacer 910a, while the longer inner extension 975 of the plate is configured to be received in notch of the spacer 910a. In addition, advantageously, the shorter outer extension 970 includes a window 972 and the longer inner extension 975 includes a window 974. Each of the windows 972, 974 is configured to receive a bump out portion of the spacer 910, thereby helping to retain the spacer 910 to the plate member 905. In addition, the windows 972, 974 help to provide a means to visualize fusion (e.g., in a lateral image) that is occurring once the spacer is implanted within a disc space. Similarly, the plating system 905 includes a second spacer 910b that is retained between a shorter outer extension 970 and a longer inner extension 975 on an opposite side of the plate member 950. While in the present embodiment, each of the longer inner extensions 975 is separated from the other without any connecting member, in other embodiments, a connection bar or bridge (such as shown in FIGS. 21A and 21B) can extend between the two inner extensions 975. Advantageously, when the plating system 905 is placed in a disc space, graft material can be packed between the two inner extensions 975 to promote fusion within the disc space.

Advantageously, in accordance with some embodiments, the plating system 905 is designed to hold at least two spacers 910a, 910b. In some embodiments, the spacers 910a, 910b are substantially rectangular pieces. In some embodiments, the spacers 910a, 910b can have substantially rounded edges. In some embodiments, the spacers 910a, 910b can include one or more chamfers 918 for providing clearance for one or more screws that are inserted through the plate member 905. For example, spacer 910a can include a chamfer that provides clearance for a screw that passes through plate opening 954, while spacer 910b can include a chamfer that provides clearance for a screw that passes through plate opening 952. Advantageously, the use of two spacers 910a, 910b—one on each side of the plate system 905—helps to stabilize the plate system within the disc space. Moreover, having multiple individual spacers 910a, 910b that are smaller in size can ease manufacturing issues, as the spacers can be formed of relatively small pieces of bone, which can be easier to find than larger pieces of bone. In other words, bone that is removed from a body can improve the yield of production, as it will be easier to create the spacer members. While the spacers 910a, 910b are illustrated as being single-bodied members in the present embodiments, in other embodiments, the spacers can be formed of multiple pieces (e.g., pinned together).

FIGS. 21A and 21B illustrate different views of another alternative low profile plate attached to multiple spacers according to some embodiments. The plate system 1005 comprises a plate member 1050 attached to a pair of spacers 1010a and 1010b. Like the embodiment in FIG. 20A, the plate member 1050 of the present embodiment includes a pair of outer arms or extensions 1070a, 1070b and a pair of inner arms or extensions 1075a, 1075b. Plate extensions 1070a and 1075a are configured to retain spacer 1010a, while plate extensions 1070b and 1075b are configured to retain spacer 1010b. As shown in FIGS. 21A and 21B, the inner extensions 1075a and 1075b includes a connection or bridge member 1088 that extends between them. Advantageously, the bridge member 1088 helps provide added stability to the plate system 1005, and also helps provide a barrier to retain graft material within the plate system 1005. As shown in FIG. 21A, in some embodiments, the inner extensions 1075a and 1075b are parallel to one another.

As shown in FIG. 21B, outer plate extensions 1070a and 1070b include at least one window 1072 formed therein. Similarly, inner plate extensions 1075a and 1075b include at least one window formed therein. As shown in FIG. 21B, inner plate extensions each include two windows—1074 and 1075—that are formed adjacent to one another. Inner plate extension 1075a includes windows 1074a and 1075a, while inner plate extension 1075b includes windows 1074b and 1075b. In some embodiments, the windows 1072, 1074, 1075 can advantageously be designed to hold a bump out portion of the spacers and/or provide increased visualization to a surgeon during or after a fusion procedure. While in some embodiments, each of the windows 1072, 1074, and 1075 perform the same duties and functions, in other embodiments, the windows can perform different functions. For example, while inner window 1074 can be used to both retain the spacer and aid in fusion visualization, inner window 1075 can be used simply for fusion visualization.

FIG. 22 illustrates another alternative low profile plate attached to multiple spacers according to some embodiments. The plate system 1105 comprises a plate member 1150 attached to a pair of spacers 1110a and 1110b. Like the embodiment in FIG. 21A, the plate member 1150 of the present embodiment includes a pair of outer arms or extensions 1170a, 1170b and a pair of inner arms or extensions 1175a, 1175b. Plate extensions 1170a and 1175a are configured to retain spacer 1110a, while plate extensions 1170b and 1175b are configured to retain spacer 1110b. As shown in FIGS. 21A and 21B, the inner extensions 1175a and 1175b includes a connection or bridge member 1188 that extends between them. Advantageously, the bridge member 1188 helps provide added stability to the plate system 1105, and also helps provide a barrier to retain graft material within the plate system 1105. In contrast to the inner extensions 1075a, 1075b in FIG. 21A, the inner extensions 1175a, 1175b are non-parallel and angulated relative to one another. Furthermore, due to the shape of the plate member 1150, the shapes of the individual spacers 1110a and 1110b differ in that they have a prominent angled surface adjacent to the inner extensions 1175a, 1175b.

FIG. 23 illustrates another alternative low profile plate attached to multiple spacers according to some embodiments. The plate system 1205 comprises a plate member 1250 attached to a pair of spacers 1210a and 1210b. Like the embodiment in FIG. 22, the plate member 1250 of the present embodiment includes a pair of outer arms or extensions 1270a, 1270b and a pair of inner arms or extensions 1275a, 1275b. Plate extensions 1270a and 1275a are configured to retain spacer 1210a, while plate extensions 1270b and 1275b are configured to retain spacer 1210b. As shown in FIGS. 23, the inner extensions 1275a and 1275b includes a connection or bridge member 1288 that extends between them. Advantageously, the bridge member 1288 helps provide added stability to the plate system 1205, and also helps provide a barrier to retain graft material within the plate system 1205. In contrast to the bridge member 1188 in FIG. 22, the bridge member 1288 is elongated and extends to a distal end of the spacers 1210a, 1210b, thereby creating an even larger space for receiving graft material in the middle of the plate system 1205.

FIGS. 24A-24C illustrate another alternative low profile plate attached to multiple spacers according to some embodiments. The plate system 1305 comprises a plate member 1350 attached to a multi-piece spacer 1310 formed of three members 1310a, 1310b, 1310c. Like the embodiment in FIG. 23, the plate member 1350 of the present embodiment includes a pair of outer arms or extensions 1370a, 1370b and a pair of inner arms or extensions 1375a, 1375b connected by a bridge member 1388. The inner extensions 1375a, 1375b and bridge member 1388 are configured to be enclosed by the body of the spacer 1310. Advantageously, the bridge member 1388 helps provide added stability to the plate system 1305, and also helps provide a barrier to retain graft material within the plate system 1305.

In some embodiments, the spacer 1310 is formed of three different members 1310a, 1310b, 1310c. The members 1310a and 1310b can be outer members which bound the inner member 1310c. As shown in FIG. 24C, the members 1310a and 1310b can be substantially similar, and can include upper and lower surfaces with surface protrusions to enable better gripping of bone. Inner member 1310c can be different from the other members and can include a relatively smooth surface without surface protrusions. In addition, the inner member 1310c can be of a different height than the other members. In some embodiments, the three members 1310a, 1310b, 1310c are pinned together, while in other embodiments, they can be joined together via an adhesive or mateable connection. Advantageously, the addition of the inner member 1310c provides further support to the overall structure of the plate system 1305.

FIGS. 25A and 25B illustrate another alternative low profile plate attached to a multi-piece spacer having a metal insert according to some embodiments. The plate system 1405 comprises a plate member 1450 attached to a multi-piece spacer 1410 formed of two similar components 1410a, 1410b and a metal insert 1439. The plate member 1450 can include a first screw opening, a second screw opening and a rotatable locking mechanism 1456 to prevent back out of screws that are inserted through the openings. In some embodiments, the plate member 1450 of the present embodiment is mounted to the front of the spacer. In other embodiments, the plate member 1450 includes a pair of outer arms or extensions and/or a pair of inner arms or extensions (not shown) to help retain the spacer 1410 within the plate member 1450.

In some embodiments, the spacer 1410 is formed of two members 1410a and 1410b separated by a metal insert 1439. These members partially enclose a graft opening 1420. The two members 1410a and 1410b can be formed of a material different from the metal insert 1439, such as PEEK. Advantageously, the metal insert 1439 is designed to provide additional strength to the spacer 1410. In some embodiments, the metal insert 1439 is formed of titanium. As shown in the exploded view in FIG. 25B, the spacer 1410 be attached to the plate member 1450 via vertical fastening members 1429a, 1429b. One skilled in the art will appreciate that the spacer 1410 can be used with any of the other plate members discussed above.

Figure 28:
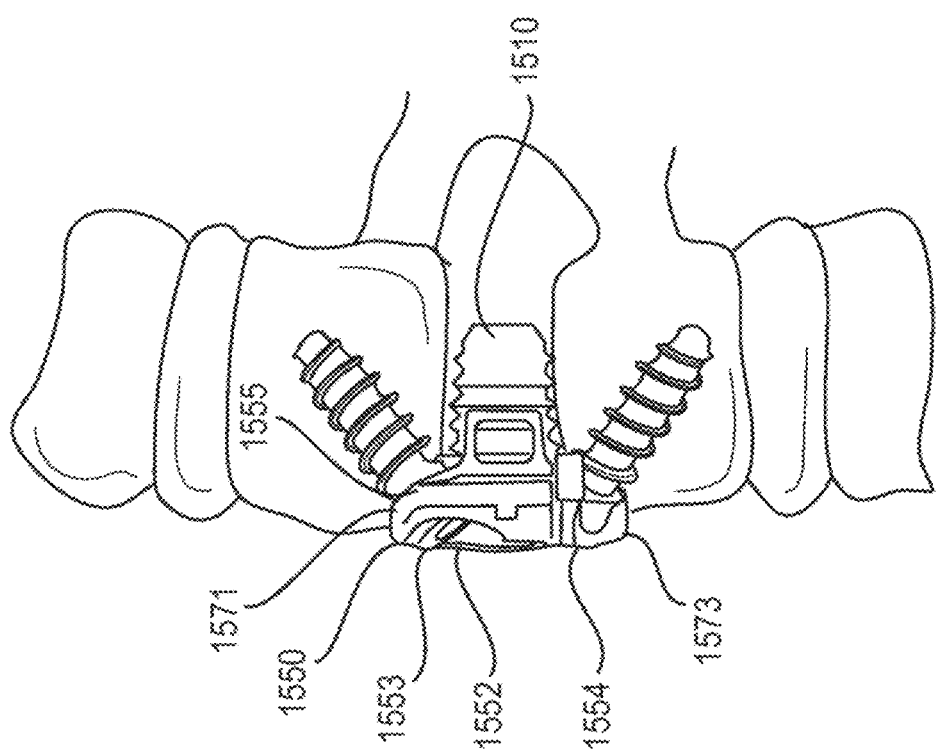
FIG. 28 illustrates the plate and spacer in FIGS. 26A-26D in use within a vertebral space.
Figure 30B:
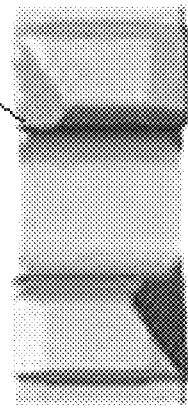
FIGS. 30A-30E illustrate different views of an allograft spacer that can be used with the plate in FIGS. 26A-26D.
Figure 30A:
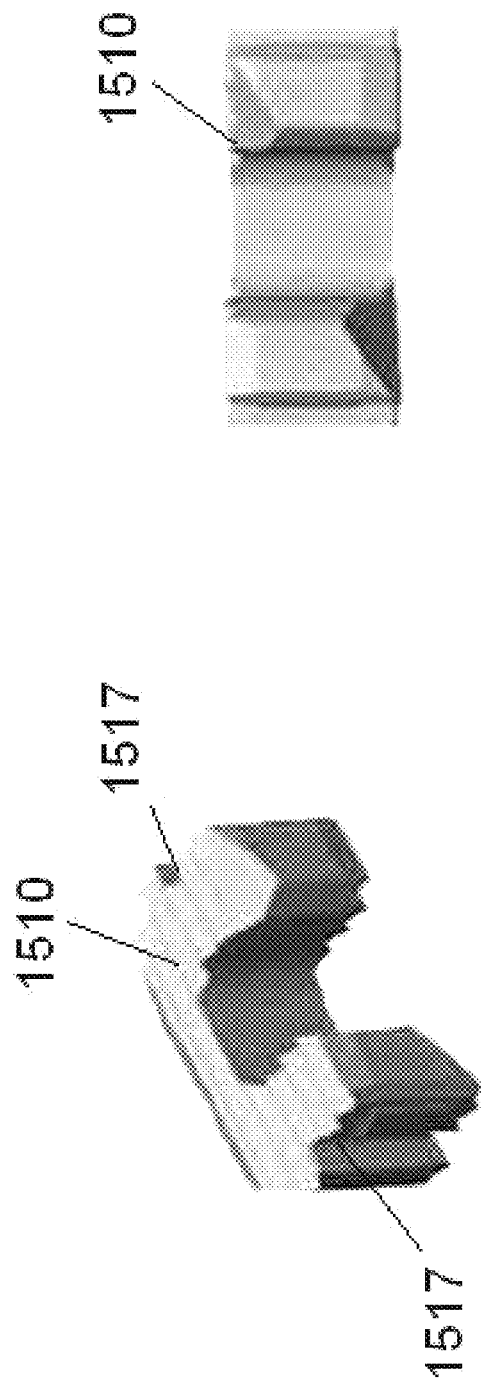
Figure 30C:
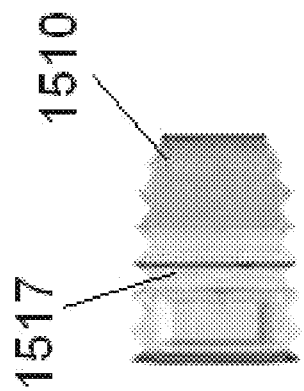
Figure 30D:
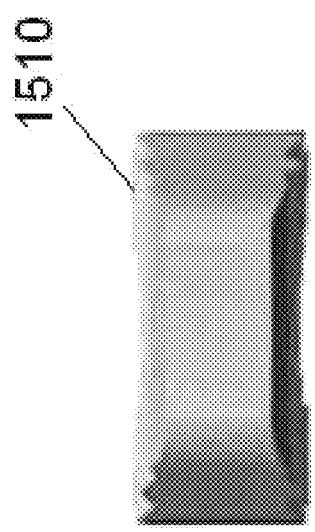
Figure 30E:
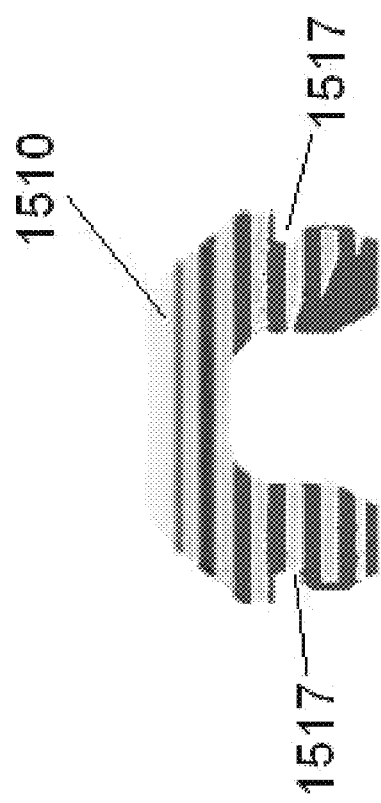
Figure 31B:
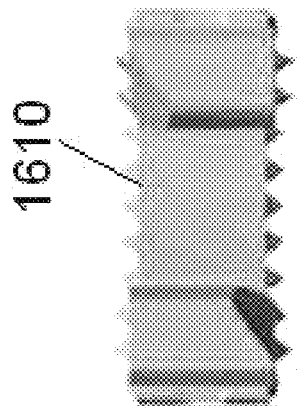
FIGS. 31A-31E illustrate different views of a PEEK spacer that can be used with the plate in FIGS. 26A-26D.
Figure 31C:
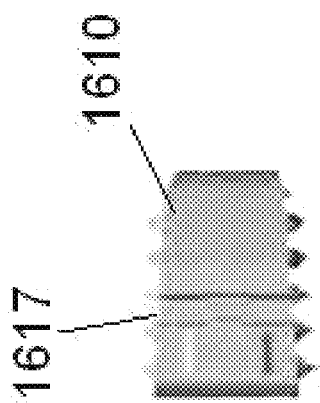
Figure 31A:
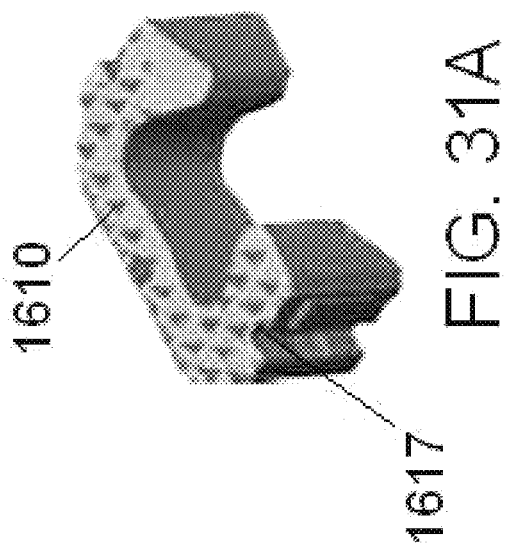
Figure 31D:
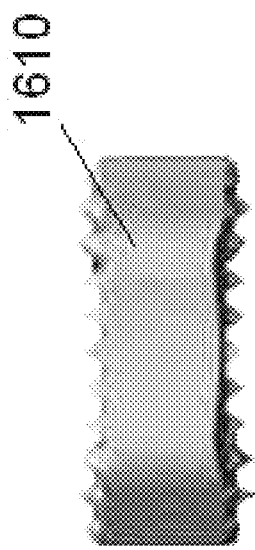
Figure 31E:
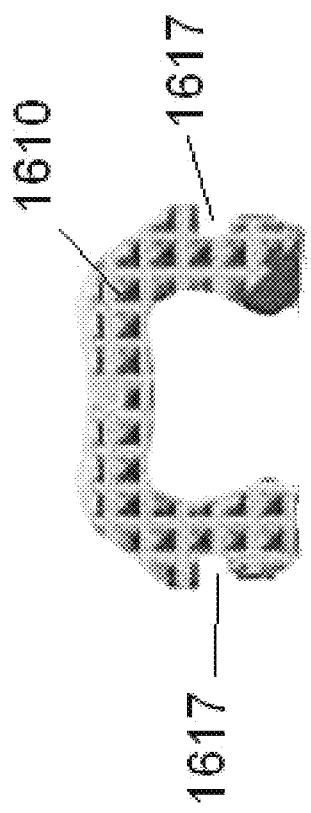
Figure 33:
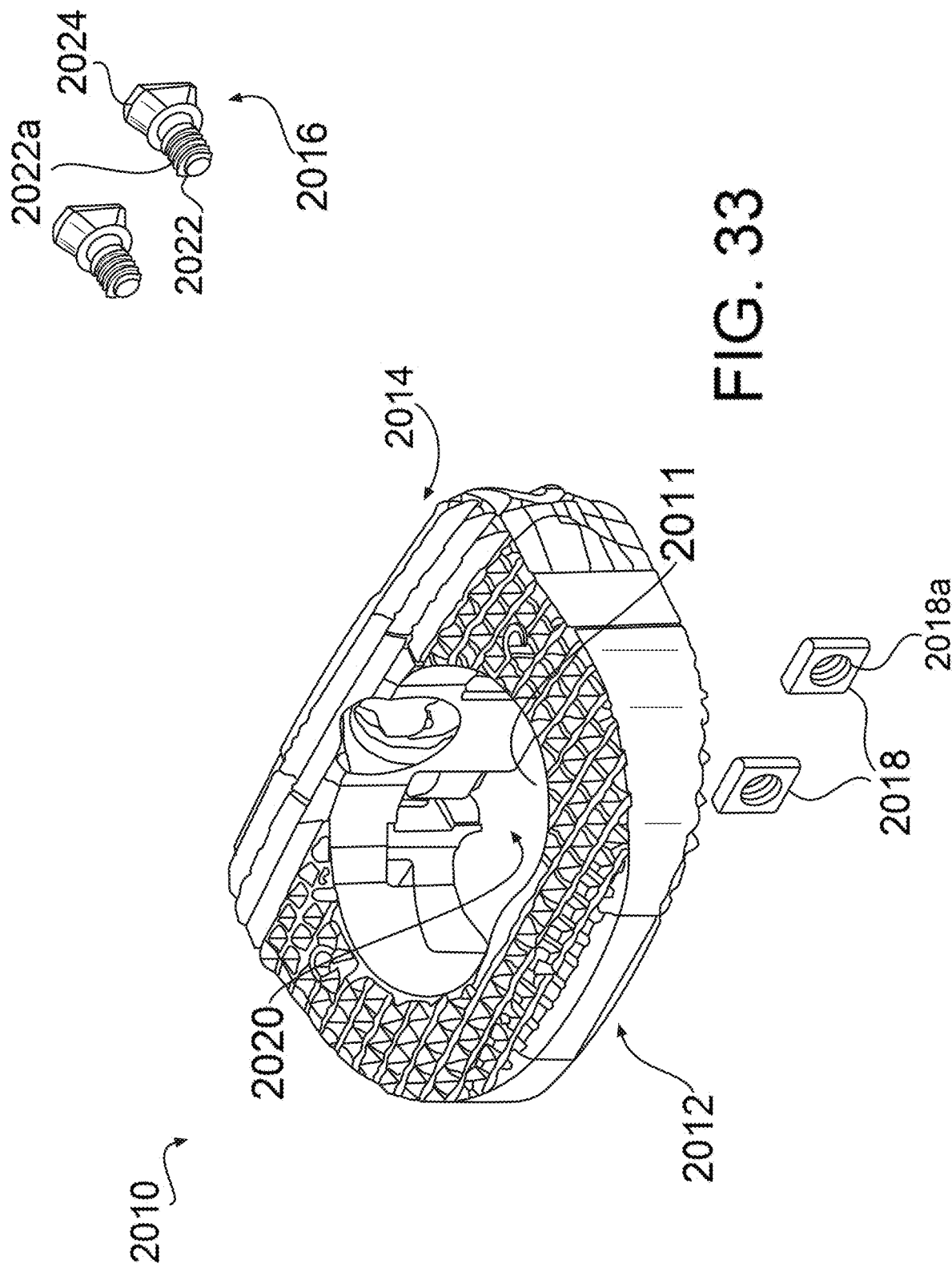
Figure 35:
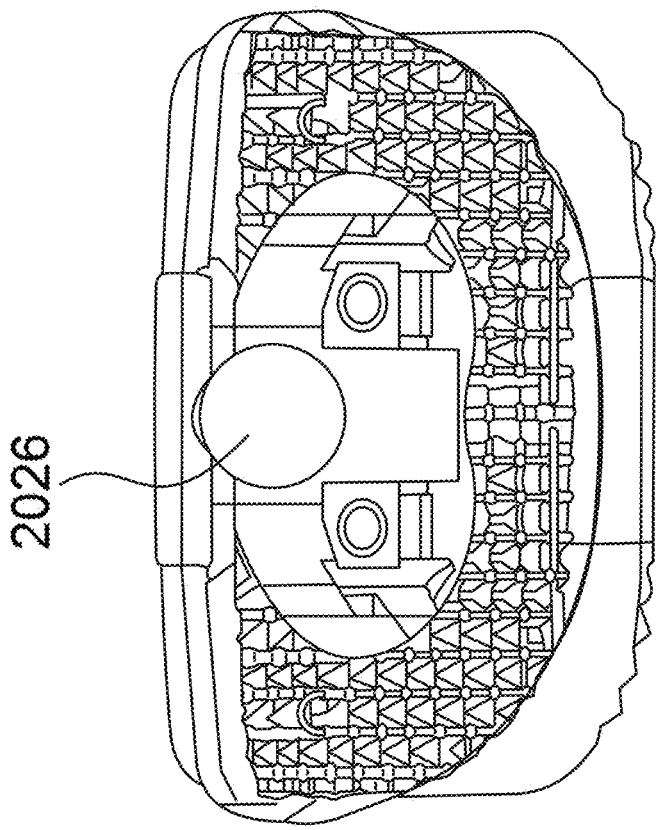
Figure 36:
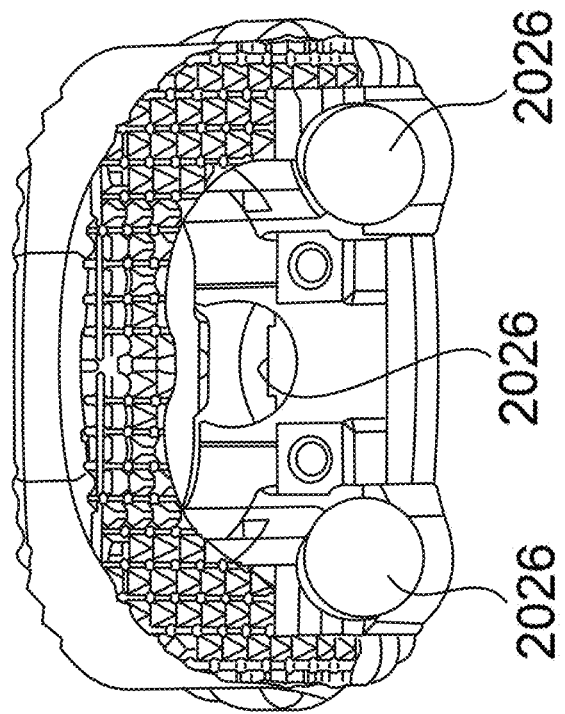
Figures 37, 38:
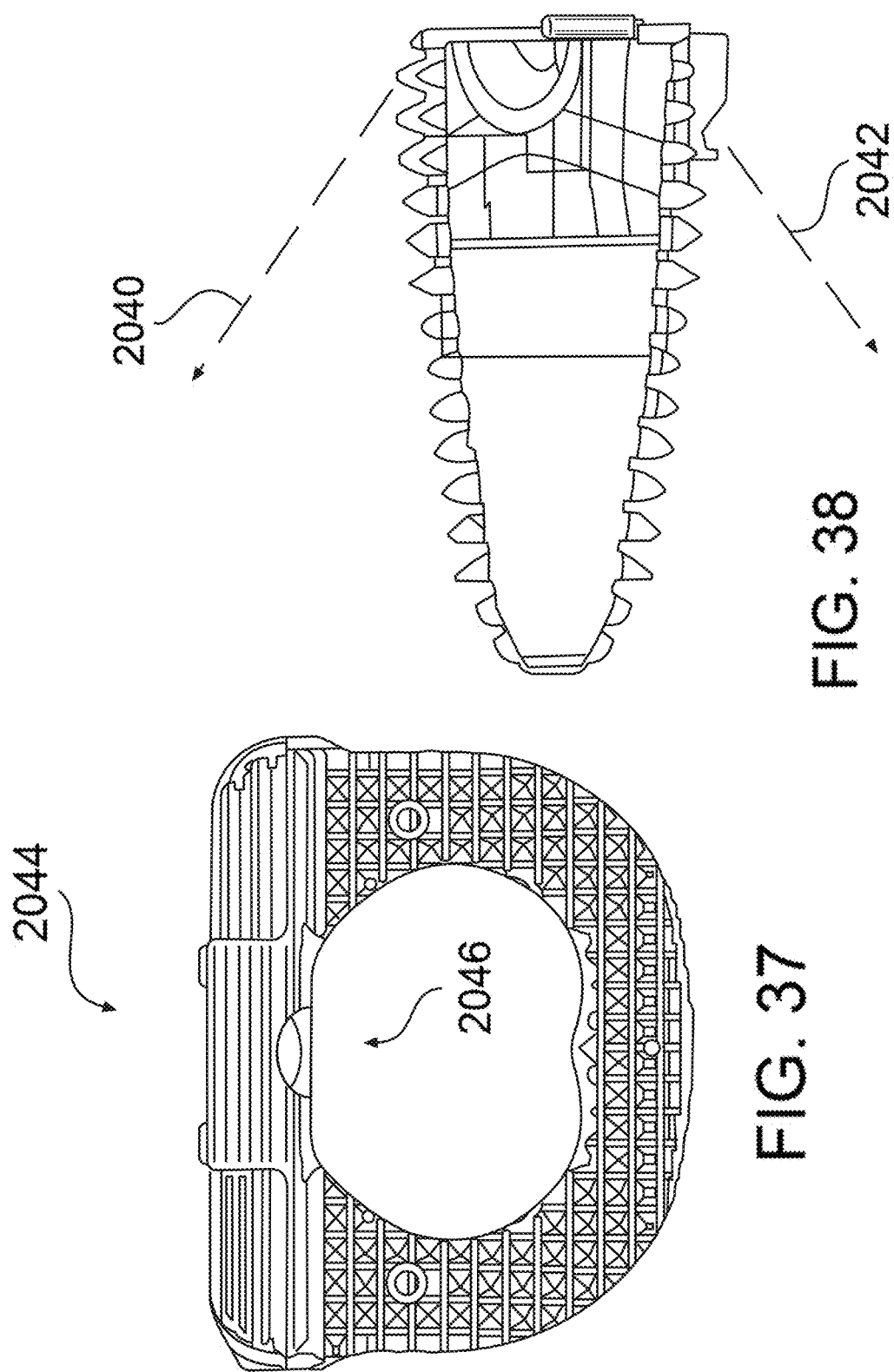

FIGS. 26A-26D illustrate another alternative plate having raised and lowered screw openings in attachment with a spacer according to some embodiments. The plate 1550 and spacer 1510 have many similar features as in prior embodiments; however, the upper screw hole 1552 in the plate 1550 has been raised, while the lower screw hole 1554 in the plate 1550 has been lowered. The upper screw hole 1552 has been raised such that a center axis of the upper screw hole 1552 is positioned entirely above an upper surface 1512 of the spacer 1510. The lower screw hole 1554 has been lowered such that a center axis of the lower screw hole 1554 is positioned entirely below a lower surface 1514 of the spacer 1510. Advantageously, by raising the upper screw hole 1552 such that a center axis extends completely above the upper surface 1512 of the spacer 1510, this provides a plate member 1550 having increased visibility on its upper end and also provides an upper plate portion that can be uniquely positioned relative to a disc space, as shown in FIG. 28. Likewise, by lowering the lower screw hole 1554 such that a center axis extends completely below the lower surface 1514 of the spacer 1510, this provides a plate member 1550 having increased visibility on its lower end and also provides a lower plate portion that can be uniquely positioned relative to a disc space, as also shown in FIG. 28.

In some embodiments, the plate 1550 and the spacer 1510 have many similar features as in prior embodiments. For example, the spacer 1510 is configured to have a body having an upper surface 1512 in contact with an upper vertebral body and a lower surface 1514 in contact with a lower vertebral body. The spacer body includes notches for receiving portions of the plate 1550 therein. In some embodiments, the spacer 1510 is formed of a natural material, such as allograft bone.

The plate 1550 includes the upper screw hole 1552 and the lower screw hole 1554, and a pair of arms or extensions that are designed to be received within the spacer 1510. As noted above, the upper screw hole 1552 has been raised such that a center axis that extends through the upper screw hole 1552 is positioned higher than an upper surface of the spacer 1510. In some embodiments, only a portion of the center axis through the upper screw hole 1552 is positioned higher than an upper surface of the spacer 1510, while in other embodiments, the entire center axis through the upper screw hole 1552 is positioned higher than an upper surface of the spacer 1510. Likewise, the lower screw hole 1554 has been lowered such that a center axis that extends through the lower screw hole 1554 is positioned lower than a lower surface of the spacer 1510. In some embodiments, only a portion of the center axis that passes through the lower screw hole 1554 is positioned lower than a lower surface of the spacer 1510, while in other embodiments, the entire center axis through the lower screw hole 1552 is positioned lower than a lower surface of the spacer 1510.

In some embodiments, the plate 1550 includes an upper extension, eyelid or rim 1571 through which the upper screw hole 1552 can pass through. In some embodiments, the upper rim 1571 has an anterior or front face 1553 and a posterior or back face 1555 (identified in FIG. 26C). In some embodiments, both the front face 1553 and the rear face 1555 of the upper rim 1571 are straight and vertical and not angled relative to height of vertical axis of the spacer. In other embodiments, either the front face 1553 or the rear face 1555 can be straight, while the other face can be angled (e.g., in an anterior direction). In yet other embodiments, both the front face 1553 and the rear face 1555 of the upper rim 1571 can be angled. Advantageously, in some embodiments, the upper screw hole 1552 extends through the upper rim 1571 at an angle such that a screw that is inserted through the upper screw hole 1552 will be inserted at or near a corner edge of an upper vertebral body (as shown in FIG. 28). By being positioned at or near a corner edge of the upper vertebral body, it is not necessary for the screw to be positioned through an anterior face or aspect of the upper vertebral body, thereby maintaining a low profile implant. In some embodiments, the majority or entirety of the upper rim 1571 including the upper screw hole 1552 can be configured such that the upper portion of the plate rests at or near a corner edge of the upper vertebral body, thereby maintaining a low profile implant.

In some embodiments, the plate 1550 includes a lower extension, eyelid or rim 1573 through which the lower screw hole 1554 can pass through. In some embodiments, the lower rim 1573 has an anterior or front face 1553 and a posterior or back face 1555 (identified in FIG. 29A). In some embodiments, both the front face 1553 and the rear face 1555 of the lower rim 1573 are straight and vertical and not angled relative to height of vertical axis of the spacer. In other embodiments, either the front face 1553 or the rear face 1555 can be straight, while the other face can be angled (e.g., in an anterior direction). In yet other embodiments, both the front face 1553 and the rear face 1555 of the lower rim 1573 can be angled. Advantageously, in some embodiments, the lower screw hole 1554 extends through the lower rim 1573 at an angle such that a screw that is inserted through the lower screw hole 1554 will be inserted at or near a corner edge of a lower vertebral body (as shown in FIG. 28). By being positioned at or near a corner edge of the lower vertebral body, it is not necessary for the screw to be positioned through an anterior face or aspect of the upper vertebral body, thereby maintaining a low profile implant. In some embodiments, the majority or entirety of the lower rim 1573 including the lower screw hole 1554 can be configured such that the lower portion of the plate rests at or near a corner edge of the lower vertebral body, thereby maintaining a low profile implant. Advantageously, in some embodiments, at least a portion of the upper rim 1571 and/or a portion of the lower rim 1573 is maintained within the disc space between the upper vertebral body and the lower vertebral body, thereby maintaining an implant with a low profile.

FIGS. 27A-27D illustrate another alternative plate having raised and lowered screw openings in attachment with a spacer according to some embodiments. The plate 1550 and the spacer 1610 are similar to the assembly in FIGS. 26A-26D, except the spacer 1610 is formed of a different material, such as PEEK. Advantageously, the plate 1550 is capable of being assembled with either the bone spacer 1510 shown in FIGS. 26A-26D or the PEEK spacer 1610 shown in FIGS. 27A-27D prior to insertion into a disc space, thereby providing versatility to a surgeon.

FIG. 28 illustrates the plate and spacer in FIGS. 26A-26D in use within a vertebral space. From this view, one can see how the plate 1550 is designed to have an upper rim 1571 that accommodates an upper screw hole 1552 and a lower rim 1573 that accommodates a lower screw hole 1554. The upper screw hole 1552 receives an upwardly angled screw that is configured to be inserted at or near a corner of the upper vertebral body, thereby avoiding insertion through an anterior face or aspect of the upper vertebral body. The lower screw hole 1554 receives a downwardly angled screw that is configured to be inserted at or near a corner of the lower vertebral body, thereby avoiding insertion though an anterior face or aspect of the lower vertebral body.

FIGS. 29A-29C illustrate the plate in FIGS. 26A-26D without a spacer. As shown in these figures, the plate 1550 includes an upper rim 1571 that accommodates an upwardly angled screw hole 1552 and a lower rim 1573 that accommodates a downwardly angled screw hole 1554. The upper rim 1571 includes a front or anterior face 1553a and a rear or posterior face 1555a, while the lower rim 1573 includes a front or anterior face 1553b and a rear or posterior face 1555b. As shown in FIG. 29B, in some embodiments, the entire anterior face of the plate (e.g., including the upper anterior face of the upper rim 1571 and the lower anterior face of the lower rim 1573) can be straight and non-angled. In other embodiments, portions of the anterior face can be slightly angled, such as in an anterior direction. In addition, as shown in FIG. 29B, in some embodiments, portions of the posterior faces of the plate (e.g., posterior faces 1555a and 1555b) can also be straight and non-angled. In other embodiments, portions of the posterior faces can be angled (e.g., in an anterior direction), such as 5 degrees, 10 degrees, 15 degrees, or more. In some embodiments, the anterior and/or posterior faces of the rims can be angled between 5 and 15 degrees.

FIGS. 30A-30E illustrate different views of an allograft spacer 1510 that can be used with the plate in FIGS. 26A-26D. The allograft spacer 1510 includes a notch 1517 for receiving extension members of the plate therein. FIGS. 31A-31E illustrate different views of a PEEK spacer 1610 that can be used with the same plate. The PEEK spacer 1610 includes a notch 1617 for receiving extension members of the plate therein. As noted above, the surgeon can desirably choose which spacer to insert into a surgical site.

FIGS. 32A and B illustrate different views of a spacer 1710 (either allograft or PEEK) for receiving extension members of the plate. The spacer 1710 includes a pair of channels or notches 1717 for receiving an extension member from a plate. Each of the notches 1717 extends a vertical distance from an upper surface of the spacer 1710 to a lower surface of the spacer 1710.

In FIG. 32B, a single notch 1717 out of a pair of notches is visible from the sideview. Each of the notches 1710 is comprised of two sidewalls 1721, 1723 that form a channel that extend from an upper surface to a lower surface of the spacer 1710. In some embodiments, one or more of the sidewalls 1721, 1723 can be straight with no angle or curvature. However, in other embodiments, as shown in FIG. 31, one or more sidewalls 1721, 1723 can have a curved portion. In the figure, first sidewall 1721 comprises a first curved portion 1722, while second sidewall 1723 comprises a second curved portion 1724. Due to the curved portions 1723, 1724, each of the notches 1710 can form a bent, curved or tortured channel for receiving an extension member of a plate therein. The advantage of having a tortured channel for receiving an extension member (such as any of the extension members 70 in FIG. 2D, 170 in FIG.

Figure 16C:
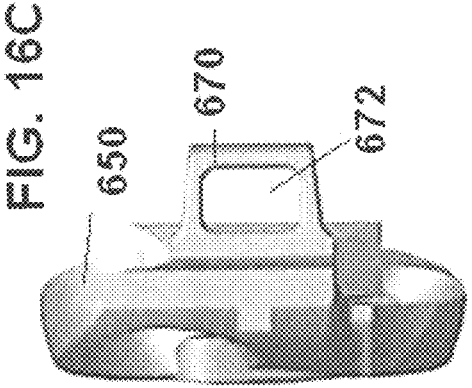
FIGS. 16A-16D illustrate different views of a low profile plate shown in FIGS. 15A-15D.
Figure 16D:
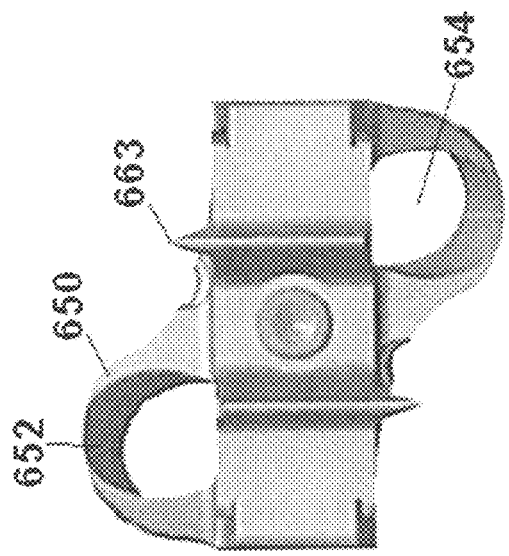
Figure 16A:
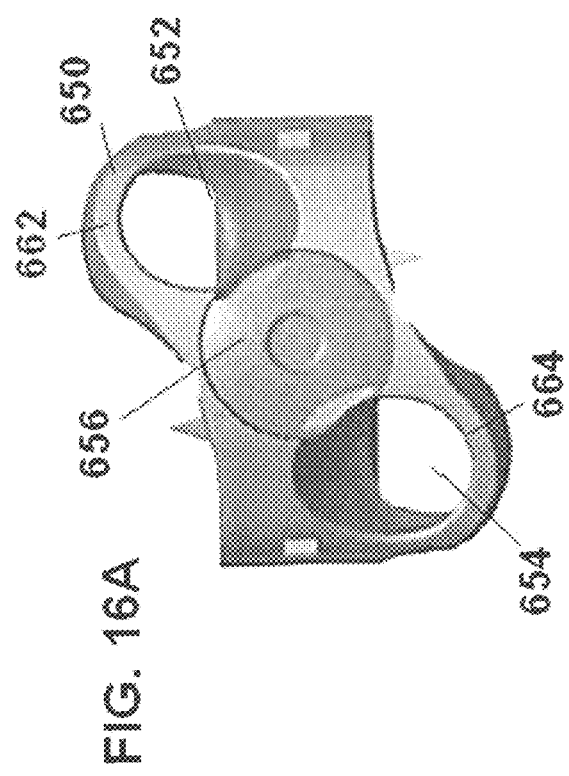
Figure 16B:
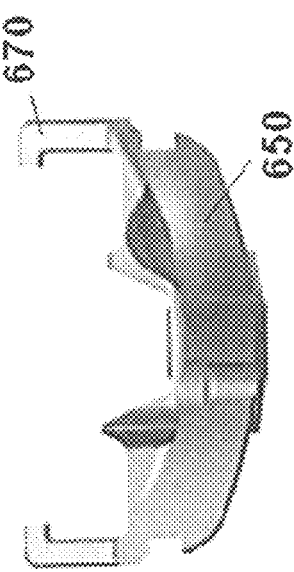

6D, 670 in FIG. 16B, 870 in FIG. 19, 970 in FIG. 20B, etc), is that this provides a tighter fit between the respective plate member and the spacer. Should a plate-spacer system encounter any forces that might cause slippage of the plate from the spacer, the tortured channel 1717 reduces the likelihood that this will occur.

As shown in FIG. 32B, the first sidewall 1721 and the second sidewall 1723 of the notch 1717 can include a straight upper portion, a curved or bent middle portion, and a straight lower portion. While the sidewalls 1721, 1723 are shown as substantially or completely parallel to each other in the figure, in other embodiments, the sidewalls 1721, 1723 need not be aligned with one another, so long as the sidewalls form a bent or tortured path through the spacer.

FIGS. 33-40 illustrate the different views of an intervertebral spacer 2010 according to the present disclosure. The intervertebral spacer 2010 as shown in FIGS. 33-40 may be, e.g., a stand-alone anterior lumbar interbody spacer used to provide structural stability in skeletally mature individuals following discectomies. These intervertebral spacers may be available in various heights and geometric configurations to fit the anatomically needs of a wide variety of patients. Specifically, FIGS. 33-40 illustrate one embodiment of an intervertebral spacer 2010. Intervertebral spacer 2010 may be generally positioned in the intervertebral space between two adjacent vertebral bodies. As shown in the figures, intervertebral spacer 2010 may include a spacer portion 2012 and a plate portion 2014. In one example, the spacer portion 2012 may include a graft window 2011 for the placement of, e.g., bone graft or bone-growth inducing material, to enhance fusion between two adjacent vertebral bodies.

The spacer portion 2012 can be comprised of any material that is conducive to the enhancement of fusion between the two adjacent vertebral bodies. In one particular embodiment, the spacer portion 2012 is made of PEEK material, which may be physiologically compatible. It should be noted that any other materials that are physiologically compatible also may be used. The spacer portion 2012 may include tantalum pins that enable radiographic visualization, or other suitable radiographic markers. The spacer portion 2012 further may include superior and inferior surfaces that are provided with a plurality of geometric configurations, such as, e.g., protrusions 2013 (e.g., ribs, bumps, other textures, or the like). The superior and inferior surfaces of the spacer portion 2012 may be bi-convex for greater contact with the vertebral endplates of the adjacent vertebral bodies. The protrusions 2013 can be configured to be any size or shape for further anchoring the spacer portion 2012 to each of the adjacent vertebral bodies. Protrusions 2013 on the superior and inferior surfaces of each implant may grip the endplates of the adjacent vertebral bodies to aid in expulsion resistance.

The plate portion 2014 can also be comprised of any physiologically compatible material. In one example, the plate portion 2014 of the intervertebral spacer 2010 may be formed from titanium. The plate portion 2014 may include at least one bore 2026. In some embodiments, plate portion 2014 may include a plurality of bores 2026, in such embodiments, one or more bores 2026 may or may not include threads for receiving corresponding threads on a fastener. That is to say, in some examples, one or more of bores 2026 may interact with features (e.g., threads) configured to receive features (e.g., corresponding threads) of a fastening member (e.g., a linear bone screw) to be disposed therethrough. Bores 2026 may be substantially linear. Such a configuration allows bores 2026 to receive both linear fastening members and curvilinear fastening members. That is, a given bore 2026 may be configured to receive either a linear fastening member (e.g., a screw) or a curvilinear fastening member (as discussed below in greater detail) at the discretion of an operator, surgeon, physician, or the like. In one embodiment, e.g., bores 2026 may include one or more features, e.g., threads, that are configured to engage with threads of a fastening member (e.g., a linear fastening member or bone screw). Further, in some examples, a curvilinear fastening member disposed through a given bore 2026 may be configured so as not to engage the threads of the given bore 2026. Still further, each bore 2026 may include locking features configured to engage with complimentary features on a curvilinear fastening member to prevent the curvilinear fastening member from rotating when disposed through the bore 2026. In one example, each bore 2026 may be defined by a circumferential wall having a recess (not shown) disposed therein. The recess may be configured to receive a protrusion extending from the curvilinear fastening member to prevent the curvilinear fastening member from rotating. In one example, three bores 2026 may be provided. In yet another example, two outer bores 2026 may surround a central bore 2026. The two outer bores 2026 may be angled to guide a fastening member (e.g., a vertebral anchor 2300 described with reference to FIGS. 61-68, or a bone screw) along a first trajectory 2040 shown in FIG. 46 (e.g., toward one of a superior or inferior surface of intervertebral spacer 2010), while the central bore 2026 may be angled to guide a fastening member along a second trajectory 2042 (e.g., toward the other of the superior and inferior surface of intervertebral spacer 2010), and vice versa. In some examples, all bores 2026 may guide respective fasteners along the same trajectory. The bores 2026 can accommodate a straight longitudinal fastening member (e.g., a screw, pin, or the like) and/or a fastening member exhibiting a curvature (e.g., vertebral anchor 2300 shown in FIG. 61). In some examples, a combination of vertebral anchors 2300 and conventional screws may be used to install the same intervertebral spacer 2010.

Also, in the plate portion 2014 of the intervertebral spacer 2010, a fastener back out prevention mechanism may be provided. The fastener back out prevention mechanism may include one or more screws 2016, each having a head portion 2024 and a shank 2022 having threads 2022a. Shank 2022 may be received by a bore 2048 (shown in FIG. 40) that extends from a first side 2044 of plate portion 2014 toward a second side 2046 of plate portion 2014. Shank 2022 also may be received by a nut 2018 having a threaded bore 2018a (shown in FIG. 33). Nut 2018 may have a substantially rectangular cross-section, or may have another suitable shape. Nut 2018 may be secured within a recess 2020 on second side 2046 of plate portion 2014. However, it is contemplated that screws 2016 may be secured to plate portion 2014 by any other suitable mechanism. Head portion 2024 may have a generally rectangular cross-section such that it may prevent a fastening member from backing out of bores 2026 when disposed in certain configurations (e.g., a blocking configuration). For example, referring to FIG. 40, the head portion 2024 of screw 2016 may extend over, cover, and/or block at least a portion of the opening of one more of bores 2026, preventing a fastening member (e.g., a vertebral anchor 2300 or a bone screw) extended through a bore 2026 from backing out of plate portion 2014 and a vertebral body. It is also contemplated that in some examples, a single head portion 24 may extend at least partially over two adjacent bores 2026 (e.g., both an outer bore 2026 and a central bore 2026), thereby blocking the openings of more than one bore 2026 at the same time while disposed in a blocking configuration. Head portion 2024 can be moved from the blocking configuration to a non-blocking configuration by rotating head portion by, e.g., 90 degrees or another suitable measure. While depicted as rectangular, it is contemplated that head portion 2024 may be formed in other suitable elongate shapes, such as, e.g., cylindrical or the like. In the example of FIG. 8, plate portion 2014 may be configured to receive two screws 2016 in bores 2048 (shown in FIG. 40). Each of the screws 2016 may be configured to block fastening members disposed in an outer bore 2026 and a central bore 2026, such that each outer bore 2026 is blocked by a single screw 2016, and the central bore 2026 is blocked by both screws 2016.

A coupling mechanism may connect the spacer portion 2012 and the plate portion 2014 rigidly to each other, if desired. With reference to FIG. 34, the coupling mechanism may include one or more fastening members 2034 that extend through corresponding recesses 2036 disposed through spacer portion 2012 and recesses 2038 disposed through at least a portion of plate portion 2014. In one example, a fastening member 2034 may extend through the superior and inferior surfaces of spacer portion 2012 (via a recess 2036) and may be received by recess 38 of plate portion 2014, thereby coupling spacer portion 2012 and plate portion 2014. It is contemplated that recess 2038 and fastening member 2034 may include complimentary mating features (e.g., threads) to facilitate coupling of plate portion 2014 to spacer portion 2012. In the example shown in FIG. 34, plate portion 2014 may be formed by three bore sections 2028, 2030, and 2032. Bore sections 2028, 2030, and 2032 may either be integrally formed or detachable with spacer portion 2012. In one example, bore section 2028 may be integral with spacer portion 2012 while bore sections 2030 and 2032 may be detachable with spacer portion 2012 via fastening members 2034 and recesses 2036 and 2038. In one example, the detachable bore sections 2030 and 2032 may include the outer bores 2026 that are configured to direct a vertebral anchor 2300 or bone screw along the first exit trajectory 2040, and the bore section 2028 may include the central bore 2026 configured to direct a vertebral anchor 2300 or bone screw along the second exit trajectory 2042. Further, one or more of the bore sections 2028, 2030, and 2032 may include a portion configured to extend through a slot of or other opening in spacer portion 2012. In such examples, the recesses 2036, 2038, or the like associated with the bore sections may align with recesses formed through spacer portion 2012 to receive fastening members 2034.

Plate portion 2014 also may include coupling features for coupling plate portion 2014 to an anchor insertion device 2100 which will be described further with reference to FIGS. 42-55. As shown in FIG. 40, plate portion 2014 may include a channel (e.g., a snap-fit channel) 2050 having an opening disposed in an outer surface of plate portion 2014. The channel 2050 may be configured to receive an extension (e.g., a cantilever and/or snap-fitting extension) of anchor insertion device 2100 to couple plate portion 2014 to the insertion device 2100. In some examples, channel 2050 may be disposed in bore section 2030 of plate portion 2014. With continuing reference to FIG. 40, channel 2050 may have a generally ovular opening, although other suitable opening configurations such as, e.g., circular, square, rectangular, star-shaped, or the like are also contemplated. Plate portion 2014 also may include a bore 2052 (e.g., a threaded bore) having an opening that is also disposed through an outer surface of plate portion 2014. In one example, bore 2052 may be disposed through bore section 2032 of plate portion 2014.

In an exemplary method, a physician, surgeon, or other suitable operator may remove, among other things, the native intervertebral disc between two vertebral bodies. The operator then may select a given intervertebral spacer, e.g., intervertebral spacer 2010, to replace the removed native intervertebral disc. Based on the geometry of the surrounding vertebral bodies and/or anatomy, the operator may determine that linear fastening members (e.g., linear bone screws), curvilinear fastening members (e.g., vertebral anchors 2300 or 2400), or a combination of linear fastening members and curvilinear fastening members, will provide optimal fit and securement of intervertebral spacer 2010 between the vertebral bodies. For example, the curvature of the spine at one or more of the vertebral bodies may substantially inhibit the use of the tools and driving members used to install linear fastening members. In such examples, curvilinear fastening members may be selected to secure intervertebral spacer 2010. The curvilinear fastening members may be installed through the same linear bore 2026 that may be configured to receive linear fastening members. Further, the curvilinear fastening members may be installed through the linear bore with a positioning member (described with reference to FIG. 42) utilizing a guide member that can be extended only along a linear track.

In one example, one or more curvilinear fasteners may be used to secure intervertebral spacer 2010 to one vertebral body defining an intervertebral space, while one or more linear fasteners may be used to secure intervertebral spacer 2010 to the other vertebral body defining the intervertebral space. For example, curvilinear fasteners may be extended through outer bores 2026 while a linear fastener is extended through central bore 2026. Alternatively, linear fastening members may be extended through outer bores 2026 while a curvilinear fastening member is extended through central bore 2026. In yet another example, both linear and curvilinear fastening members may be used to secure the same intervertebral spacer into a given vertebral body. That is, a curvilinear fastening member may be extended through one outer bore 2026, while a linear fastening member is extended through the other outer bore 2026.

Figure 41:
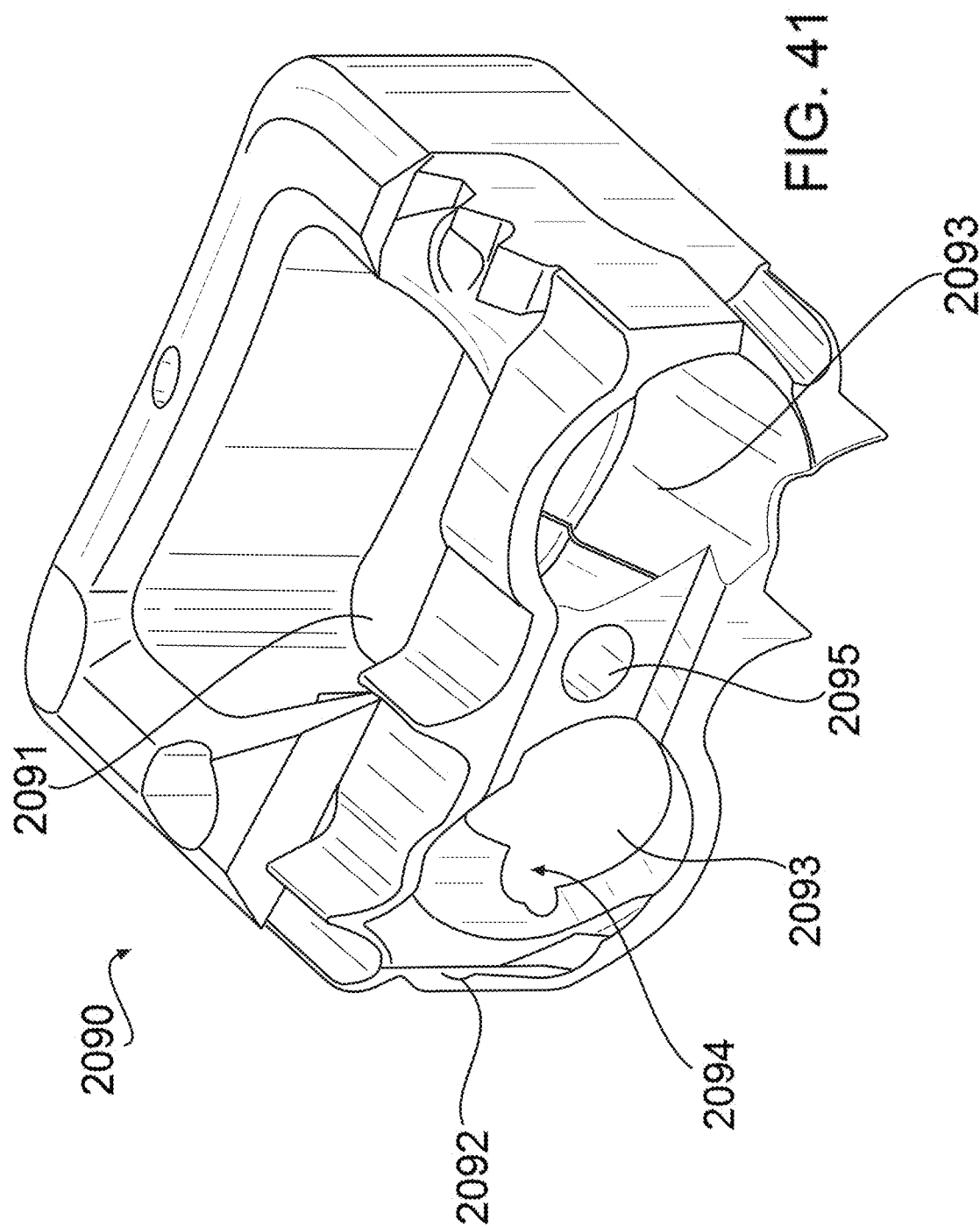
FIG. 41 is a perspective view of another exemplary intervertebral spacer in accordance with an example of the present disclosure.

FIG. 41 depicts an intervertebral spacer 2090 in accordance with an example of the present disclosure. In some examples, intervertebral spacer 2090 may be substantially similar to intervertebral spacer 2010, or may be another suitable intervertebral spacer. In the example shown in FIG. 41, spacer 2090 may be a generally rectangular spacer defining a cavity 2091. Cavity 2091 may be packed with bone graft or bone-growth inducing materials. Spacer 2090 may include one or more of inferior surfaces, superior surfaces, biconvex surfaces, among others. In some examples, the surfaces of spacer 2090 or any other bone contacting surface described in the present disclosure may include one or more of teeth, ridges, friction increasing elements, keels, or gripping or purchasing projections.

Figure 57:
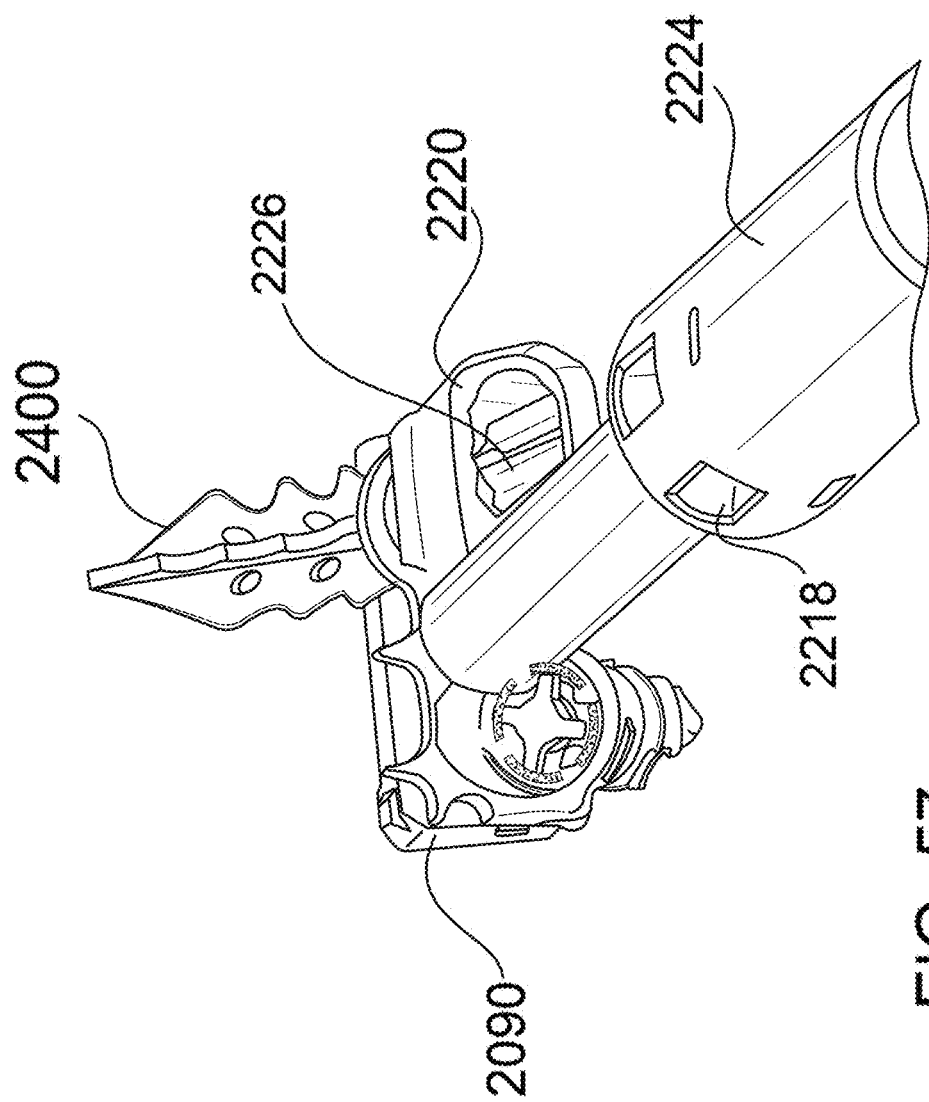
FIG. 57 is a perspective view of an insertion device and an intervertebral spacer having a plurality of fasteners in accordance with an example of the present disclosure.

Spacer 2090 may include a plate portion 2092 that may include one or more features described with reference to plate portion 2014 of intervertebral spacer 2010. In one example, one or more bores 2093 may disposed through plate portion 2092. Though FIG. 41 depicts two bores 2093, those of ordinary skill in the art will recognize that any suitable number of bores may be provided. Bores 2093 may include one or more features described with reference to bores 2026 of intervertebral spacer 2010. The two bores 2093 may be angled to guide a fastening member (e.g., a vertebral anchor 2300 or a bone screw) along differing trajectories. For example, one bore 2093 may be angled to urge a fastening member along a first trajectory (e.g., toward one of a superior or inferior surface of intervertebral spacer 2090), while the other bore 2093 may be angled to urge a fastening member along a second trajectory (e.g., toward the other of the superior and inferior surface of intervertebral spacer 2090). The bores 2093 can accommodate a straight longitudinal fastening member (e.g., a screw, pin, or the like) and/or a fastening member exhibiting a curvature (e.g., vertebral anchor 2300 or 2400). In some examples, a combination of vertebral anchors 2300 or 2400 and conventional screws may be used to install the same intervertebral spacer 2090 as shown in FIG. 57. A circumferential wall defining bores 2093 may further include one or more recesses 2094 disposed therein. The one or more recesses 2094 may be configured to receive one or more protrusions 2460 disposed on a head portion 2406 of a vertebral anchor 2400 (described with reference to FIGS. 69-72). Thus, in some examples, recesses 2094 may be partially-spherical to receive protrusions 2460. However, it is contemplated that recesses 2094 may be formed in any suitable shape configured to receive protrusions 2460. Plate portion 2092 also may include a bore 2095 having an opening that is disposed through an outer surface of plate portion 2092. The bore 2095 may include one or more features, e.g., threads or other features to engage with an insertion device 2200 described with further detail below. Intervertebral spacer 2090 also may include one or more features configured to prevent fastening members from backing out of bores 2093, such as, e.g., screws 2016 described with reference to FIGS. 33-40.

Intervertebral spacer 2090 may be inserted into an intervertebral space between two vertebral bodies in a substantially similar manner as intervertebral spacers 2010. In one example, one or more curvilinear fasteners may be used to secure intervertebral spacer 2090 to one vertebral body defining an intervertebral space, while one or more linear fasteners may be used to secure intervertebral spacer 2090 to the other vertebral body defining the intervertebral space. For example, a curvilinear fastener may be extended through one bore 2093 while a linear fastener is extended through the other bore 2093.

Figure 42:
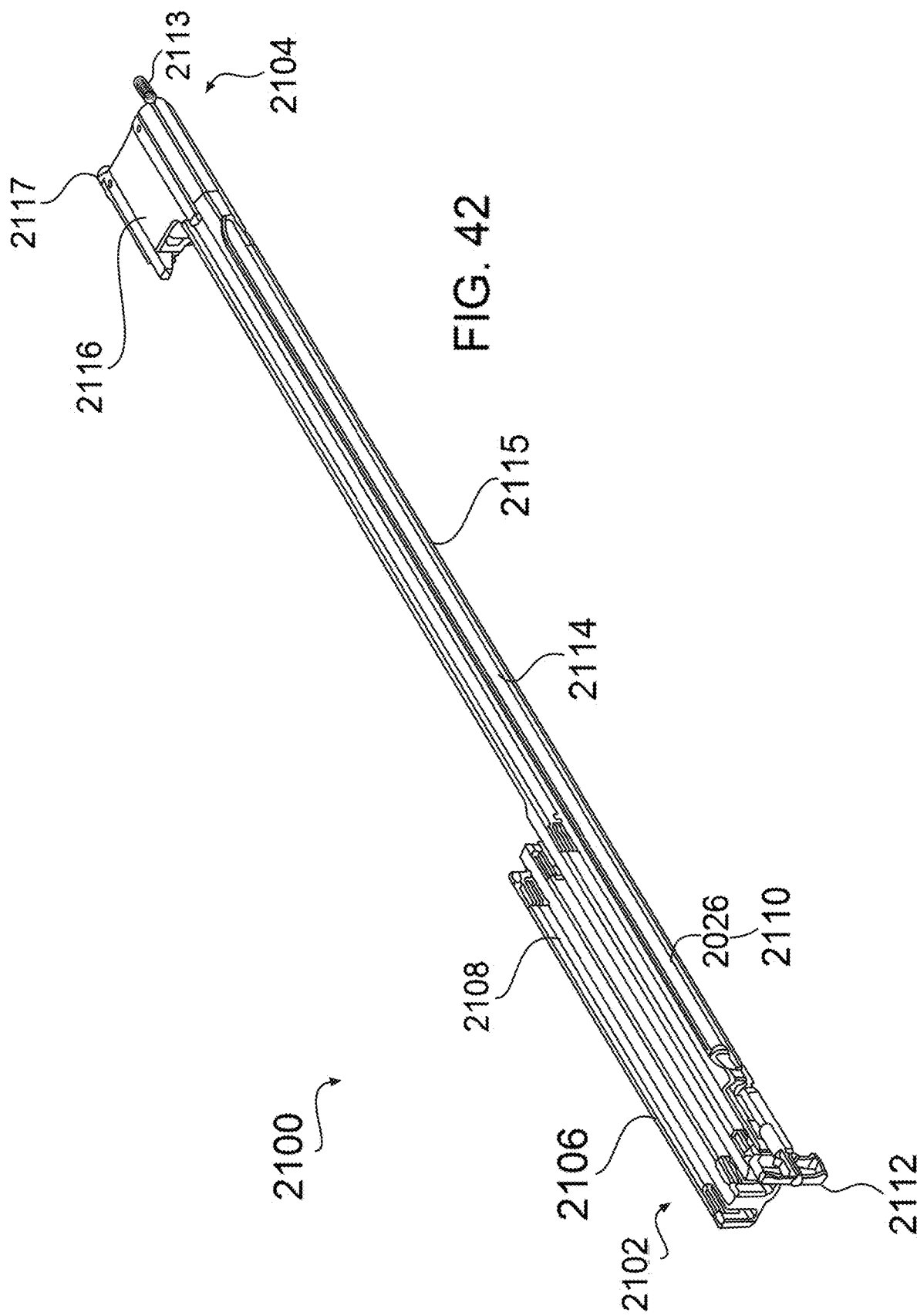
FIG. 42 is an insertion device in accordance with an example of the present disclosure.
Figure 56:
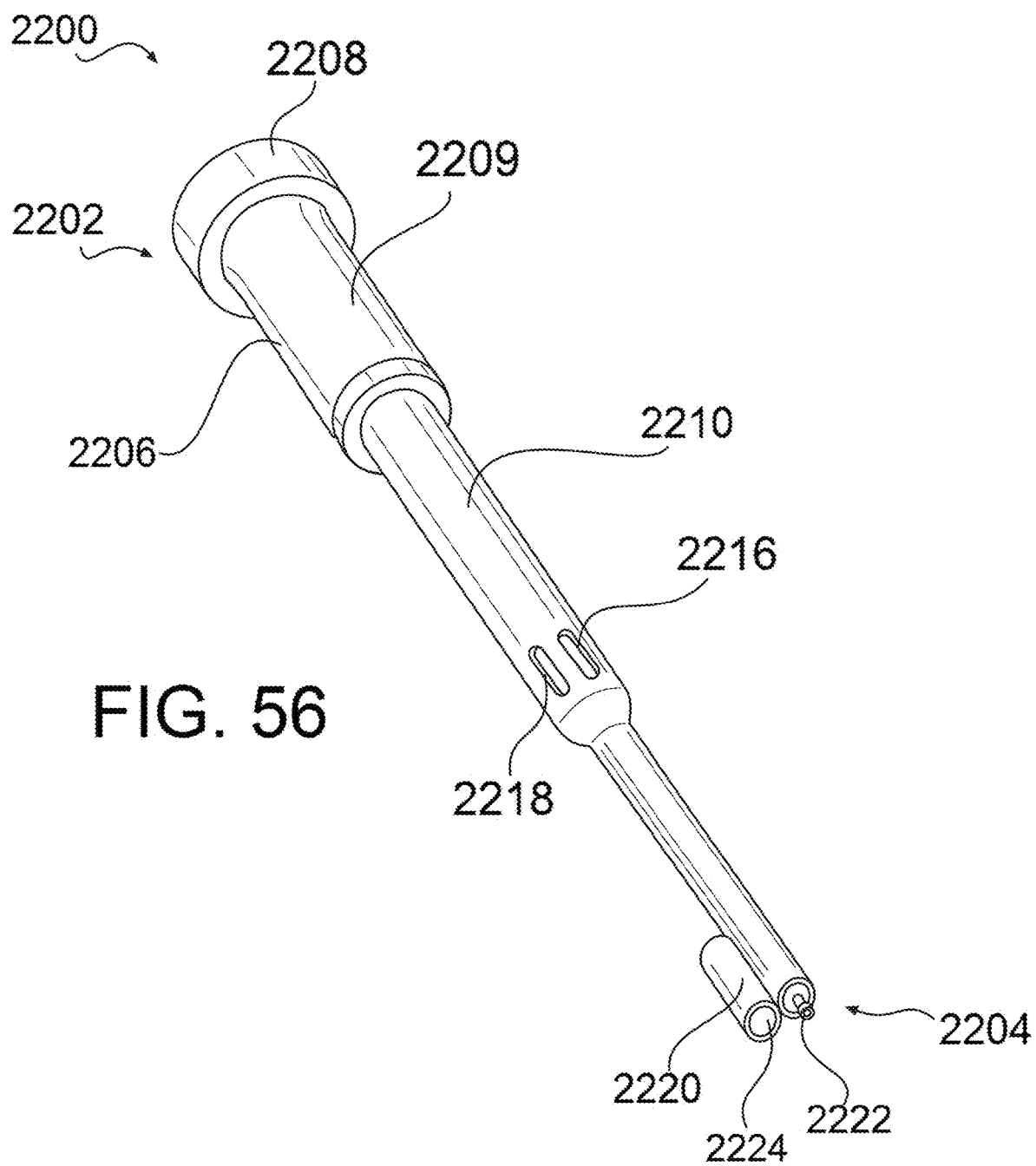
FIG. 56 is a perspective view of another exemplary insertion device in accordance with an example of the present disclosure.

An insertion device 2100 is shown in FIG. 42, which may be used to position vertebral anchors 2300 through a plate portion of an intervertebral spacer (e.g., plate portion 2014 of intervertebral spacer 2010) and through a vertebral body. Insertion device 2100 may extend from a trailing end 2102 toward a leading end 2104. A trailing housing 2106 may be disposed at trailing end 2102 and may define one or more elongate channels 2108. In the embodiment shown, three elongate channels 2108 are shown, although any other suitable number of elongate channels 2108 may be disposed through trailing housing 2106. Each of elongate channels 2108 may receive a guide member 2110 therethrough. Guide member 2110 may include a head portion 2112 and an elongate portion 2114 that extends away from the head portion 2112. In some examples, head portion 2112 may include one or more flattened and reinforced surfaces configured to receive the force of a striking member (e.g., a hammer or the like). Elongate portion 2114 may be extended through one or more elongate channels 2108 toward leading end 2104. The distal or leading end of elongate portion 2114 may include a stepped portion 2132 (shown in FIG. 50). Stepped portion 2132 may be separated from the remainder of elongate portion 2114 by a vertical wall 2130. In some examples, stepped portion 2132 may include a smaller cross-sectional dimension (e.g., thickness or width) as compared to a remainder of elongate portion 2114.

A connecting housing 2115 may extend from trailing housing 2106 toward an anchor housing 2116 disposed at leading end 104. In some examples, connecting housing 2115 may be an alignment shaft configured to align elongate channels 2108 with a corresponding number of anchor channels 2118 (see FIG. 43) disposed in anchor housing 2116. In the embodiment shown in FIG. 42, connecting housing 2115 may extend from only one of elongate channels 2108 to couple trailing housing 2106 to anchor housing 2116. However, those of ordinary skill in the art will appreciate that a shaft 2116 may extend from more than one elongate channel 2108 toward anchor housing 2116. Guide member 2110 may extend through an elongate channel 2108, through connecting housing 2115, and into an anchor channel 2118, where it may come into contact with a vertebral anchor 2300 just before inserting the vertebral anchor 2300 through a vertebral body, as described further with reference to FIGS. 50-55. In some examples, connecting housing 2115 may merely align certain elongate channels 2108 in trailing housing 2106 with anchor channels 2118 disposed in anchor housing 2116. In such examples, elongate portion 2114 of guide member 2110 may exit a leading end of elongate channel 2108 and extend through an open and unconfined space before entering a trailing end of an anchor channel 2118.

As best seen in FIG. 43, anchor housing 2116 may include one or more anchor channels 2118. Each anchor channel 2118 may have a variable cross-section along the length of anchor housing 2116. In some examples, a given cross-section of anchor channel 2118 may be t-shaped or any another suitable cross-section. A curvature at the leading end of anchor channel 2118 may be complimentary to certain portions of a curvilinear anchor (e.g., anchor 2300 shown in FIG. 61). Those portions may include an elongate shank 2308 and elongate fin 2310, shown in FIGS. 61 and 63. That is, anchor channel 2118 may be defined by a concave surface 2119 that is complimentary to elongate shank 2308 of vertebral anchor 2300. For example, a laterally extending portion 2148 of each channel 2118 may be configured to complement and receive a curved elongate shank 2308, and a vertically extending portion 2126 of each channel 2118 may receive a curved elongate fin 2310. Thus, a vertebral anchor 2300 may be disposed within each anchor channel 2118 and may exit anchor channel 2118 along a given exit trajectory. Some anchor channels 2118 may urge a vertebral anchor 2300 along a first exit trajectory 2120 while other exit channels 2118 may urge a vertebral anchor 2300 along a second exit trajectory 2122. First exit trajectory 2120 may extend in a first vertical direction out of the leading end of anchor housing 2116 while the second, different exit trajectory 2122 may extend in a second vertical direction out of the trailing end of anchor housing 2116. A given anchor housing 2116 may include a plurality of anchor channels 2118 that may direct all vertebral anchors 2300 along the first exit trajectory 2120, all vertebral anchors 2300 along the second exit trajectory 2122, or some vertebral anchors 2300 along the first exit trajectory 2120 and some vertebral anchors 2300 along the second exit trajectory 2122. Each of first and second trajectories 2120 and 2122 may intersect a longitudinal axis of insertion device 2100 and/or guide member 2110. In one example, laterally adjacent anchor channels 2118 may be configured to direct vertebral anchors 2300 along different exit trajectories. In the exemplary embodiment shown in FIGS. 43-46, anchor housing 2116 may include three anchor channels 2118. Two outer anchor channels 2118 may be laterally offset from an inner anchor channel 2118. The outer anchor channels 2118 may urge respective vertebral anchors 2300 along first exit trajectory 2120 while the inner anchor channel 2118 may urge a vertebral anchor 2300 along second exit trajectory 2122. Anchor channel 2118 may further include a stop wall 2146 (shown in FIGS. 50-55) that may extend radially inward from a wall of anchor channel 2118. Stop wall 2146 may be configured to abut a vertical wall of elongate portion 2114 (of guide member 2110) to prevent elongate portion 2114 from being inserted too far distally into a patient by an operator. Thus, stop wall 2146 also may prevent an inadvertent excessive force from being applied to intervertebral spacer 2010 or to a vertebral body by elongate portion 2114.

Anchor housing 2116 may include one or more features to engage with corresponding features disposed on plate portion 2014 of intervertebral spacer 2010. In one example, an extension 2117 (e.g., a hook fit, slip fit or cantilevered snap-fit extension 2117) may extend longitudinally outward from the leading end (e.g., a distal face) of anchor housing 2116. Extension 2117 may include one or more surfaces configured to engage channel 2050 of plate portion 2014 in a snap fit or other suitable engagement. Anchor housing 2116 also may include a threaded shank 2113 that extends longitudinally outward from the leading endface of anchor housing 2116. In some examples, threaded shank 2113 may be received by bore 2052 of plate portion 2014. While snap-fit and threaded connections are disclosed in the examples shown by the figures, it should be noted that any other additional or alternative type of engagement may be utilized to couple anchor housing 2116 to plate portion 2014.

Anchor housing 2116 also may include one or more positioning members 2138, as shown in FIG. 50. Each positioning member 2138 may secure a vertebral anchor 2300 within a respective anchor channel 2118. Thus, each anchor channel 2138 may be associated with its own respective positioning member 2138. In one example, positioning member 2138 may be an elongate cantilever that is coupled to a leading end portion of anchor housing 2116 via a linkage or hinge 2140. In some examples, linkage or hinge 2140 may be a spring-biased linkage or may be another suitable hinge or linkage. Positioning member 2138 may extend from linkage 2140 toward trailing end 2102. At its proximal or trailing end, positioning member 2138 may include a ramp 2142 and an extension 2144 spaced from ramp 2142 by a recess. Ramp 2142 may be an inclined surface configured to engage elongate portion 2114 of guide member 2110. Positioning member 2138 may be configured to pivot about the linkage 2140 and away from an interior of anchor channel 2118 when ramp 2142 is engaged by elongate portion 2114 of guide member 2110. In some examples, positioning member 2138 may pivot in a direction that is opposite to the exit trajectory of its associated anchor channel 2118. That is, if a given anchor channel 2118 is configured to guide a vertebral anchor into a vertebral body along first trajectory 2120, the associated positioning member 2138 of that elongate channel may pivot about linkage 2140 in the vertical direction that is opposite to the vertical vector of first trajectory 2120. On the other hand, if a given anchor channel 2118 is configured to guide a vertebral anchor 2300 along the second trajectory 2122, the associated positioning member 2138 of that anchor channel 2118 may be configured to pivot in a vertical direction that is opposite to the vertical vector of second trajectory 2122. Extension 2144 may include any suitable configuration (e.g., a ball or the like), and may be configured to be releasably coupled to a vertebral anchor 2300 via groove 22318.

Vertebral anchors 2300 may be loaded into anchor channels 2118 prior to the coupling of anchor housing 2116 to plate portion 14 of intervertebral spacer 2010. Vertebral anchors 2300 may be loaded from either the trailing end or the leading end of anchor housing 2116, if desired. In some examples, vertebral anchors 2300 may be loaded by a spring-loaded block device. In one example, a vertebral anchor 2300 may be loaded into the leading end of anchor housing 2116 with trailing end 2302 of the vertebral anchor being inserted first. That is, trailing end 2302 of vertebral anchor 2300 may be loaded into anchor channels 2118 before leading end 2304. Thus, vertebral anchors 2300 may be loaded in a reverse manner such that the vertebral anchors 2300 are loaded in the opposite direction to which they are inserted into the body. As vertebral anchors 2300 are moved proximally through anchor channels 2116, groove 2318 may be coupled to extension 2144 of positioning member 2138. The docking, mating, or connection of extension 2144 with groove 2318 may fix vertebral anchor 2300 within anchor channel 2118 until vertebral anchor 2300 is inserted through a vertebral body. In one example, extension 2144 may be a ball and a groove 2318 of vertebral anchor 2300 may be a socket such that extension 2144 and groove 2318 form a ball and socket joint. However, those of ordinary skill in the art will appreciate that any other suitable form of releasable connection may be utilized.

Anchor housing 2116 may be coupled to intervertebral spacer 2010 to install vertebral anchors 2300 into the body. Anchor housing 2116 and plate portion 2014 may be aligned via extension 2117 and channel 2050, and/or via shank 2113 and bore 2052 in such a manner as to align channels 2118 of anchor housing 2116 with bores 2026 of plate portion 2014. The alignment of channels 2118 and bores 2026 may permit one or more vertebral anchors 2300 to be guided from a channel 2118 through a corresponding bore 2026 of plate portion 2014, and into a vertebral body. Further, the anchor housing 2116 and plate portion 2014 may be aligned such that the exit trajectory of a given channel 2118 may be aligned (e.g., collinear or coplanar) with the exit trajectory of an aligned bore 2026. In some examples, the number of channels 2118 disposed in anchor housing 2116 may correspond exactly with the number of bores 2026. However, it is contemplated that an exact correspondence may not exist between channels 2118 and bores 2026. For example, an anchor housing 2116 may include fewer channels 2118 than bores 2026 in a plate portion. In such examples, anchor housing 2116 may be coupled to plate portion 2014 in a number of different configurations. In such examples, after a vertebral anchor 2300 is inserted through a vertebral body, anchor housing 2116 may be uncoupled from plate portion 2014, reloaded with a new vertebral anchor 2300, and recoupled to plate portion 2014 at a different location.

With continuing reference to FIGS. 50-55, there is depicted an exemplary method of positioning a vertebral anchor 2300 via insertion device 2100. Referring to FIG. 50, vertebral anchor 2300 is shown loaded into an anchor channel 2118. The vertebral anchor 2300 may be secured within the anchor channel 2118 via the coupling of extension 2144 with groove 2318 of the vertebral anchor 2300 as set forth above. Elongate portion 2114 of guide member 2110 then may be advanced distally (e.g., in the direction of leading end 2304) such that the distal end of elongate portion 2114 may contact ramp 2142 (FIGS. 51 and 52). In some examples, stepped portion 2132 of elongate portion 2114 may contact the ramp 2142. Elongate portion 2114 may be advanced further distally, causing ramp 2142 to slide vertically upward, thereby disengaging extension 2144 from groove 2318 of vertebral anchor 2300 (FIG. 52). As elongate portion 2114 is advanced further distally, the distal end of elongate portion 2114 may abut the trailing end 2302 of vertebral anchor (FIG. 53). In some examples, the stepped portion 2132 of elongate portion 2114 may abut head portion 2306 of vertebral anchor 2300. Uncoupled from extension 2144, vertebral anchor 2300 then may be advanced out of the leading end of anchor housing 2116 and anchor channel 2118 (FIG. 54) and ultimately inserted into a vertebral body (not shown) along a given exit trajectory (e.g., trajectory 2120 or 2122), as shown in FIG. 55. After impacting one vertebral anchor 2300 through a vertebral body, the same guide member 2110 (and elongate portion 2114) may be withdrawn and reinserted through a different elongate channel 2108 and anchor channel 2118 (having another preloaded vertebral anchor 2300), to impact a different vertebral anchor 2300, if desired. Alternatively, each set of elongate channels may include a dedicated guide member 2110.

One embodiment of an insertion device 2200 is shown in FIGS. 56-60. Insertion device 2200 may extend from a first, trailing end 2202 toward a second, leading end 2204. A base portion 2206 may include a proximal annular rim 2208 and base shaft 2209 extending therefrom. An alignment shaft 2210 may extend from base shaft 2209. In the example shown in FIG. 56 the leading end 2204 of alignment shaft 2210 may have a smaller diameter than the trailing end of alignment shaft 2210, although other suitable configurations, including a substantially constant diameter shaft 2210, are also contemplated. In some examples, alignment shaft 2210 may include one or more longitudinally extending windows 2218. In some examples, alignment shaft 2210 may be a hollow elongate shaft accommodating a drive mechanism 2216 therein. Drive mechanism 2216 may be configured to actuate a coupling 2222 disposed at the leading end of alignment shaft 2210. Drive mechanism 2216 may be a spring loaded drive shaft configured to reciprocally move coupling 2222 between a retracted configuration and an extended configuration. While in the extended configuration, coupling 2222 may engage with, e.g., bore 2095 of intervertebral spacer 2090 to couple insertion device 2200 to intervertebral spacer 2090. While coupling 2222 is engaged to bore 2095, drive mechanism 2216 may move coupling 2222 to the retracted configuration to disengage insertion device 2200 from intervertebral spacer 2090.

Coupling 2222 may be disposed in an anchor housing 2220 that is disposed at the leading end 2204 of alignment shaft 2210. Anchor housing 2220 may include at least one anchor channel 2224. Anchor channel 2224 may include one or more features described with reference to anchor channel 2118 of insertion device 2100. For example, anchor channel 2224 may have a variable cross-section along its length and may have a concave surface 2230 (shown in FIGS. 58-60) that is complimentary to, e.g., elongate shank 2408 of anchor 2400 shown in FIG. 69. For example, a laterally extending portion of anchor channel 2224 may receive a curved elongate shank 2408. A guide member 2228 that may be substantially similar to guide member 2110 may be inserted through anchor channel 2224 to assist with deploying an anchor disposed therein.

It is contemplated that insertion device 2200 may include additional or alternative features for attaching to intervertebral spacer 2090 such as, e.g., positive attachments, cam attachments, threaded attachments or other suitable attachments. In some examples, pins or other members also may prevent the rotation of insertion device 2200 relative to intervertebral spacer 2090 when the insertion device 2200 and intervertebral spacer 2090 are engaged. In some examples, the leading end of insertion device 2200 may couple to the anterior face, lateral sides, or other regions of intervertebral spacer 2090. In one embodiment, the insertion device 2200 may include a stop that extends in either the cephalad or caudal direction of a centerline of insertion device 2200 to prevent the intervertebral spacer 2090 from being inadvertently impacted undesirably. That is, a stop may extend from the superior or inferior surface of insertion device 2200 and may contact, e.g., a surface of the intervertebral spacer or vertebral body.

Anchor housing 2220 may be coupled to an intervertebral spacer, e.g., intervertebral spacer 2090, to install vertebral anchors 2400 into the body. Anchor housing 2220 and plate portion 2092 may be aligned via coupling 2222 and bore 2095, in such a manner as to align channel 2224 of anchor housing 2220 with a bore 2093 of plate portion 2014. In some examples, anchor channels 2224 may be laterally offset from the length of alignment shaft 2210. The alignment of channel 2224 and bore 2093 may permit one or more vertebral anchors 2400 to be guided from a channel 2224 through a corresponding bore 2093 of plate portion 2092, and into a vertebral body. Further, the anchor housing 2220 and plate portion 2092 may be aligned such that the exit trajectory of a given channel 2224 may be inline (e.g., collinear or coplanar) with the exit trajectory of an aligned bore 2093. While only one anchor channel 2224 is shown in the example of FIGS. 56-60, it is contemplated that additional anchor channels 2224 may be utilized (e.g., a double or multi-barreled configuration) such that the number of channels 2224 disposed in anchor housing 2220 may correspond exactly with the number of bores 2093 in vertebral spacer 2090. In some examples, a guide member may extend through one or more anchor channels 2224 to simultaneously insert one or more fastening members (e.g., vertebral anchors or screws) through one or more vertebral bodies. Other mechanisms of anchor insertion are also contemplated such as, e.g., a blocking set screw or leaf spring cutout of the spacer or plate that is flexible in the insertion direction and stiff in the expulsion direction. An associated intervertebral spacer also may include rotational stabilizers to add stability to the construct in vivo, and may contain radiographic markers to aid in interoperative visibility.

Figure 58:
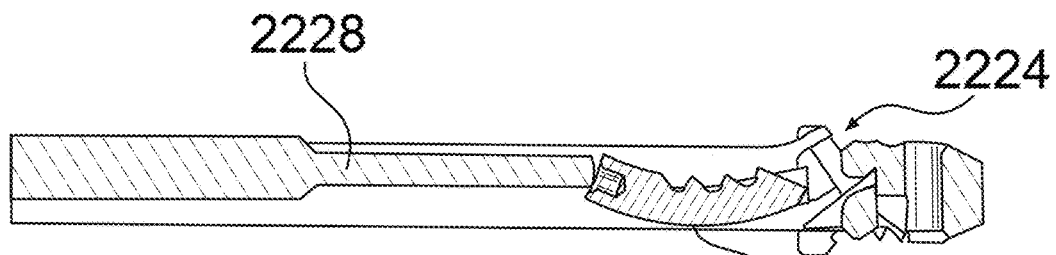
FIGS. 58-60 depict another exemplary method of installing a vertebral anchor in accordance with an example of the present disclosure.
Figure 59:
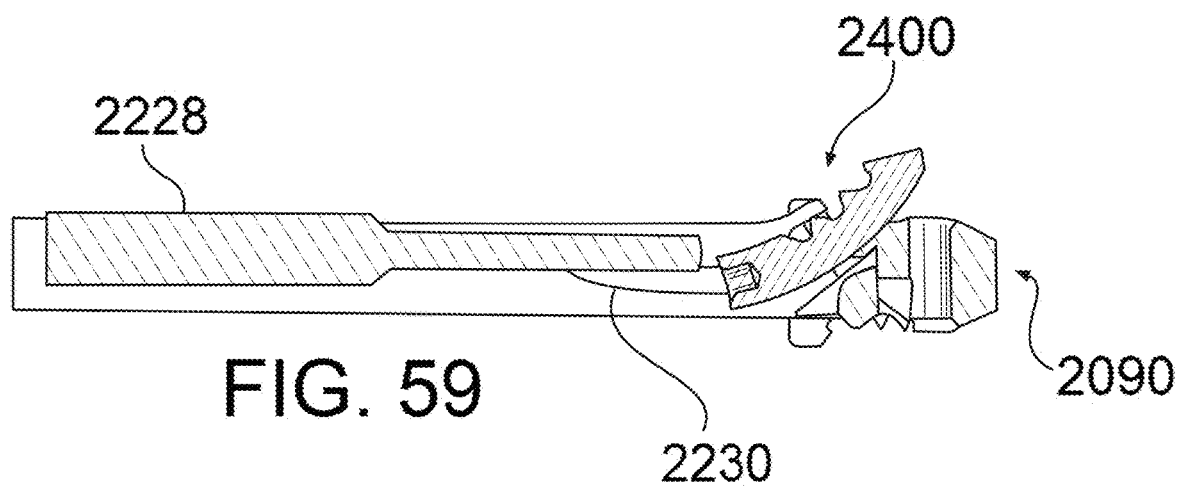
Figure 60:
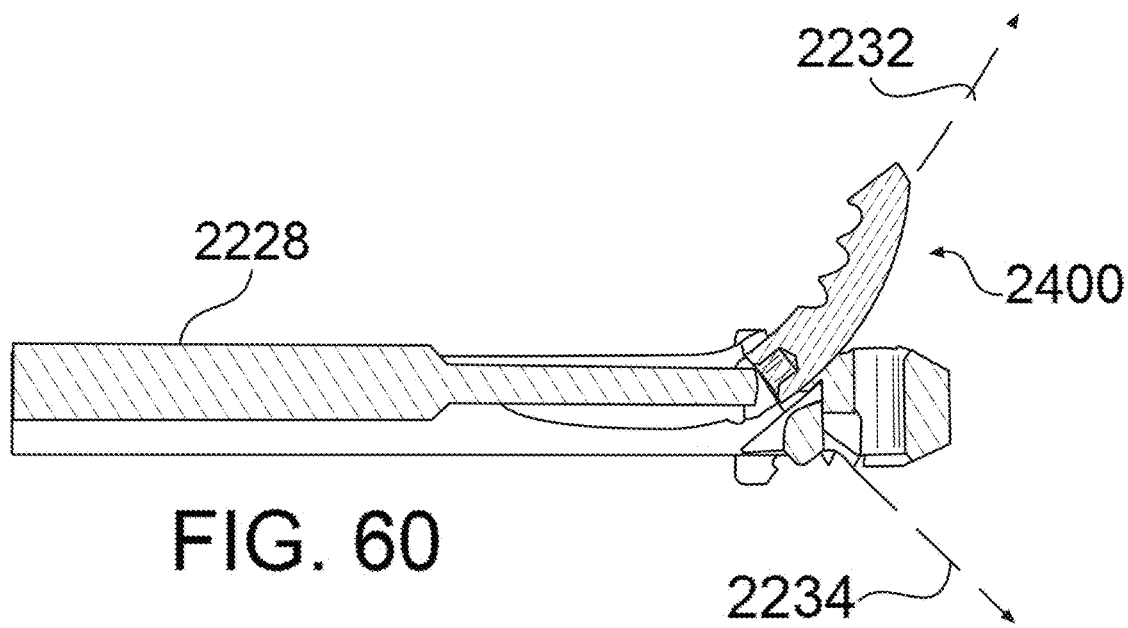
Figure 65:
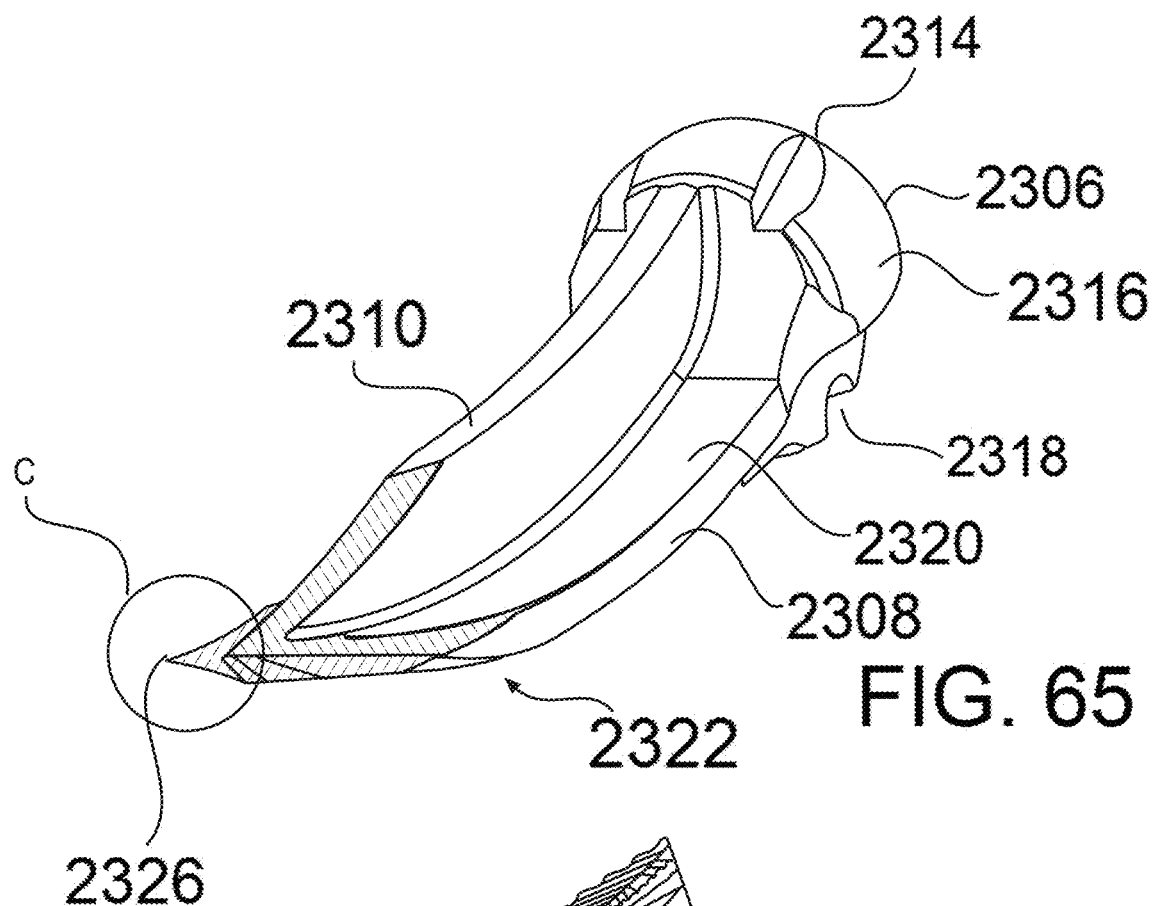
FIG. 65 is a perspective view of the vertebral anchor of FIG. 61.
Figure 66:
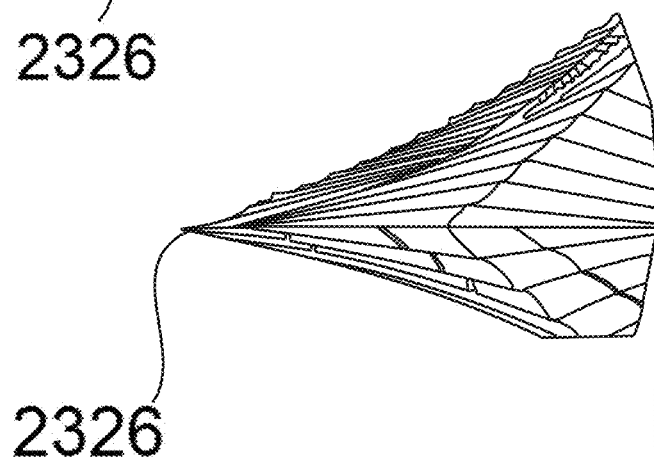
FIG. 66 is an enlarged view of detail C in FIG. 65, illustrating a distal portion of the vertebral anchor of FIG. 65.
Figure 69:
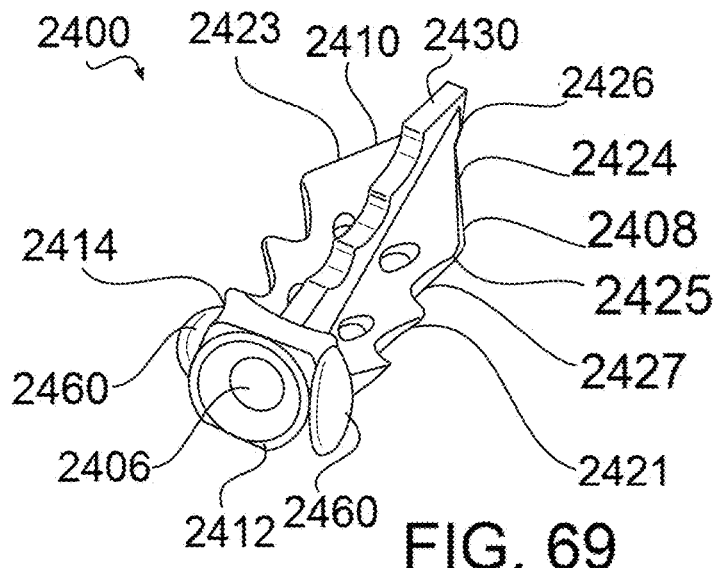
FIGS. 69-72 illustrate various views of another exemplary vertebral anchor in accordance with an example of the present disclosure.
Figure 72:
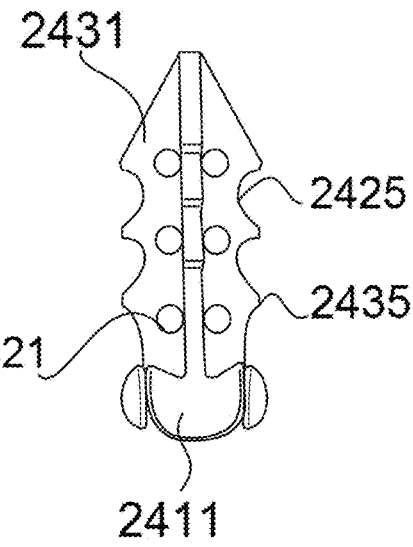
Figure 70:
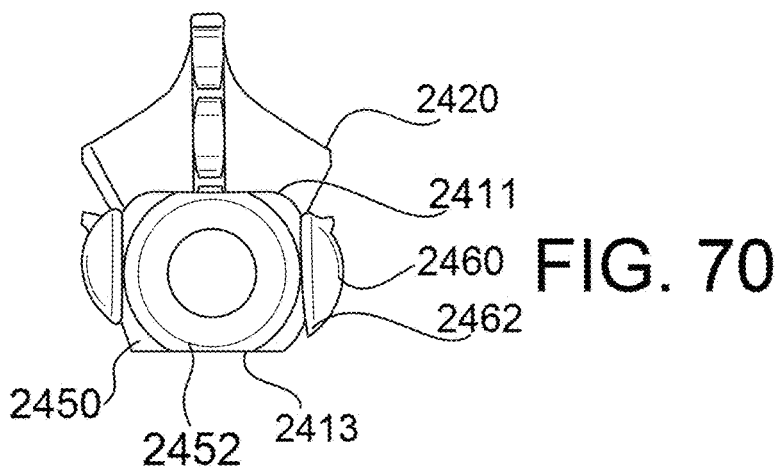
Figure 71:
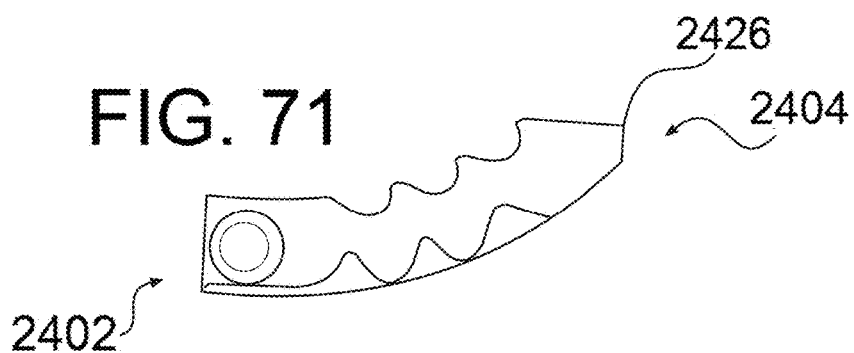

FIGS. 58-60 depict an exemplary method of positioning a vertebral anchor 2400 via insertion device 2200. Referring to FIG. 58, vertebral anchor 2400 is shown loaded into an anchor channel 2224. The vertebral anchor 2400 may be secured within the anchor channel 2224 by any suitable mechanism. Guide member 2228 then may be advanced distally such that the distal end of guide member 2228 may contact head portion 2406 of vertebral anchor 2400 (FIG. 58). Guide member 2228 may extend from trailing end 2202, through a trailing opening 2226 (shown in FIG. 57) of anchor channel 2224 to abut a vertebral anchor 2400. Vertebral anchor 2400 then may be advanced out of the leading end of anchor housing 2220 and anchor channel 2224 (FIG. 59) and ultimately inserted into a vertebral body (not shown) along a given exit trajectory, as shown in FIG. 60. After impacting one vertebral anchor 2400 through a vertebral body, anchor housing 2220 may be disengaged from plate portion 2092, and another vertebral anchor 2400 may be loaded into anchor channel 2224. When anchor channel 2224 is reloaded, anchor housing 2220 may be re-engaged with plate portion 2092 in a substantially similar manner as before, except that anchor channel 2224 may be aligned with a different bore 2093 of vertebral spacer 2090.

A vertebral anchor 2300 shown in FIG. 2029 may extend from a first, trailing end 2302 toward a second, leading end

2304, and may include a head portion 2306, an elongate shank 2308, and an elongate fin 2310. Vertebral anchor 2300 may be formed from a rigid, bio-compatible material such as, e.g., titanium or polyetheretherketone (PEEK), among others. The head portion 2306, elongate shank 2308, and elongate fin 2310 may be formed of the same or of different materials. Portions of vertebral anchor 2300 may be treated with a titanium and/or hydroxyapatite plasma spray coating to encourage bony on-growth, improving the strength and stability of the connection between the respective component and the underlying bone (e.g., a vertebral body). Any other suitable coating also may be provided on one or more surfaces of vertebral anchor 2300. Such coatings may include therapeutic agents (e.g., antibiotic coatings), if desired. Vertebral anchor 2300 also may include radiopaque markings to facilitate in vivo visualization and insertion. Vertebral anchor 2300 may be configured to be impacted into vertebral bodies to secure implants within the intervertebral space of a patient. Vertebral anchor 2300 may be inserted into the patient and impacted through the bone of a vertebral body.

The head portion 2306 may be disposed at trailing end 2302 of vertebral anchor 2300 and may be generally spherical or ball shaped. In some examples, the head portion 2306 may be shaped in a substantially similar manner as the head portion of other vertebral fastening members (e.g., bone screws). In some examples, the head portion 2306 may include a bore 2312 to facilitate removal of vertebral anchor 2300 from a vertebral body. In some examples, bore 2312 may be a threaded bore or may include other suitable features to facilitate the extraction of vertebral anchor 2300 from a vertebral body by, e.g., a pulling tool or the like. In some examples, a tool with a threaded tip may be rotated to threadingly engage bore 2312, and the tool may be linearly withdrawn to extract vertebral anchor 2300 from within a vertebral body. The pooling tool also may include one or more of a cam attachment, an expandable driver, or another feature for removing vertebral anchor 2300. A plurality of slots or notches 2314 may be formed in the outer periphery of head portion 2306. In some examples, a plurality of flanges 2316 may define the plurality of slots 2314 about the outer periphery of the head portion 2306. The flanges 2316 may be disposed around head portion 2306 to form a generally t-shaped cross-section. A groove 2318 (e.g., a semi-cylindrical groove) may be formed in the outer periphery of head portion 2306. In some examples, the groove 2318 may be disposed within one of the flanges 2316, or in another suitable location on head portion 2306. In some examples, one or more grooves 2318 may be disposed along the periphery of head portion 2306. Groove 2318 may cooperate with an extension (e.g., extension 2144 shown in FIG. 50) of an installation device as discussed above. In some examples, the flanges 2316 and slots 2314 of the head portion 2306 may cooperate with or be received by complimentary shaped features in a spacer, implant, plate system or the like. The interaction between the flanges 2316, slots 2314, and the complimentary-shaped features may prevent the relative rotation of vertebral anchor 2300 before, during and/or after installation of vertebral anchor 2300 into a vertebral body.

Elongate shank 2308 may extend away from the head portion 2306 toward the leading end 2304. In some examples, elongate shank 2308 may be planar and may exhibit a curvature as it extends away from the head portion 2306. That is to say, in some examples, elongate shank 2308 may include a curvilinear configuration. Specifically, elongate shank 2308 may be curved (e.g., symmetrically curved) about a longitudinal axis. More specifically, elongate shank 2308 exhibit a curvature about a median longitudinal axis. Further, the elongate shank 2308 may be curved such that a concave surface 2320 and a convex surface 2322 extend from trailing end 2302 toward leading end 2304. The leading end of the elongate shank 2308 may be formed by a pair of inclined surfaces 2323 and 2324 that extend from the lateral ends of elongate shank 2308 toward an apex 2326. Apex 2326 may be disposed on a longitudinal axis of vertebral anchor 2300. Thus, at leading end 2304, elongate shank 2308 may be formed as a projectile point, arrowhead, bladed edge, cutting edge, or the like to facilitate impaction and insertion through bone and/or tissue. To reduce impaction force, the apex 2326 may feature a hollow style which may be similar to a knife edge. That is, the edge or apex 2326 of the anchor may approach a shallow angle, e.g., approximately 15 degrees at the sharpest point, which may increase closer to a central axis. In some examples, apex 2326 may be rounded to prevent injury, but may still be sharp around its edges. To further reduce insertion force and manufacturing time, the hollow surfaces may be surface machined using, e.g., a 1 mm full radius mill and, e.g., a 0.25 mm step-over, which may result in the wavy surface (including a plurality of rolling peaks and valleys) along the face of the hollow surface. As further shown in FIGS. 61-68, inclined surfaces 2123 and 2124 may include one or more geometric features, such as, e.g., serrations (shown in FIG. 62), teeth, tapers, bevels or the like to further facilitate spearing, cutting, slicing, or impacting of elongate shank 2308 through bone and/or tissue. Inclined surfaces 2323 and 2324 also may be formed with an edge (e.g., a v-edge, beveled edge, chisel edge, convex edge or the like) to facilitate impaction.

Elongate fin 2310 also may extend away from head portion 2306 toward the leading end 2304 of vertebral anchor 2300. Elongate fin 2310 also may extend away from the concave surface 2320 of the elongate shank 2308. The vertical periphery of elongate fin 2310 may be defined by a concave surface 2328. In some examples, the elongate shank 2308 and elongate fin 2310 may be generally orthogonal to one another and may form a generally t-shaped cross-section. The t-shaped cross-section formed by elongate shank 2308 and elongate fin 2310 may reduce impaction forces of vertebral anchor 2300, and may increase the torsional stability of vertebral anchor 2300 as compared to anchors having planar cross-sections. At leading end 2304, elongate fin 2310 may include a ramped surface 2130 that extends toward apex 2326. Ramped surface 2330 may include one or more of the geometrical features described with reference to inclined surfaces 2323 and 2324. In some examples, a vertical periphery of ramp 2130 may be beveled and/or have a v-shaped cross-section.

Turning now to FIGS. 69-72, a further embodiment of a vertebral anchor 2400 is depicted. Vertebral anchor 2400 may extend from a first, trailing end 2402 toward a second, leading end 2404, and may include a head portion 2406, an elongate shank 2408, and an elongate fin 2428. Vertebral anchor 2400 may be formed from one or more of the materials used to form vertebral anchor 2300 and may be treated with one or more similar coatings, if desired. Vertebral anchor 2400 may be inserted into a patient and impacted through bone of a vertebral body.

The head portion 2406 may be disposed at trailing end 2402 of vertebral anchor 2400 and may have a partially spherical outer periphery. In some examples, the head portion 2406 may be formed by a plurality of spherical segments formed by removing one or more spherical caps from the spherical outer periphery of head portion 2406. In the embodiments shown in FIGS. 69-72, at least three planar surfaces 2411, 2413, and 2450 may define at least a portion of the outer periphery of the partially-spherical head portion 2406. In one example, planar surfaces 2411 and 2413 may be substantially parallel to one another, and may be substantially orthogonal to planar surface 2450. In some examples, planar surface 2450 may define the proximal-most portion of head portion 2406 and of vertebral anchor 2400. That is, planar surface 2450 may define the surface that is furthest toward trailing end 2402 of vertebral anchor 2400. A recess (e.g., a concave recess) 2452 may be disposed within planar surface 2450 such that planar surface 2450 may be defined by interrupted hemispherical arc portions, as seen in FIG. 64. A bore 2412 may have an opening disposed within recess 2452. Bore 2412 may extend through head portion 2406 and may include one or more features described with reference to bore 2312 of vertebral anchor 2300. While not shown in FIGS. 69-72, it is contemplated that head portion 2406 may include other features described with reference to head portion 2306 of vertebral anchor 2300, such as, e.g., grooves and/or mating features configured to secure and position vertebral anchor 2400 within an anchor channel of an insertion device.

Head portion 2406 also may include one or more protrusions 2460 that may extend away from the outer periphery of head portion 2406. In the examples shown, protrusions 2460 may be formed as spherical caps (e.g., partial domes), although protrusions 2460 may be formed in any other suitable configuration. In some examples, the base of protrusions 2460 may include an annular rim 2462 that may, e.g., extend radially away from protrusions 2460. In some examples, head portion 2406 may include two protrusions 2460 that extend in opposite directions. It is contemplated that another suitable number of protrusions 2460 may be employed in alternative configurations.

Elongate shank 2408 may extend away from the head portion 2406 toward the leading end 2404. In some examples, elongate shank 2408 may be planar and may exhibit a curvature as it extends away from the head portion 2406. In some examples, elongate shank 2408 may be curved (e.g., symmetrically curved) about a longitudinal axis. More specifically, elongate shank 2408 may exhibit a curvature about a median longitudinal axis. Further, the elongate shank 2408 may be curved such that a concave surface 2420 and a convex surface 2422 extend from trailing end 2402 toward leading end 2404. The leading end of the elongate shank 2408 may be formed by a pair of inclined surfaces 2423 and 2424 that extend from the lateral ends of elongate shank 2408 toward an apex 2426. Apex 2426 may be disposed on a longitudinal axis of vertebral anchor 2400. In some embodiments, apex 2426 may include a curvilinear periphery. Thus, at leading end 2404, elongate shank 2408 may be formed to include any of the suitable geometries and features disposed on vertebral anchor 2300 to facilitate impaction.

In one example, the lateral sides of elongate shank 2408 may include one or more cutouts 2421. For example, each lateral side of elongate shank 2408 may include two cutouts 2421 to form one or more keels 2425. The keels 2425 may generally extend and point in a reverse manner with respect to a remainder of vertebral anchor 2400. That is, the end points of the keels 2425 may be oriented toward the trailing end 2402 and not leading end 2404. Thus, keels 2425 may assist in inhibiting vertebral anchor 2400 from exiting a vertebral body once inserted therein. In the embodiment shown in FIGS. 63-66, each lateral side of elongate shank 2408 may include two cutouts 2421 and three keels 2425, although any other suitable combination of cutouts and keels may be utilized.

One or more apertures 2427 may disposed through the surface of elongate shank 2408. Though depicted as through-holes, apertures 2427 also may include blind recesses disposed in one or more surfaces of elongate shank 2308. Once inserted through the bone of a vertebral body, apertures 2427 may encourage bony in-growth or on-growth therein, further securing vertebral anchor 2400 within a respective vertebral body. In some examples, apertures 2427 may be packed with bone graft or other bone-growth inducing substances.

Elongate fin 2428 also may extend away from head portion 2406 toward the leading end 2404 of vertebral anchor 2400. Elongate fin 2428 also may extend away from the concave surface of the elongate shank 2408. The vertical periphery of elongate fin 2428 may be defined by one or more cutouts 2431 and keels 2435 in a substantially similar manner as the lateral sides of elongate shank 2408. In some examples, the elongate shank 2408 and elongate fin 2428 may be generally orthogonal to one another and may form a generally t-shaped cross-section. The t-shaped cross-section formed by elongate shank 2408 and elongate fin 2428 may reduce impaction forces of vertebral anchor 2400, and may increase the torsional stability of vertebral anchor 2400 as compared to anchors having planar cross-sections. At leading end 2404, elongate fin 2428 may include a ramped surface 2430 that extends toward apex 2426. Ramped surface 2430 may include one or more of the geometrical features described with reference to inclined surfaces 2423 and 2424. In some examples, apertures (not shown but similar to apertures 2427) may be disposed on or through elongate fin 2428 to encourage bony in-growth or on-growth therein.

In some examples, vertebral anchors 2300 and 2400 may facilitate easy insertion of various vertebral spacers (e.g., stand-alone ACDF and/or ALIF spacers) through the use of inline impaction of anchors 2300 and 2400 through the spacer. In some examples, the inline operation may be facilitated through appropriate implant design, instrument design, and design of the implant-instrument interface. In some examples, the various examples of the present disclosure may permit the use of stand-alone spacers at the most caudal or most cephalad cervical disc spaces (e.g., C5-C6/C6-C7 and C2-C3), and at the caudal lumbar levels (e.g., L5-S1) where angled instruments may pose insertion problems due to interference with tissue or other anatomy.

In addition to the embodiments above, additional plate and spacer systems can be provided that are of low profile. These plate and spacer systems are advantageously capable of providing multiple options to a surgeon. In particular, they allow a surgeon to choose the type of spacer (e.g., PEEK or allograft) to accompany the plate. In addition, they allow a surgeon to choose whether to use a straight bone anchor, a curved bone anchor, or a combination of both in order to be inserted into a patient.

Figure 73:
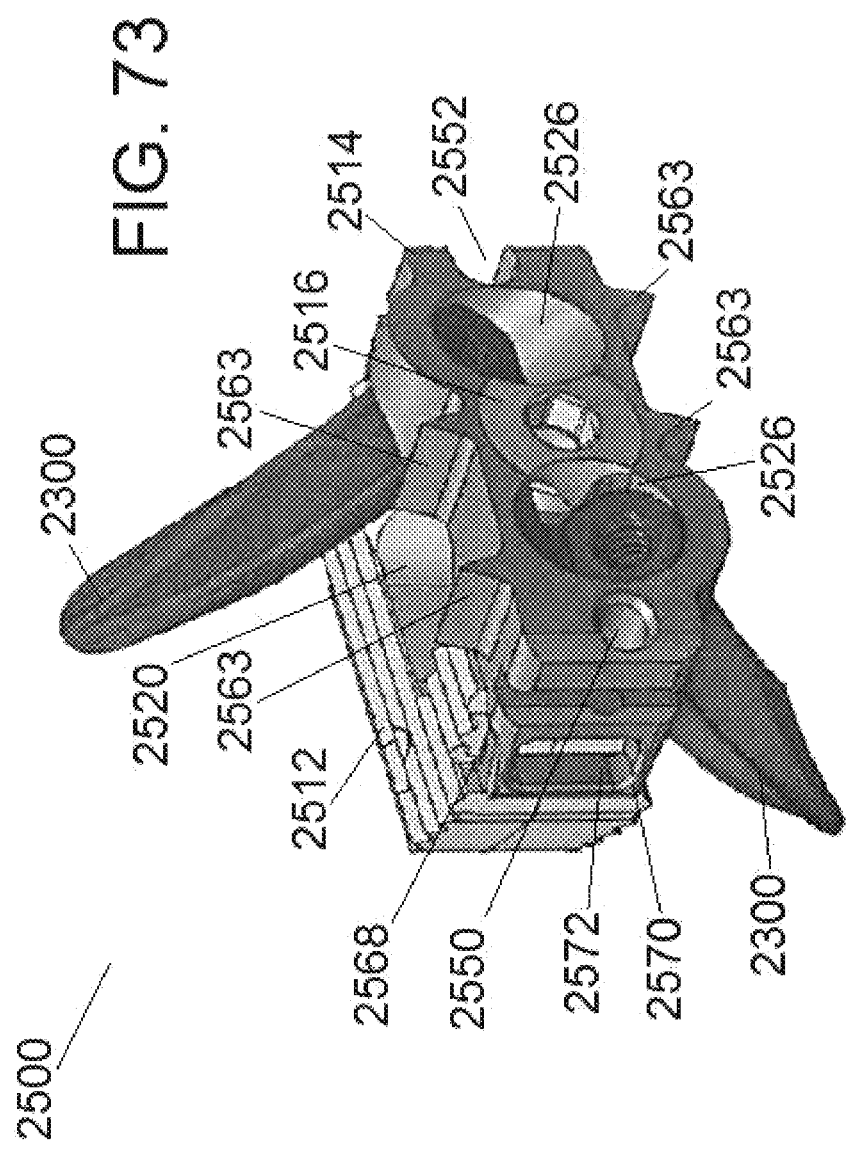
FIG. 73 is a top perspective view of a plate and spacer system with curved bone anchors in accordance with some embodiments.

FIG. 73 is a top perspective view of a plate and spacer system with curved bone anchors in accordance with some embodiments. The plate and spacer system 2500 is advantageously low profile. In addition, the plate and spacer system 2500 provides numerous options, such as the ability to use a PEEK or allograft spacer, as well as the ability to use straight or curved bone anchors.

The plate and spacer system 2500 comprises a novel, low profile plate 2514 including a pair of bore holes 2526 for receiving a bone fastener therein. In the present embodiment, the plate 2514 receives a pair of non-threaded, curved bone fasteners, shims or anchors 2300 (similar to the curved bone fasteners in FIGS. 61 and 67). Advantageously, these curved bone fasteners 2300 can be easily impacted into bone, without having to thread them therein. In other embodiments, the plate 2514 can received straight, threaded bone fasteners. In addition, in other embodiments, the plate 2514 can receive at least one non-threaded, curved bone fastener and at least one straight, threaded bone fastener. The plate 2514 is configured to receive at least one blocking member 2516. The blocking member 2516 can be in the form of a fastener with cutouts. In a first configuration, the cutouts of the blocking member 2516 each align with a perimeter of the adjacent bore hole 2526, thereby allowing a bone fastener to pass therethrough. In a second configuration, the blocking member 2516 is rotated such that the cutouts do not align with the perimeter of an adjacent bore hole 2526, thereby preventing a fastener from inadvertent backout.

In addition, the plate 2514 comprises torsional stabilizers 2563, which provides the system 2500 with stability as it is engaged with bone. In the present embodiment, the plate and spacer system 2500 includes a pair of upper torsional stabilizers 2563 for gripping a superior vertebrae and a pair of lower torsional stabilizers 2563 for gripping lower vertebrae. In some embodiments, the torsional stabilizers 2563 include pointed, knife-like edges, while in other embodiments, the torsional stabilizers 2563 include blunted edges. In some embodiments, the plate and spacer system 2500 includes less than two or more than two upper torsional stabilizers 2563, and similarly, less than two or more than two lower torsional stabilizers 2563.

The plate 2514 further comprises a pair of extensions or arms 2570 that extend from a front plate portion. Each of the arms 2570 includes a window 2572 that is designed to receive a bump out portion of the spacer 2512, thereby connecting the spacer 2512 to the plate 2514. In some embodiments, the window 2572 comprises a fully-enclosed perimeter that extends around a bump out portion of the spacer 2512. In some embodiments, the distal end of each of the arms 2570 comprises a lateral, inwardly facing protrusion 2568 that is received in a respective notch or groove of the spacer 2512. Accordingly, the plate and spacer system 2500 advantageously include multiple ways to secure the plate 2514 to the spacer 2512 thereby forming a secure system.

As shown in FIG. 73, the plate 2514 includes a pair of channels 2550, 2552 for receiving an insertion instrument therein. In some embodiments, the channels 2550, 2552 can differ from one another. For example, channel 2550 can comprise a full enclosed, threaded opening or hole that is designed to receive a threaded portion of an instrument. Channel 2552 can be a partially enclosed, non-threaded opening that includes a hook engagement cut out for receiving a non-threaded portion of an instrument. In some embodiments, a single instrument (such as that in FIG. 42) can be provided that includes both a threaded portion and a non-threaded hook portion. The instrument can be used to deposit one or more curved or straight fasteners.

The plate and spacer system 2500 further includes at least one spacer 2512 that is attachable to the plate 2514. Advantageously, a surgeon can choose the type of spacer 2512 to be attached to the plate 2514, such as an allograft spacer or PEEK spacer. The spacer 2512 includes a central opening for receiving graft material 2520 therein. In addition, the spacer 2512 can include superior and inferior surfaces having surface texturing thereon to better engage adjacent vertebrae. In the present embodiment, the spacer 2512 comprises a plurality of ridges on the superior and inferior surfaces.

Figure 74:
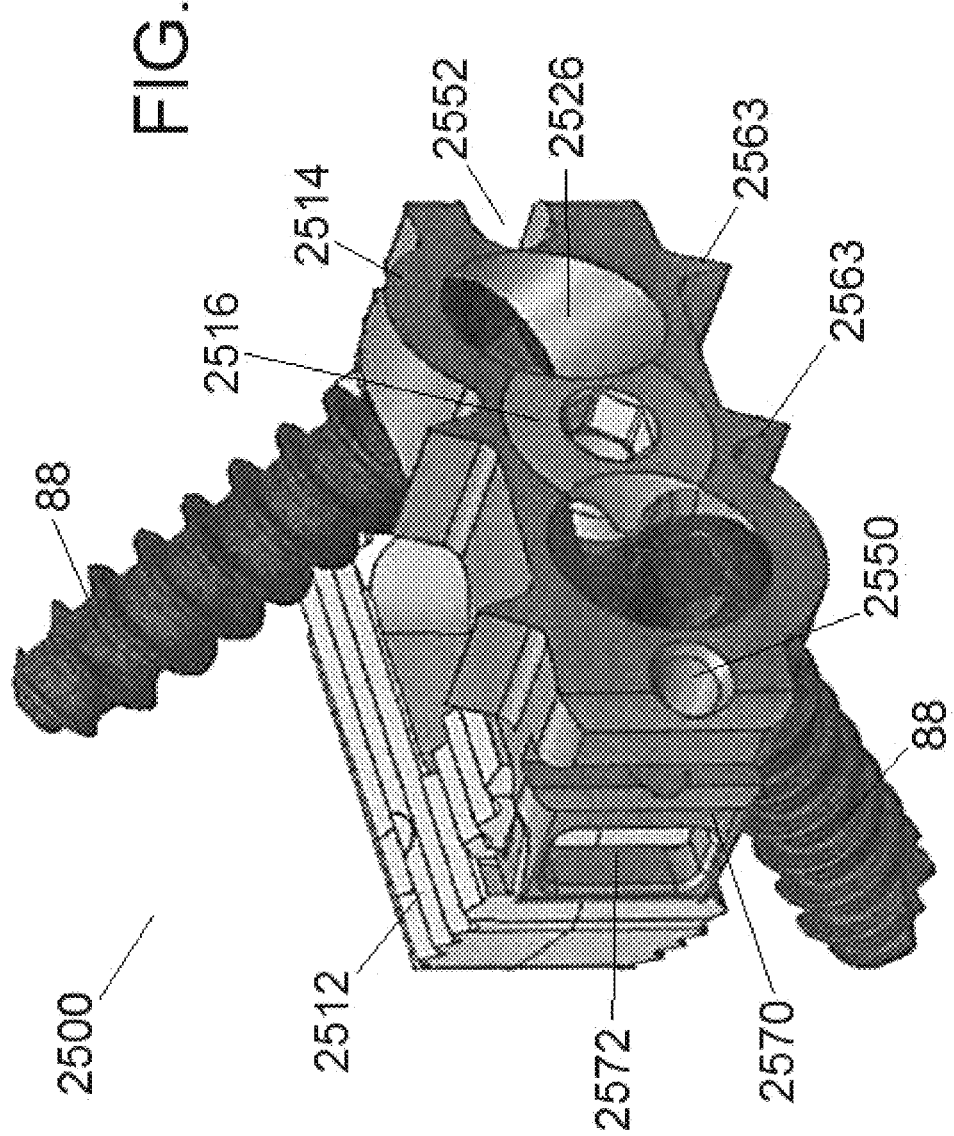
FIG. 74 is a top perspective view of a plate and spacer system with straight bone anchors in accordance with some embodiments.

FIG. 74 is a top perspective view of a plate and spacer system with straight bone anchors in accordance with some embodiments. While the plate and spacer system 2500 is similar to that of FIG. 73 such that the plate 2514 and the spacer 2512 include similar features, the present embodiment is shown as receiving straight, threaded bone fasteners 88 received through the plate 2514. The present embodiment thus demonstrates the ability of the plate to receive either straight, threaded bone fasteners 88 or curved, non-threaded bone fasteners or anchors 2300 depending on the desires of the surgeon.

Figure 75:
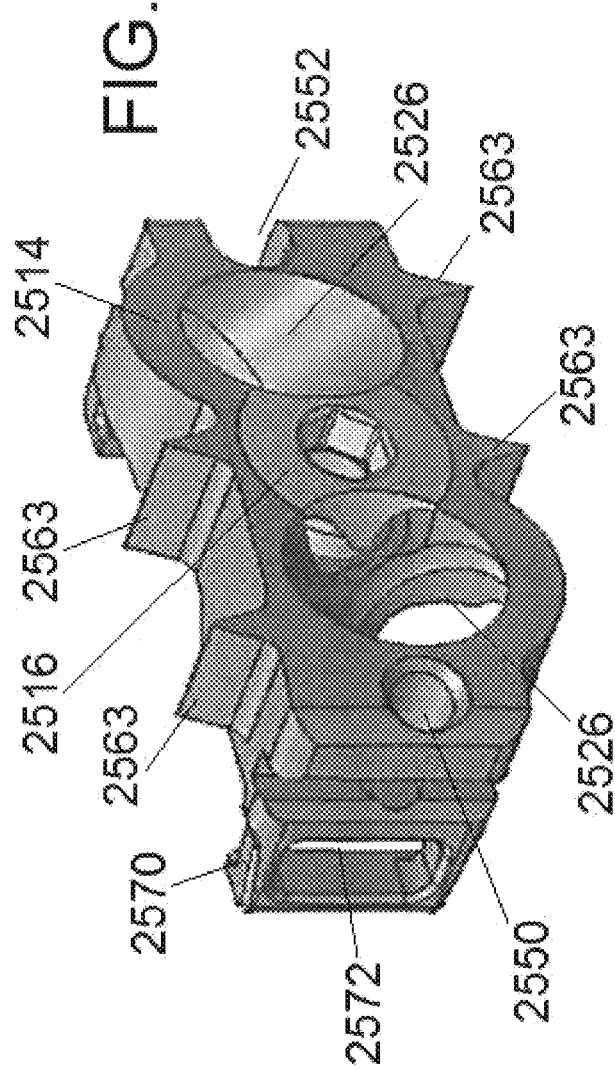
FIG. 75 is a top perspective view of a plate in accordance with some embodiments.

FIG. 75 is a top perspective view of a plate in accordance with some embodiments. From this view, one can see the plate 2514 detached from the spacer 2512 without any fastener received therein. As shown in FIG. 75, the bore holes 2526 of the plate 2514 can be non-threaded, and are capable of accommodating any of the fasteners or anchors described above. In other embodiments, the bore holes 2526 can be completely or partially threaded.

Figure 76:
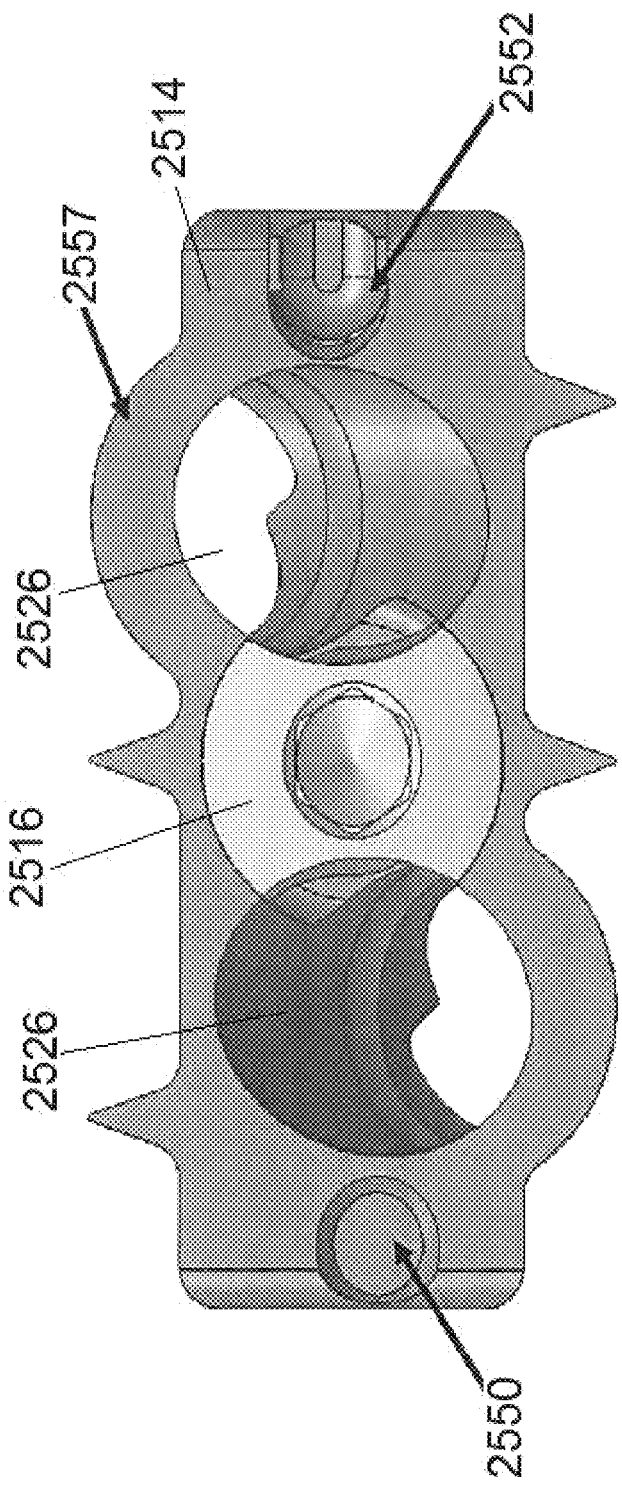
FIG. 76 is a front view of the plate of FIG. 75.

FIG. 76 is a front view of the plate of FIG. 75. From this view, one can see the channels 2550, 2552 for receiving different portions of an instrument therein. One can see how the channel 2550 comprises a threaded hole completed enclosed by a perimeter, whereas channel 2552 comprises a non-threaded hole partially enclosed by a perimeter.

Figure 77:
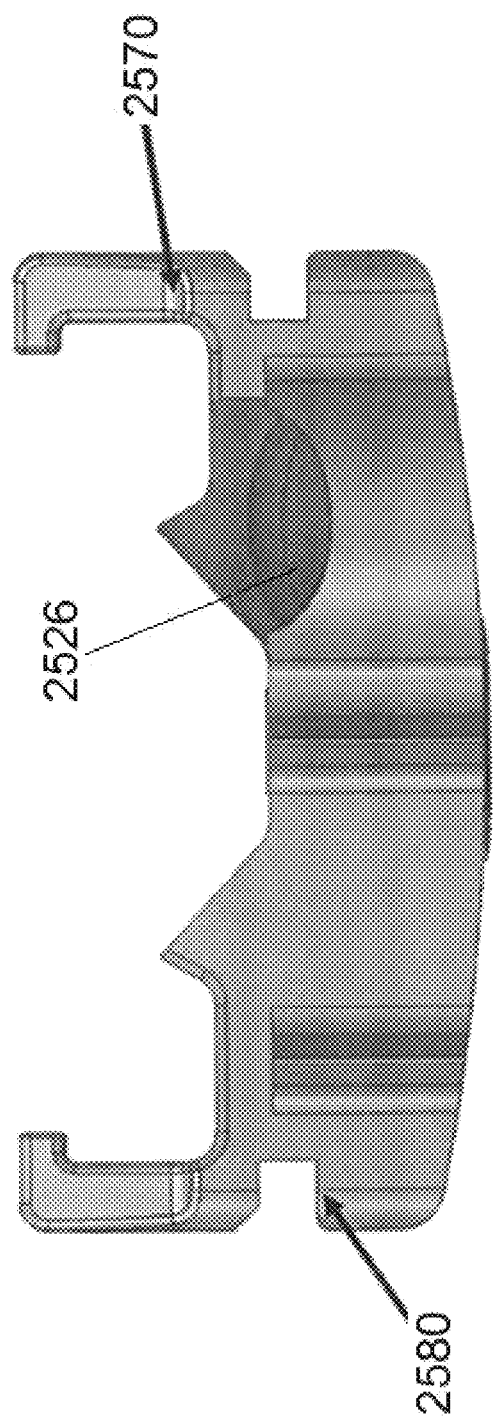
FIG. 77 is a top view of the plate of FIG. 75.

FIG. 77 is a top view of the plate of FIG. 75. From this view, one can see a pair of lateral tracks 2580 that extend through sidewalls of the plate. These lateral tracks 2580 advantageously accommodate a press assembly (not shown) that can be used to press a desired spacer 2512 onto the plate 2514.

Figure 78:
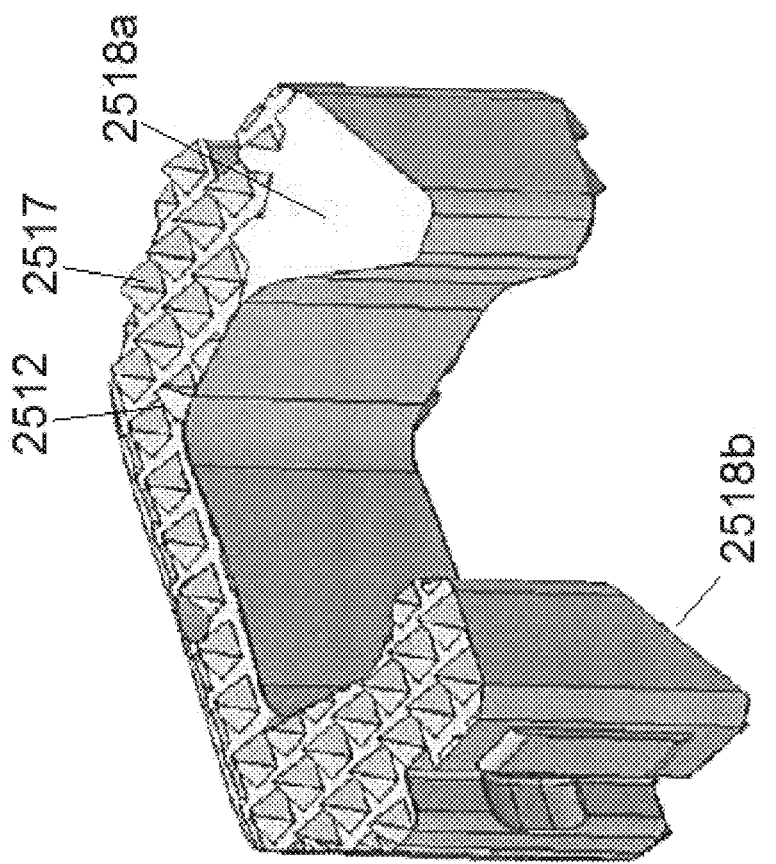
FIG. 78 is a top perspective view of a PEEK spacer in accordance with some embodiments.

FIG. 78 is a top perspective view of a PEEK spacer in accordance with some embodiments. The spacer 2512 comprises a C-shape spacer having a superior surface and an inferior surface with a plurality of protrusions formed thereon. In addition, the spacer 2512 comprises a flatly cut upper chamfer 2518a and a flatly cut lower chamfer 2518b for providing clearance to a screw or anchor that is inserted through the plate.

Figure 79:
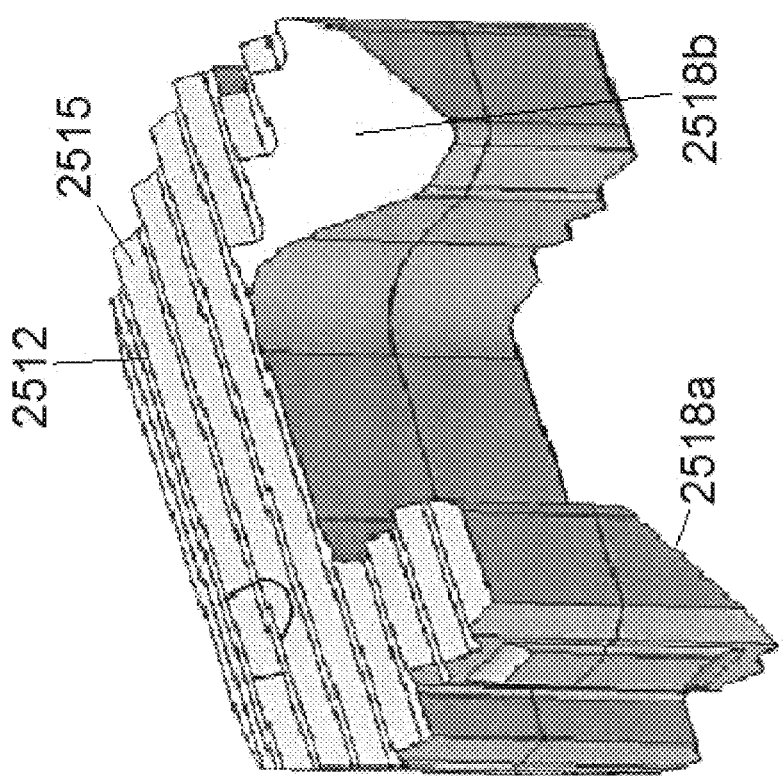
FIG. 79 is a top perspective view of an allograft spacer in accordance with some embodiments.

FIG. 79 is a top perspective view of an allograft spacer in accordance with some embodiments. The spacer 2512 comprises a C-shaped spacer having a superior surface and an inferior surface with a plurality of ridges formed thereon. In addition, the spacer 2512 comprises a flatly cut upper chamfer 2518a and a flatly cut lower chamfer 2518b for providing clearance to a screw or anchor that is inserted through the plate.

FIG. 80 is a top perspective view of an alternative allograft spacer in accordance with some embodiments. The spacer 2512 comprises a C-shaped spacer having a superior surface and an inferior surface with a plurality of ridges formed thereon. In addition, the spacer 2512 comprises a curved cut upper chamfer 2518a and a curved cut lower chamfer 2518b for providing clearance to a screw or anchor that is inserted through the plate. In some embodiments, the curved chamfers better conform to a screw or anchor that is received through the plate. In addition, the curved chamfers 2518a, 2518b allow for more material to be left on the spacer 2512 during manufacturing, which makes the spacer 2512 stronger.

Figure 81A:
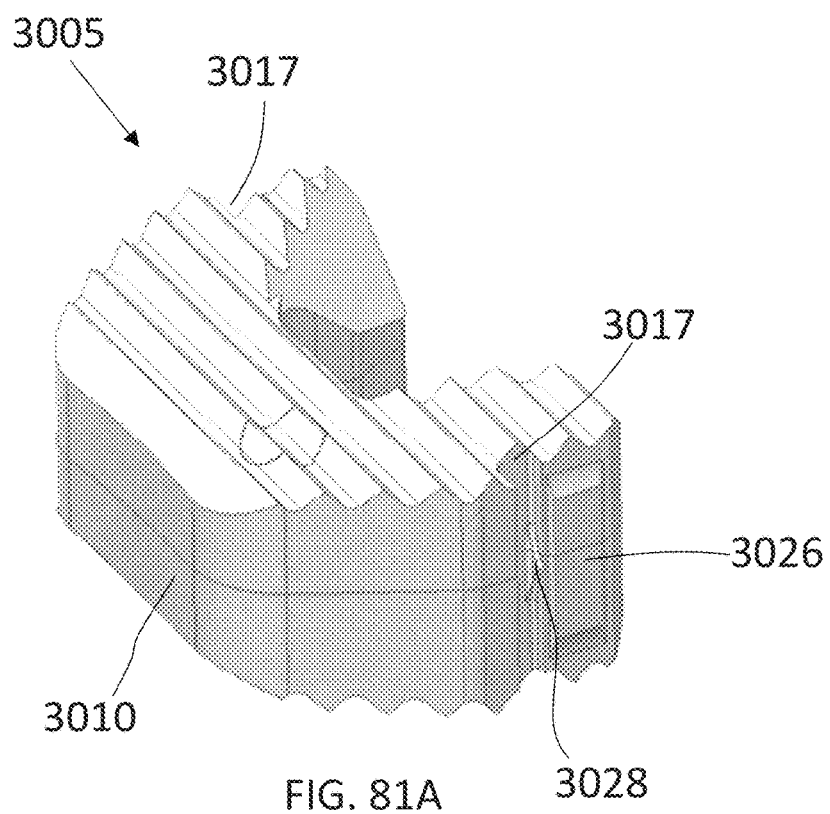
FIGS. 81A and 81B provide top perspective views of a spacer and a plate and spacer system, respectively, in accordance with one embodiment.
Figure 81B:
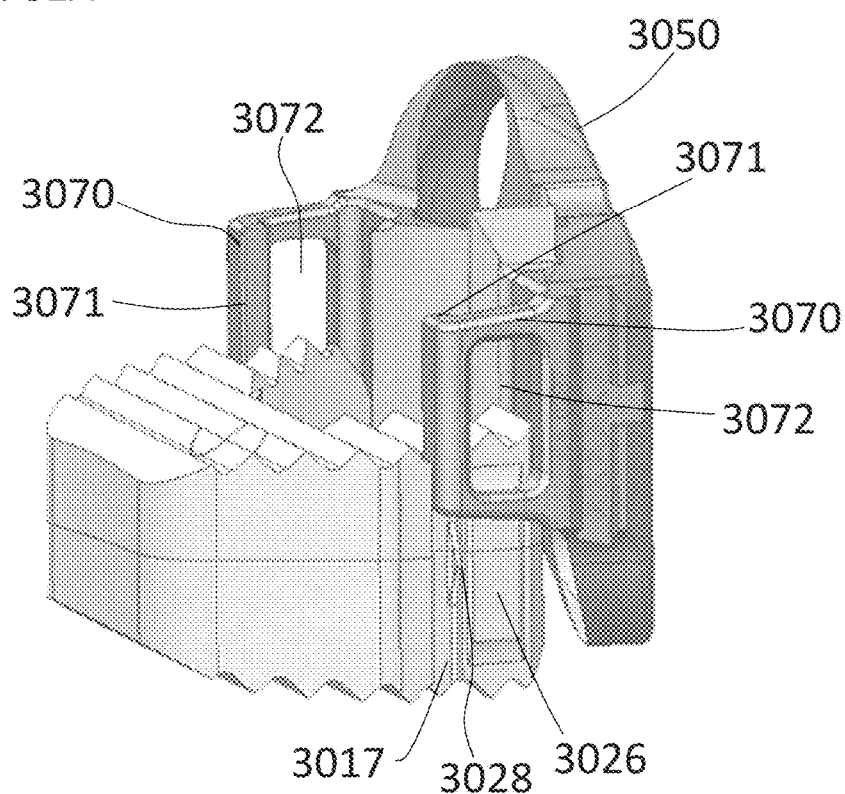

Turning now to FIGS. 81A-81B, an alternative plating system 3005 comprising a low profile plate 3050 attached to a spacer 3010 is shown. Plating system 3005 is similar to the other spacer and plate systems described herein with the addition of an interference 3028 adjacent the hump regions or protrusions 3026 configured to fit in window 3072 in arms or extensions 70 of the plate 3050. It is desirable for the spacer 3010 to fit snugly to the plate 3050. The interference 3028 may enhance the fit of the spacer 3010 to the plate 3050 by allowing the small amount of material of the interference 3028 to deform during the assembly process. By deforming the interference 3028, the system 3005 may better accommodate tolerance of machining and/or the varying shrink rates encountered in the lyophilization process for allograft spacers 3010.

In particular, the interference 3028 may be located in the notches or slots 3017 in the spacer 3010 configured to receive the inwardly facing protrusions 3071 on the ends of the arms 3070. The interference 3028 may include a minor protrusion including two sloped surfaces meeting at a central apex. The interference 3028 may be elongated along the length of the slots 3017. For example, the slots 3017 in the spacer 3010 may be provided with uneven and/or offset surfaces to provide small amounts of interference when the spacer 3010 is assembled to the plate 3050. Small interference surfaces within the slots 3017 are easy to manufacture and can account for machining tolerances stackup between the two mating components. The interference 3028 may also help to accommodate the varying shrink rates encountered in the lyophilization process for allograft spacers post-machining.

One skilled in the art will appreciate that any of the plate systems described above can be used with other spinal implants. Among the other implants that can accompany the plate systems include stabilization systems and rod systems, including rod members, hook members, and bone fasteners such as pedicle screws. One skilled in the art will appreciate that any of the plate systems described above can also be used with one another, or can be used multiple times along different segments of the spine. In addition, any of the plate systems described above can be used with a variety of navigation and guidance tools, including those related to neuromonitoring and robotics. Furthermore, one of skill in the art will appreciate that the plate systems described above can be produced in a number of different ways, including in part via 3-D printing methods.

It will be apparent to those skilled in the art that various modifications and variations can be made in the present invention without departing from the scope or spirit of the invention. Moreover, the improved plate systems and bone screw assemblies and related methods of use need not feature all of the objects, advantages, features and aspects discussed above. Thus, for example, those skilled in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed bone screw assemblies. Thus, it is intended that the present invention cover the modifications and variations of this invention provided that they come within the scope of the appended claims or their equivalents.

What is claimed is:

1. A spinal system comprising:
   a plate member including an upper rim and a lower rim, the plate member further including a first arm and a second arm, the first arm and the second arm each including at least one window;
   a spacer having first and second lateral sides, the first and second lateral sides defining the width of the spacer, wherein the spacer attaches to the plate member by engaging the first lateral side of the spacer with the at least one window in the first arm and engaging the second lateral side of the spacer with the at least one window in the second arm;
   a first screw upwardly insertable through an upper screw hole of the upper rim; and
   a second screw downwardly insertable through a lower screw hole of the lower rim, wherein protrusions on the spacer are configured to fit in the at least one window of the first arm and the second arm.

2. The spinal system of claim 1, wherein the upper rim of the plate member includes an anterior face and a posterior face, wherein each of the anterior face and the posterior face are straight and non-angled with respect to a vertical axis defined by the spacer.

3. The spinal system of claim 1, wherein the upper rim of the plate member includes an anterior face and a posterior face, wherein at least one of the anterior face and the posterior face are angled with respect to a vertical axis defined by the spacer.

4. The spinal system of claim 3, wherein the posterior face of the upper rim is angled between 5 and 15 degrees in an anterior direction relative to a longitudinal axis that extends vertically from an upper surface of the spacer to a lower surface of the spacer.

5. The spinal system of claim 1, wherein the plate member includes a rotatable locking mechanism designed to prevent backout of the first screw and the second screw from the plate member.

6. The spinal system of claim 1, wherein the plate member includes a stabilizer for inserting partially into a disc space.

7. The spinal system of claim 1, wherein a height of each window is greater than a length of each window.

8. The spinal system of claim 1, further comprising a graft opening, the graft opening being defined by the plate member and the spacer.

9. A plate configured to fixate two adjacent vertebral bodies, the plate comprising:
   a body;
   an upper rim extending from the body and a lower rim extending from the body, wherein the upper rim includes an upper screw hole extending through the upper rim and having an upper screw hole center axis and the lower rim includes a lower screw hole extending through the lower rim and having a lower screw hole center axis;
   a first screw insertable through the upper screw hole, wherein the first screw is oriented in an upward direction; and
   a second screw insertable through the lower screw hole, wherein the second screw is oriented in a downward direction;
   wherein the body comprises a first window and a second window configured to attach the body to a spacer, and wherein the upper screw hole center axis is positioned entirely above an upper surface of the spacer and the lower screw hole center axis is positioned entirely below a lower surface of the spacer, wherein protrusions on the spacer are configured to fit in the first window and the second window of the body of the plate.

10. The plate of claim 9, further comprising a graft opening, the graft opening being defined by the plate and the spacer.

11. The plate of claim 9, wherein the spacer comprises a tapered upper surface and a tapered lowered surface.

12. The plate of claim 9, wherein the spacer is formed of allograft or PEEK.

13. The plate of claim 9, wherein the spacer comprises a first bump out portion and a second bump out portion, wherein the first bump out portion is securable to a first arm of the plate and the second bump out portion is securable to a second arm of the plate member.

14. The plate of claim 13, wherein the first arm comprises the first window configured to receive the first bump out portion of the spacer and the second arm comprises the second window configured to receive the second bump out portion of the spacer.

15. The plate of claim 9, wherein the plate includes a stabilizer that extends upwardly and a second stabilizer that extends downwardly.

16. The plate of claim 9, wherein the upper rim has a front surface and a back surface, wherein at least one of the front surface and the back surface is angled in an anterior direction.

17. The plate of claim 16, wherein both the front surface and the back surface of the upper rim are angled in an anterior direction.

18. The plate of claim 9, wherein the upper rim has a front surface and a back surface, wherein both the front surface and the back surface are non-angled with respect to a vertical axis defined by the spacer.

19. The plate of claim 9, wherein the first window has a height greater than a length of the first window.

* * * * *